M

United States Patent [19]

Light, II et al.

[11] Patent Number: 5,770,356
[45] Date of Patent: Jun. 23, 1998

[54] PHAGEMIDS COEXPRESSING A SURFACE RECEPTOR AND A SURFACE HETEROLOGOUS PROTEIN

[75] Inventors: James Paul Light, II, San Diego; Richard A. Lerner, La Jolla, both of Calif.

[73] Assignee: The Scripps Research Institute, La Jolla, Calif.

[21] Appl. No.: 387,874

[22] PCT Filed: Sep. 3, 1993

[86] PCT No.: PCT/US93/08364

§ 371 Date: Feb. 22, 1995

§ 102(e) Date: Feb. 22, 1995

[87] PCT Pub. No.: WO94/05781

PCT Pub. Date: Mar. 17, 1994

Related U.S. Application Data

[63] Continuation-in-part of Ser. No. 941,369, Sep. 4, 1992, abandoned.

[51] Int. Cl.⁶ .............................. C12Q 1/68; C12Q 1/70; C12N 1/21; C12N 15/64
[52] U.S. Cl. ................................ 435/5; 435/6; 435/7.1; 435/172.3; 435/252.33; 435/320.1
[58] Field of Search .............................. 435/69.1, 172.1, 435/172.3, 320.1, 69.7, 235.1, 5, 6, 7.1, 7.2, 29, 252.33

[56] References Cited

U.S. PATENT DOCUMENTS

| 5,223,409 | 6/1993 | Ladner | 435/69.7 |
|---|---|---|---|
| 5,403,848 | 4/1995 | Ladner | 514/325 |

FOREIGN PATENT DOCUMENTS

| WO88/06630 | 9/1988 | WIPO . |
|---|---|---|
| WO90/14424 | 11/1990 | WIPO . |
| WO91/17271 | 11/1991 | WIPO . |
| WO91/18980 | 12/1991 | WIPO . |
| WO91/19818 | 12/1991 | WIPO . |
| WO92/01047 | 1/1992 | WIPO . |
| WO92/06204 | 4/1992 | WIPO . |
| WO92/07077 | 4/1992 | WIPO . |

OTHER PUBLICATIONS

Jaenicke, Prog. Biophys. Malec. Biol., vol. 49, pp. 117–237, 1987.
Bass, et al., "Hormone Phage: An Enrichment Method for Variant Proteins With Altered Binding Properties", *Proteins: Structure, Function and Genetics*, 8:309–314 (1990).
Bird, et al., "Single–Chain Antigen–Binding Proteins", *Science*, 242:423–6 (1988).
Boss, et al., "Assembly of Functional Antibodies from Immunoglobulin Heavy and Light Chains Synthesized in *E. coli*", *Nuc. Acids Res.*, 12:3791–3806(1984).
Cabilly, et al., Generation of Antibody–Activity from Immunoglobulin Polypeptide Chains Produced in *Escherichia coli*, *Proc. Natl. Acad. Sci., USA* 81:3273–3277 (1984).

Caton, et al., "Influenza Virus Hemagglutinin–Specific Antibodies Isolated From a Combinatorial Expression Library are Closely Related to the Immune Response of the Donor", *Proc. Natl. Acad. Sci., USA*, 87:6450–6454 (1990).
Devlin, et al., "Random Peptide Libraries: A Source of Specific Protein Binding Molecules", *Science*, 249:404–406 (1990).
Larrick, et al., "Polymerase Chain Reaction Using Mixed Primers: Cloning of Human Monoclonal Antibody Variable Region Genes from Single Hybridoma Cells", *Biotechnology*, 7:934–938(1989).
Marks, et al., "By–Passing Immunization Human Antibodies from V–Gene Libraries Displayed on Phage", *J. Mol. Biol.*, 222:581–597 (1991).
Model, et al., "Filamentous Bacteriophage", ed. R. Calendar, Plenum Publishing Corp., 2:375–456 (1988).
Mullinax, et al., "Identification of Human Antibody Fragment Clones Specific for Tetanus Toxoid in a Bacteriophage Alpha Immunoexpression Library", *Proc. Natl. Acad. Sci., USA*, 87:8095–8099 (1990).
O'Neill, et al., "Design of DNA–Binding Peptides Based on the Leucine Zipper Motif", *Science*, 249:774–778 (1990).
Orlandi, et al., "Cloning Immunoglobulin Variable Domains for Expression by the Polymerase Chain Reaction", *Proc. Natl. Acad. Sci., USA*, 86:3833–3837 (1989).
Pluckthun, A., "Antibodies from *Escherichia Coli*", *Nature*, 347:497–498 (1990).
Rasched, et al., "Ff Coliphages: Structural and Functional Relationships", *Microbiol. Rev.*, 50:401–427 (1986).
Roberts, et al., "Protease Inhibitor Display M13 Phage: Selection of High–Affinity Neutrophil Elastase Inhibitors", *Gene*, 121:9–15 (1992).
Roberts, et al., "Directed Evolution of a Protein: Selection of Potent Neutrophil Elastase Inhibitors Displayed on M13 Fusion Phage", *Proc. Natl. Acad. Sci., USA*, 89:2429–2433 (1992).
Sastry, et al., "Cloning of the Immunological Repertoire in *E. coli* for Generationof Monoclonal Catalytic Antibodies: Construction of a Heavy Chain Variable Region–Specific cDNA Library", *Proc. Natl. Acad. Sci., USA*, 86: 5728–5732 (1989).
Scott, et al., "Searching for Peptide Ligands with an Epitope Library", *Science*, 249:386–390 (1990).

(List continued on next page.)

*Primary Examiner*—David Guzo
*Attorney, Agent, or Firm*—Thomas Fitting; Emily Holmes

[57] ABSTRACT

A filamentous phage is described comprising a matrix that includes a heterologous polypeptide fused to a first filamentous phage coat protein membrane anchor and a heterodimeric receptor comprised of first and second receptor polypeptides, wherein one of the receptor polypeptides is fused to a second filamentous phage coat protein membrane anchor. Filamentous phage expressing anchored heterodimeric receptors and dimers of heterologous polypeptides where a first subunit of the dimer is fused to a coat protein membrane anchor and the second subunit of the dimer is soluble heteromeric receptor are also described.

45 Claims, 13 Drawing Sheets

OTHER PUBLICATIONS

Short, et al., Lambda ZAP: A Bacteriophage Lambda Expression Vector with in vitro Excision Properties, Nuc. Acids Res., 16:7583–7600 (1988).

Skerra, et al., "Assembly of a Functional Immunoglobulin Fv Fragment in *E. coli*" *Science,* 240:1038–1043 (1988).

Skerra, et al., "The Functional Expression of Antibody Fv Fragments in *E. coli* Improved Vectors and a Generally Applicable Purification Technique", *Biotechnology,* 9:273–278 (1991).

Smith, George P., "Filamentous Fusion Phage: Novel Expression Vectors That Display Cloned Antigens on the Virion Surface", *Science,* 228:1315–1317 (1985).

Solazzo, et al., "Expression of an Exogenous Peptide Epitope Genetically Engineered in the Variable Domain of an Immunoglobulin: Implications for Antibody and Peptide Folding", *Protein Engineering,* 4:215–220 (1990).

Takeda, et al., Construction of Chimaeric Processed Immunoglobulin Genes Containing Mouse Variable and Human Constant Region Sequences, *Nature,* 314:452–454 (1985).

Ward, et al., "Binding Activities of a Repertoire of Single Immunoglobulin Variable Domains Secreted from *Escherichia coli*", *Nature,* 341:544–546 (1989).

Barbas, et al., *Methods: A Companion to Methods in Enzymology,* 2: 119–124 (1991).

Barbas, et al., *Proc. Natl. Acad. Sci., USA,* 88: 7978–7982 (1991).

Barbas, et al., *Proc. Natl. Acad. Sci., USA,* 89: 4457–4461 (1992).

Burton, et al., *Proc. Natl. Acad. Sci., USA,* 88: 10134–10137 (1991).

Chang, et al., *Gene,* 44: 121–125 (1986).

Clackson, et al., *Nature,* 352: 624–628 (1991).

Cwirla, et al., *Proc. Natl. Acad. Sci., USA,* 87: 6378–6382 (1990).

Gram, et al., *Proc. Natl. Acad. Sci., USA,* 89: 3576–3580 (1992).

Il'ichev, et al., *Molekulyarynava Biologiya,* 24: 530–535 (1990).

Kang, et al., *Proc. Natl. Acad. Sci., USA,* 88: 4363–4366 (1991).

Kang, et al., *Proc. Natl. Acad. Sci., USA,* 88: 11120–11123 (1991).

Kang, et al., *Methods: A Companion to Methods in Enzymology,* 2: 111–118 (1991).

Larimer, et al., *Protein Engineering,* 3: 227–231 (1990).

Markland, et al., *Gene,* 109: 13–19 (1991).

McCafferty, et al., *Nature,* 348: 552–554 (1990).

McCafferty, et al., *J. Protein Engineering,* 4: 955–961 (1991).

Parmley, et al., *Gene,* 73: 305–318 (1988).

Persson, et al., *Proc. Natl. Acad. Sci., USA,* 88: 2432–2436 (1991).

Zebedee, et al., *Proc. Natl. Acad. Sci., USA,* 89: 3175–3179 (1992).

Wels, et al., "Construction, Bacterial Expression and Characterization of a Bifunctional Single–Chain Antibody–Phosphatase Fusion Protein Targeted to the Human ERBB–2 Receptor", *Bio/Technology,* 10:1128–1132 (1992).

```
                                        SHINE-DALGARNO  MET
         GGCCGCAAATTCTATTTCAAGGAGACAGTCATAATG
         CGTTTAAGATAAAGTTCCTCTGTCAGTATTAC

LEADER SEQUENCE

AAATACCTATTGCCTACGGCAGCCGCT
              TTTATGGATAACGGATGCCGTCGGCGA

LEADER SEQUENCE

GGATTGTTATTACTCGCTGCCCAACCAG
              CCTAACAATAATGAGCGACGGGTTGGTC

LINKER               LINKER

| NCOI | V_H BACKBONE | XHOI           SPEI |
         CCATGGCCCAGGTGAAACTGCTCGAGATTTCTAGACTAGT
         GGTACCGGGTCCACTTTGACGAGCTCTAAAGATCTGATCA

STOP      LINKER
         TyrProTyrAspValProAspTyrAlaSer
         TACCCGTACGACGTTCCGGACTACGTTCTTAATAGAATTCG
         ATGGGCATGCTGCAAGGCCTGATGCAAGAATTATCTTAAGCAGCT
```

FIG.1

ECOR I  SHINE-DALGARNO  MET

TGAATTCTAAACTAGTCGCCAAGGAGACAGTCATAATGAAAT
TCGAACTTAAGATTTGATCAGCGGTTCCTCTGTCAGTATTACTTTA

LEADER SEQUENCE

ACCTATTGCCTACGGCAGCCGCTGGATTGTTATTACTCGCTGCCCAACCAG
TGGATAACGGATGCCGTCGGCGACCTAACAATAATGAGCGACGGGTTGGTC

NCO I  SAC I  XBA I  Not I

CCATGGCCGAGCTCGTCAGTTCTAGAGTTAAGCGGCCG
GGTACCGGCTCGAGCAGTCAGAAGATCTCAATTCGCCGGCAGCT

FIG.3

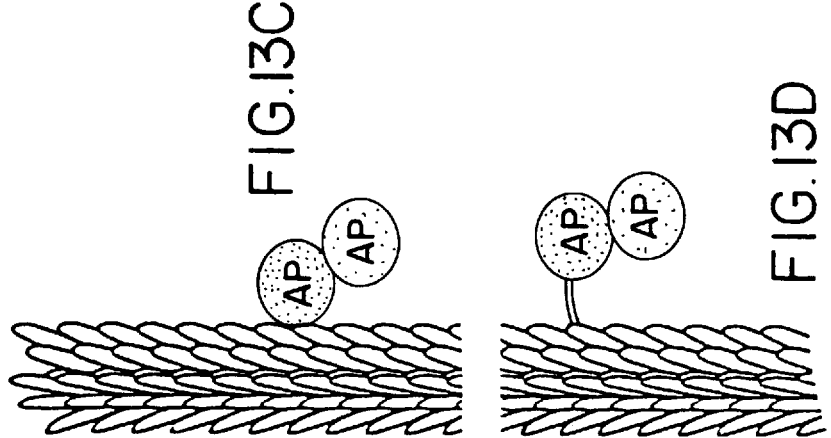
FIG.13C
FIG.13D
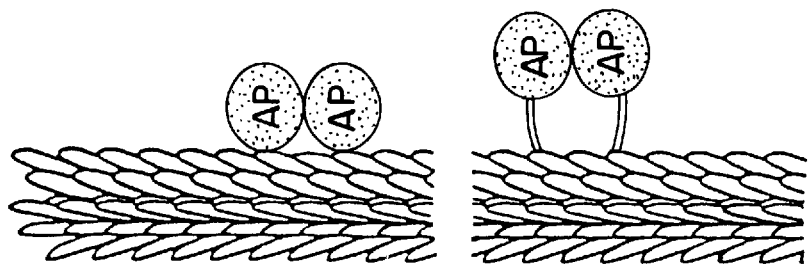
FIG.13A
FIG.13B

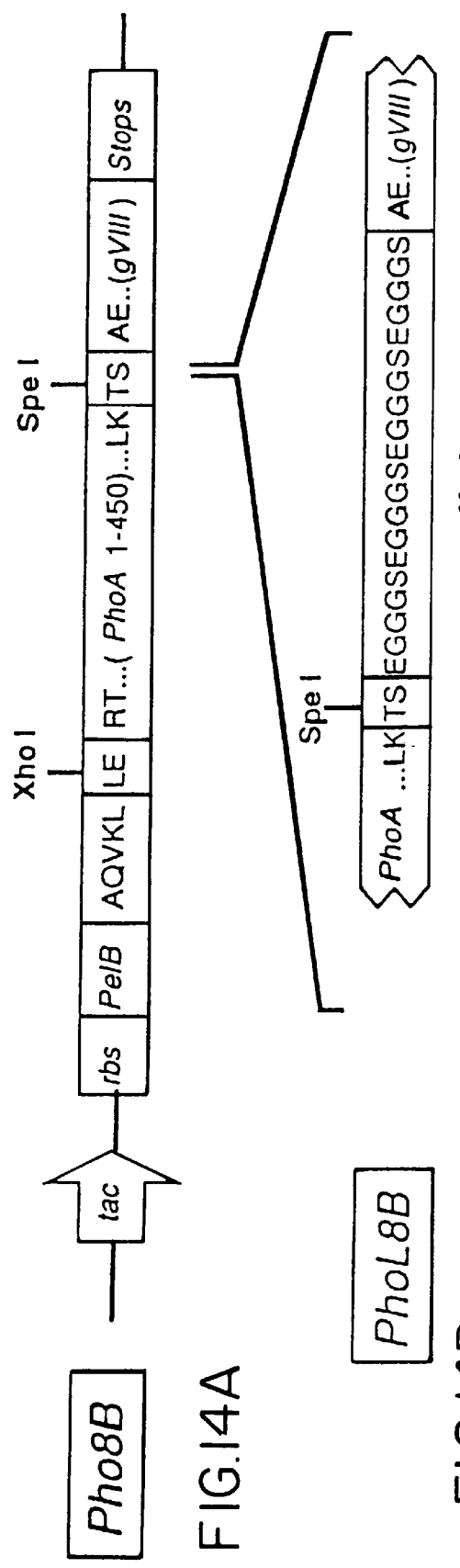
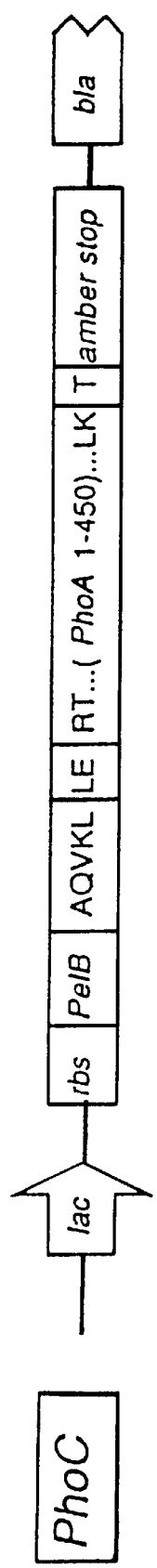
FIG.14A  FIG.14B  FIG.14C

SEQUENCE LISTING ( 1 ) GENERAL INFORMATION:

( i i i ) NUMBER OF SEQUENCES: 97

( 2 ) INFORMATION FOR SEQ ID NO:1:

( i ) SEQUENCE CHARACTERISTICS:
        ( A ) LENGTH: 173 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

| | | | | | |
|---|---|---|---|---|---|
| GGCCGCAAAT | TCTATTTCAA | GGAGACAGTC | ATAATGAAAT | ACCTATTGCC | TACGGCAGCC | 60
| GCTGGATTGT | TATTACTCGC | TGCCCAACCA | GCCATGGCCC | AGGTGAAACT | GCTCGAGATT | 120
| TCTAGACTAG | TTACCCGTAC | GACGTTCCGG | ACTACGGTTC | TTAATAGAAT | TCG | 173

( 2 ) INFORMATION FOR SEQ ID NO:2:

( i ) SEQUENCE CHARACTERISTICS:
        ( A ) LENGTH: 173 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

| | | | | | |
|---|---|---|---|---|---|
| TCGACGAATT | CTATTAAGAA | CCGTAGTCCG | GAACGTCGTA | CGGGTAACTA | GTCTAGAAAT | 60
| CTCGAGCAGT | TTCACCTGGG | CCATGGCTGG | TTGGGCAGCG | AGTAATAACA | ATCCAGCGGC | 120
| TGCCGTAGGC | AATAGGTATT | TCATTATGAC | TGTCTCCTTG | AAATAGAATT | TGC | 173

( 2 ) INFORMATION FOR SEQ ID NO:3:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

| | | | | | |
|---|---|---|---|---|---|
| TGAATTCTAA | ACTAGTCGCC | AAGGAGACAG | TCATAATGAA | ATACCTATTG | CCTACGGCAG | 60
| CCGCTGGATT | GTTATTACTC | GCTGCCCAAC | CAGCCATGGC | CGAGCTCGTC | AGTTCTAGAG | 120

TTAAGCGGCC G 131

( 2 ) INFORMATION FOR SEQ ID NO:4:

( i ) SEQUENCE CHARACTERISTICS:
        ( A ) LENGTH: 139 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

TCGACGGCCG CTTAACTCTA GAACTGACGA GCTCGGCCAT GGCTGGTTGG GCAGCGAGTA 60

ATAACAATCC AGCGGCTGCC GTAGGCAATA GGTATTTCAT TATGACTGTC TCCTTGGCGA 120

CTAGTTTAGA ATTCAAGCT 139

( 2 ) INFORMATION FOR SEQ ID NO:5:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:5:

Met Lys Tyr Leu Leu Pro Thr Ala Ala Ala Gly Leu Leu Leu Leu Ala
1               5                   10                  15

Ala Gln Pro Ala Met
            20

( 2 ) INFORMATION FOR SEQ ID NO:6:

( i ) SEQUENCE CHARACTERISTICS:
        ( A ) LENGTH: 25 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Erwinia carotovora ( x i ) SEQUENCE DESCRIPTION: SEQ ID NO:6:

Met Lys Tyr Leu Leu Pro Thr Ala Ala Ala Gly Leu Leu Leu Leu Ala
1               5                   10                  15

Ala Gln Pro Ala Gln Pro Ala Met Ala
            20              25

( 2 ) INFORMATION FOR SEQ ID NO:7:

( i ) SEQUENCE CHARACTERISTICS:
        ( A ) LENGTH: 22 amino acids
        ( B ) TYPE: amino acid
        ( D ) TOPOLOGY: unknown (  i i ) MOLECULE TYPE: peptide ( i i i ) HYPOTHETICAL: NO ( i v ) ANTI-SENSE: NO ( v i ) ORIGINAL SOURCE:
       ( A ) ORGANISM: Erwinia carotovora ( x i ) SEQUENCE DESCRIPTION: SEQ ID NO:7:

```
Met  Lys  Ser  Leu  Ile  Thr  Pro  Ile  Ala  Ala  Gly  Leu  Leu  Leu  Ala  Phe
1              5                        10                       15
Ser  Gln  Tyr  Ser  Leu  Ala
             20
```

( 2 ) INFORMATION FOR SEQ ID NO:8:

( i ) SEQUENCE CHARACTERISTICS:
        ( A ) LENGTH: 28 amino acids
        ( B ) TYPE: amino acid
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:8:

```
Met  Lys  Ile  Lys  Thr  Gly  Ala  Arg  Ile  Leu  Ala  Leu  Ser  Ala  Leu  Thr
1              5                        10                       15
Thr  Met  Met  Phe  Ser  Ala  Ser  Ala  Leu  Ala  Lys  Ile
             20                       25
```

( 2 ) INFORMATION FOR SEQ ID NO:9:

( i ) SEQUENCE CHARACTERISTICS:
        ( A ) LENGTH: 24 amino acids
        ( B ) TYPE: amino acid
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:9:

```
Met  Met  Lys  Arg  Asn  Ile  Leu  Ala  Val  Ile  Val  Pro  Ala  Leu  Leu  Val
1              5                        10                       15
Ala  Gly  Thr  Ala  Asn  Ala  Ala  Glu
             20
```

( 2 ) INFORMATION FOR SEQ ID NO:10:

( i ) SEQUENCE CHARACTERISTICS:
        ( A ) LENGTH: 23 amino acids
        ( B ) TYPE: amino acid
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:10:

```
Met  Lys  Gln  Ser  Thr  Ile  Ala  Leu  Ala  Leu  Leu  Pro  Leu  Leu  Phe  Thr
1              5                        10                       15
Pro  Val  Thr  Lys  Ala  Arg  Thr
             20
```

( 2 ) INFORMATION FOR SEQ ID NO:11:

( i ) SEQUENCE CHARACTERISTICS:
    ( A ) LENGTH: 25 amino acids
    ( B ) TYPE: amino acid
    ( D ) TOPOLOGY: unknown ( i i ) MOLECULE TYPE: peptide ( i i i ) HYPOTHETICAL: NO ( x i ) SEQUENCE DESCRIPTION: SEQ ID NO:11:

```
Met Ser Ile Gln His Phe Arg Val Ala Leu Ile Pro Phe Phe Ala Ala
  1               5                   10                  15
Phe Cys Leu Pro Val Phe Ala His Pro
                20              25
```

( 2 ) INFORMATION FOR SEQ ID NO:12:

( i ) SEQUENCE CHARACTERISTICS:
    ( A ) LENGTH: 27 amino acids
    ( B ) TYPE: amino acid
    ( D ) TOPOLOGY: unknown ( i i ) MOLECULE TYPE: peptide ( i i i ) HYPOTHETICAL: NO ( x i ) SEQUENCE DESCRIPTION: SEQ ID NO:12:

```
Met Met Ile Thr Leu Arg Lys Leu Pro Leu Ala Val Ala Val Ala Ala
  1               5                   10                  15
Gly Val Met Ser Ala Gln Ala Met Ala Val Asp
                20              25
```

( 2 ) INFORMATION FOR SEQ ID NO:13:

( i ) SEQUENCE CHARACTERISTICS:
    ( A ) LENGTH: 22 amino acids
    ( B ) TYPE: amino acid
    ( D ) TOPOLOGY: unknown ( i i ) MOLECULE TYPE: peptide ( i i i ) HYPOTHETICAL: NO ( x i ) SEQUENCE DESCRIPTION: SEQ ID NO:13:

```
Met Lys Ala Thr Lys Leu Val Leu Gly Ala Val Ile Leu Gly Ser Thr
  1               5                   10                  15
Leu Leu Ala Gly Cys Ser
                20
```

( 2 ) INFORMATION FOR SEQ ID NO:14:

( i ) SEQUENCE CHARACTERISTICS:
    ( A ) LENGTH: 23 amino acids
    ( B ) TYPE: amino acid
    ( D ) TOPOLOGY: unknown ( i i ) MOLECULE TYPE: peptide ( i i i ) HYPOTHETICAL: NO ( x i ) SEQUENCE DESCRIPTION: SEQ ID NO:14:

```
Met Lys Lys Ser Leu Val Leu Lys Ala Ser Val Ala Val Ala Thr Leu
  1               5                   10                  15
Val Pro Met Leu Ser Phe Ala
                20
```

( 2 ) INFORMATION FOR SEQ ID NO:15:

(  i ) SEQUENCE CHARACTERISTICS:
(  A ) LENGTH: 18 amino acids
(  B ) TYPE: amino acid
(  D ) TOPOLOGY: unknown (  i i ) MOLECULE TYPE: peptide (  i i i ) HYPOTHETICAL: NO (  x i ) SEQUENCE DESCRIPTION: SEQ ID NO:15:

| Met | Lys | Lys | Leu | Leu | Phe | Ala | Ile | Pro | Leu | Val | Val | Pro | Phe | Tyr | Ser |
|---|---|---|---|---|---|---|---|---|---|---|---|---|---|---|---|
| 1 | | | | 5 | | | | | 10 | | | | | 15 | |

| His | Ser |
|---|---|

( 2 ) INFORMATION FOR SEQ ID NO:16:

(  i ) SEQUENCE CHARACTERISTICS:
(  A ) LENGTH: 211 amino acids
(  B ) TYPE: amino acid
(  D ) TOPOLOGY: unknown (  i i ) MOLECULE TYPE: protein (  i i i ) HYPOTHETICAL: NO (  v ) FRAGMENT TYPE: internal (  x i ) SEQUENCE DESCRIPTION: SEQ ID NO:16:

| Pro | Phe | Val | Cys | Glu | Tyr | Gln | Gly | Gln | Gly | Gln | Ser | Ser | Asp | Leu | Pro |
|---|---|---|---|---|---|---|---|---|---|---|---|---|---|---|---|
| 1 | | | | 5 | | | | | 10 | | | | | 15 | |

| Gln | Pro | Pro | Val | Asn | Ala | Gly | Gly | Gly | Ser | Gly | Gly | Gly | Ser | Gly | Gly |
|---|---|---|---|---|---|---|---|---|---|---|---|---|---|---|---|
| | | | 20 | | | | | 25 | | | | | 30 | | |

| Gly | Ser | Glu | Gly | Gly | Gly | Ser | Glu | Gly | Gly | Gly | Ser | Glu | Gly | Gly | Gly |
|---|---|---|---|---|---|---|---|---|---|---|---|---|---|---|---|
| | | 35 | | | | | 40 | | | | | 45 | | | |

| Ser | Glu | Gly | Gly | Gly | Ser | Gly | Gly | Gly | Ser | Gly | Ser | Gly | Asp | Phe | Asp |
|---|---|---|---|---|---|---|---|---|---|---|---|---|---|---|---|
| | | 50 | | | | | 55 | | | | | 60 | | | |

| Tyr | Glu | Lys | Met | Ala | Asn | Ala | Asn | Lys | Gly | Ala | Met | Thr | Glu | Asn | Ala |
|---|---|---|---|---|---|---|---|---|---|---|---|---|---|---|---|
| 65 | | | | | 70 | | | | | 75 | | | | | 80 |

| Asp | Glu | Asn | Ala | Leu | Gln | Ser | Asp | Ala | Lys | Gly | Lys | Leu | Asp | Ser | Val |
|---|---|---|---|---|---|---|---|---|---|---|---|---|---|---|---|
| | | | | 85 | | | | | 90 | | | | | 95 | |

| Ala | Thr | Asp | Tyr | Gly | Ala | Ala | Ile | Asp | Gly | Phe | Ile | Gly | Asp | Val | Ser |
|---|---|---|---|---|---|---|---|---|---|---|---|---|---|---|---|
| | | | 100 | | | | | 105 | | | | | 110 | | |

| Gly | Leu | Ala | Asn | Gly | Asn | Gly | Ala | Thr | Gly | Asp | Phe | Ala | Gly | Ser | Asn |
|---|---|---|---|---|---|---|---|---|---|---|---|---|---|---|---|
| | | | 115 | | | | | 120 | | | | | 125 | | |

| Ser | Gln | Met | Ala | Gln | Val | Gly | Asp | Gly | Asp | Asn | Ser | Pro | Leu | Met | Asn |
|---|---|---|---|---|---|---|---|---|---|---|---|---|---|---|---|
| | 130 | | | | | 135 | | | | | 140 | | | | |

| Asn | Phe | Arg | Gln | Tyr | Leu | Pro | Ser | Leu | Pro | Gln | Ser | Val | Glu | Cys | Arg |
|---|---|---|---|---|---|---|---|---|---|---|---|---|---|---|---|
| 145 | | | | | 150 | | | | | 155 | | | | | 160 |

| Pro | Phe | Val | Phe | Ser | Ala | Gly | Lys | Pro | Tyr | Glu | Phe | Ser | Ile | Asp | Cys |
|---|---|---|---|---|---|---|---|---|---|---|---|---|---|---|---|
| | | | | 165 | | | | | 170 | | | | | 175 | |

| Asp | Lys | Ile | Asn | Leu | Phe | Arg | Gly | Val | Phe | Ala | Phe | Leu | Leu | Tyr | Val |
|---|---|---|---|---|---|---|---|---|---|---|---|---|---|---|---|
| | | | | 180 | | | | | 185 | | | | | 190 | |

| Ala | Thr | Phe | Met | Tyr | Val | Phe | Ser | Thr | Phe | Ala | Asn | Ile | Leu | Arg | Asn |
|---|---|---|---|---|---|---|---|---|---|---|---|---|---|---|---|
| | | 195 | | | | | 200 | | | | | 205 | | | |

| Lys | Glu | Ser |
|---|---|---|
| | | 210 |

( 2 ) INFORMATION FOR SEQ ID NO:17:

(  i ) SEQUENCE CHARACTERISTICS:
(  A ) LENGTH: 50 amino acids (B) TYPE: amino acid
(D) TOPOLOGY: unknown (ii) MOLECULE TYPE: protein (iii) HYPOTHETICAL: NO (xi) SEQUENCE DESCRIPTION: SEQ ID NO:17:

| Ala | Glu | Gly | Asp | Asp | Pro | Ala | Lys | Ala | Ala | Phe | Asn | Ser | Leu | Gln | Ala |
|---|---|---|---|---|---|---|---|---|---|---|---|---|---|---|---|
| 1 | | | | 5 | | | | | 10 | | | | | 15 | |

| Ser | Ala | Thr | Glu | Tyr | Ile | Gly | Tyr | Ala | Trp | Ala | Met | Val | Val | Val | Ile |
|---|---|---|---|---|---|---|---|---|---|---|---|---|---|---|---|
| | | | 20 | | | | 25 | | | | | 30 | | | |

| Val | Gly | Ala | Thr | Ile | Gly | Ile | Lys | Leu | Phe | Lys | Lys | Phe | Thr | Ser | Lys |
|---|---|---|---|---|---|---|---|---|---|---|---|---|---|---|---|
| | | 35 | | | | | 40 | | | | | 45 | | | |

Ala Ser
50

(2) INFORMATION FOR SEQ ID NO:18:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: RNA (genomic)

(iii) HYPOTHETICAL: NO (iv) ANTI-SENSE: NO (xi) SEQUENCE DESCRIPTION: SEQ ID NO:18:

AAUCUUGGAG GCUUUUUUAU GGUUCGUUCU                       30

(2) INFORMATION FOR SEQ ID NO:19:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: RNA (genomic)

(iii) HYPOTHETICAL: NO (iv) ANTI-SENSE: NO (xi) SEQUENCE DESCRIPTION: SEQ ID NO:19:

UAACUAAGGA UGAAAUGCAU GUCUAAGACA                       30

(2) INFORMATION FOR SEQ ID NO:20:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: RNA (genomic)

(iii) HYPOTHETICAL: NO (iv) ANTI-SENSE: NO (xi) SEQUENCE DESCRIPTION: SEQ ID NO:20:

UCCUAGGAGG UUUGACCUAU GCGAGCUUUU                       30

(2) INFORMATION FOR SEQ ID NO:21:

( i ) SEQUENCE CHARACTERISTICS:
  ( A ) LENGTH: 30 base pairs
  ( B ) TYPE: nucleic acid
  ( C ) STRANDEDNESS: double
  ( D ) TOPOLOGY: linear ( i i ) MOLECULE TYPE: RNA (genomic)

( i i i ) HYPOTHETICAL: NO ( i v ) ANTI-SENSE: NO ( x i ) SEQUENCE DESCRIPTION: SEQ ID NO:21:

AUGUACUAAG GAGGUUGUAU GGAACAACGC          30

( 2 ) INFORMATION FOR SEQ ID NO:22:

( i ) SEQUENCE CHARACTERISTICS:
  ( A ) LENGTH: 32 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:22:

GGCCGCAAAT TCTATTTCAA GGAGACAGTC AT         32

( 2 ) INFORMATION FOR SEQ ID NO:23:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:23:

AATGAAATAC CTATTGCCTA CGGCAGCCGC TGGATT        36

( 2 ) INFORMATION FOR SEQ ID NO:24:

( i ) SEQUENCE CHARACTERISTICS:
  ( A ) LENGTH: 32 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:24:

GTTATTACTC GCTGCCCAAC CAGCCATGGC CC         32

( 2 ) INFORMATION FOR SEQ ID NO:25:

( i ) SEQUENCE CHARACTERISTICS:
  ( A ) LENGTH: 29 base pairs
  ( B ) TYPE: nucleic acid ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:25:

CAGTTTCACC TGGGCCATGG CTGGTTGGG                                      29

( 2 ) INFORMATION FOR SEQ ID NO:26:

( i ) SEQUENCE CHARACTERISTICS:
           ( A ) LENGTH: 40 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:26:

CAGCGAGTAA TAACAATCCA GCGGCTGCCG TAGGCAATAG                            40

( 2 ) INFORMATION FOR SEQ ID NO:27:

( i ) SEQUENCE CHARACTERISTICS:
           ( A ) LENGTH: 38 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:27:

GTATTTCATT ATGACTGTCT CCTTGAAATA GAATTTGC                              38

( 2 ) INFORMATION FOR SEQ ID NO:28:

( i ) SEQUENCE CHARACTERISTICS:
           ( A ) LENGTH: 40 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:28:

AGGTGAAACT GCTCGAGATT TCTAGACTAG TTACCCGTAC                            40

( 2 ) INFORMATION FOR SEQ ID NO:29:

( i ) SEQUENCE CHARACTERISTICS:
           ( A ) LENGTH: 38 base pairs
           ( B ) TYPE: nucleic acid
           ( C ) STRANDEDNESS: single
           ( D ) TOPOLOGY: linear ( i i ) MOLECULE TYPE: DNA (genomic)

(iii) HYPOTHETICAL: NO (iv) ANTI-SENSE: NO (xi) SEQUENCE DESCRIPTION: SEQ ID NO:29:

CGGAACGTCG TACGGGTAAC TAGTCTAGAA ATCTCGAG    38

(2) INFORMATION FOR SEQ ID NO:30:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:30:

GACGTTCCGG ACTACGGTTC TTAATAGAAT TCG    33

(2) INFORMATION FOR SEQ ID NO:31:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:31:

TCGACGAATT CTATTAAGAA CCGTAGTC    28

(2) INFORMATION FOR SEQ ID NO:32:

(i) SEQUENCE CHARACTERISTICS:
(A) LENGTH: 34 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:32:

TGAATTCTAA ACTAGTCGCC AAGGAGACAG TCAT    34

(2) INFORMATION FOR SEQ ID NO:33:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO ( x i ) SEQUENCE DESCRIPTION: SEQ ID NO:33:

AATGAAATAC CTATTGCCTA CGGCAGCCGC TGGATT 36

( 2 ) INFORMATION FOR SEQ ID NO:34:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:34:

GTTATTACTC GCTGCCCAAC CAGCCATGGC C 31

( 2 ) INFORMATION FOR SEQ ID NO:35:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:35:

GAGCTCGTCA GTTCTAGAGT TAAGCGGCCG 30

( 2 ) INFORMATION FOR SEQ ID NO:36:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:36:

GTATTTCATT ATGACTGTCT CCTTGGCGAC TAGTTTAGAA TTCAAGCT 48

( 2 ) INFORMATION FOR SEQ ID NO:37:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:37:

CAGCGAGTAA TAACAATCCA GCGGCTGCCG TAGGCAATAG 40

( 2 ) INFORMATION FOR SEQ ID NO:38:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:38:

TGACGAGCTC GGCCATGGCT GGTTGGG    27

( 2 ) INFORMATION FOR SEQ ID NO:39:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:39:

TCGACGGCCG CTTAACTCTA GAAC    24

( 2 ) INFORMATION FOR SEQ ID NO:40:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:40:

AGGTSMARCT KCTCGAGTCW GG    22

( 2 ) INFORMATION FOR SEQ ID NO:41:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:41:

AGGTCCAGCT GCTCGAGTCT GG    22

( 2 ) INFORMATION FOR SEQ ID NO:42:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:42:

AGGTCCAGCT GCTCGAGTCA GG 22

( 2 ) INFORMATION FOR SEQ ID NO:43:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:43:

AGGTCCAGCT TCTCGAGTCT GG 22

( 2 ) INFORMATION FOR SEQ ID NO:44:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:44:

AGGTCCAGCT TCTCGAGTCA GG 22

( 2 ) INFORMATION FOR SEQ ID NO:45:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:45:

AGGTCCAACT GCTCGAGTCT GG 22

( 2 ) INFORMATION FOR SEQ ID NO:46:

( i ) SEQUENCE CHARACTERISTICS:
( A ) LENGTH: 22 base pairs
( B ) TYPE: nucleic acid
( C ) STRANDEDNESS: single (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:46:

AGGTCCAACT GCTCGAGTCA GG 22

(2) INFORMATION FOR SEQ ID NO:47:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:47:

AGGTCCAACT TCTCGAGTCT GG 22

(2) INFORMATION FOR SEQ ID NO:48:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:48:

AGGTCCAACT TCTCGAGTCA GG 22

(2) INFORMATION FOR SEQ ID NO:49:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:49:

AGGTNNANCT NCTCGAGTCW GG 22

(2) INFORMATION FOR SEQ ID NO:50:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

( i i i ) HYPOTHETICAL: NO ( i v ) ANTI-SENSE: NO ( x i ) SEQUENCE DESCRIPTION: SEQ ID NO:50:

GCCCAAGGAT GTGCTCACC                              19

( 2 ) INFORMATION FOR SEQ ID NO:51:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:51:

CTATTAACTA GTAACGGTAA CAGTGGTGCC TTGCCCCA                              38

( 2 ) INFORMATION FOR SEQ ID NO:52:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:52:

CTCAGTATGG TGGTTGTGC                              19

( 2 ) INFORMATION FOR SEQ ID NO:53:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:53:

GCTACTAGTT TTGATTTCCA CCTTGG                              26

( 2 ) INFORMATION FOR SEQ ID NO:54:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:54:

AATTTTACTA GTCACCTTGG TGCTGCTGGC                                                30

( 2 ) INFORMATION FOR SEQ ID NO:55:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:55:

TATGCAACTA GTACAACCAC AATCCCTGGG CACAATTTT                                      39

( 2 ) INFORMATION FOR SEQ ID NO:56:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:56:

CCAGTTCCGA GCTCGTTGTG ACTCAGGAAT CT                                             32

( 2 ) INFORMATION FOR SEQ ID NO:57:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:57:

CCAGTTCCGA GCTCGTGTTG ACGCAGCCGC CC                                             32

( 2 ) INFORMATION FOR SEQ ID NO:58:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:58:

CCAGTTCCGA GCTCGTGCTC ACCCAGTCTC CA                                             32

( 2 ) INFORMATION FOR SEQ ID NO:59:

( i ) SEQUENCE CHARACTERISTICS:
      ( A ) LENGTH: 32 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:59:

CCAGTTCCGA GCTCCAGATG ACCCAGTCTC CA      32

( 2 ) INFORMATION FOR SEQ ID NO:60:

( i ) SEQUENCE CHARACTERISTICS:
      ( A ) LENGTH: 32 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:60:

CCAGATGTGA GCTCGTGATG ACCCAGACTC CA      32

( 2 ) INFORMATION FOR SEQ ID NO:61:

( i ) SEQUENCE CHARACTERISTICS:
      ( A ) LENGTH: 32 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:61:

CCAGATGTGA GCTCGTCATG ACCCAGTCTC CA      32

( 2 ) INFORMATION FOR SEQ ID NO:62:

( i ) SEQUENCE CHARACTERISTICS:
      ( A ) LENGTH: 32 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:62:

CCAGATGTGA GCTCTTGATG ACCCAAACTC AA      32

( 2 ) INFORMATION FOR SEQ ID NO:63:

( i ) SEQUENCE CHARACTERISTICS:

( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:63:

CCAGATGTGA GCTCGTGATA ACCCAGGATG AA 32

( 2 ) INFORMATION FOR SEQ ID NO:64:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:64:

GCAGCATTCT AGAGTTTCAG CTCCAGCTTG CC 32

( 2 ) INFORMATION FOR SEQ ID NO:65:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:65:

CCGCCGTCTA GAACACTCAT TCCTGTTGAA GCT 33

( 2 ) INFORMATION FOR SEQ ID NO:66:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:66:

CCGCCGTCTA GAACATTCTG CAGGAGACAG ACT 33

( 2 ) INFORMATION FOR SEQ ID NO:67:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:67:

GCGCCGTCTA GAATTAACAC TCATTCCTGT TGAA 34

(2) INFORMATION FOR SEQ ID NO:68:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:68:

CTATTAACTA GTAACGGTAA CAGTGGTGCC TTGCCCCA 38

(2) INFORMATION FOR SEQ ID NO:69:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:69:

AGGCTTACTA GTACAATCCC TGGGCACAAT 30

(2) INFORMATION FOR SEQ ID NO:70:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:70:

GCCGCTCTAG AACACTCATT CCTGTTGAA 29

(2) INFORMATION FOR SEQ ID NO:71:

(i) SEQUENCE CHARACTERISTICS:
        (A) LENGTH: 798 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO ( i v ) ANTI-SENSE: NO ( x i ) SEQUENCE DESCRIPTION: SEQ ID NO:71:

| | | | | | | |
|---|---|---|---|---|---|---|
| GGCCGCAAAT | TCTATTTCAA | GGAGACAGTC | ATAATGAAAT | ACCTATTGCC | TACGGCAGCC | 60 |
| GCTGGATTGT | TATTACTCGC | TGCCCAACCA | GCCATGGCCC | AGGTGAAACT | GCTCGAGTCA | 120 |
| GGACCTGGCC | TCGTGAAACC | TTCTCAGTCT | CTGTCTCTCA | CCTGCTCTGT | CACTGACTAC | 180 |
| TCCATCACCA | GTGCTTATTA | CTGGAACTGG | ATCCGGCAGT | TTCCAGGAAA | CAAACTGGAA | 240 |
| TGGATGGGCT | ACATAAGCTA | CGACGGTGTC | AATAAGTATG | ATCCATCTCT | CAAGAATCGA | 300 |
| ATCTCCATCA | CTCGTGACAC | ATCTAACAAT | CAGTTTTTCC | AGAAGTTGAT | TTCTGTGACT | 360 |
| TCTGAGGACA | CAGGAACATA | TGACTGTTCA | AGAGGGACTA | GGGCCTCTGC | TATGGACTAC | 420 |
| TGGGGTCAAG | GAATTTCAGT | CACCGTCTCC | TCAGCCAAAA | CGACACCCCC | ATCTGTCTAT | 480 |
| CCACTGGCCC | CTGGATCTGC | TGCCCAAACT | AACTCCATGG | TGACCCTGGG | ATGCCTGGTC | 540 |
| AAGGGCTATT | TCCCTGAGCC | AGTGACAGTG | ACCTGGAACT | CTGGATCCCT | GTCCAGCGGT | 600 |
| GTGCACACCT | TCCCAGCTGT | CCTGCAGTCT | GACCTCTACA | CTCTGAGCAG | CTCAGTGACT | 660 |
| GTCCCCTCCA | GCCCTCGGCC | CAGCGAGACC | GTCACCTGCA | ACGTTGCCCA | CCCGGCCAGC | 720 |
| AGCACCAAGG | TGGACAAGAA | AATTGTGCCC | AGGGATTGTA | CTAGTTACCC | GTACGACGTT | 780 |
| CCGGACTACG | GTTCTTAA | | | | | 798 |

( 2 ) INFORMATION FOR SEQ ID NO:72:

( i ) SEQUENCE CHARACTERISTICS:
        ( A ) LENGTH: 194 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:72:

| | | | | | | |
|---|---|---|---|---|---|---|
| TGAATTCTAA | ACTAGTCGCC | AAGGAGACAG | TCATAATGAA | ATACCTATTG | CCTACGGCAG | 60 |
| CCGCTGGATT | GTTACTCGCT | GCCCAACCAG | CCATGGCCGA | GCTCCAGATG | ACCCAGTCTC | 120 |
| CAGCCTCCCT | ATCTGCATCT | GTGGGAGAAA | CTGTCACCAT | CACATGTCGA | TCAAGTGAGA | 180 |
| ATATTACAAT | TACT | | | | | 194 |

( 2 ) INFORMATION FOR SEQ ID NO:73:

( i ) SEQUENCE CHARACTERISTICS:
        ( A ) LENGTH: 333 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:73:

| | | | | | | |
|---|---|---|---|---|---|---|
| CTGATGCTGC | ACCAACTGTA | TCCATCTTCC | CACCATCCAG | TGAGCAGTTA | ACATCTGGAG | 60 |
| GTGCCTCAGT | CGTGTGCTTC | TTGAACAACT | TCTACCCCAA | AGACTACAAT | GTCAAGGGA | 120 |
| AGATTGATGG | CAGTGAACGA | CAAAATGGCG | TCCTGAACAG | TTGGACTGAT | CAGGACAGCA | 180 |

| | | | | | |
|---|---|---|---|---|---|
| AAGACAGCAC | CTACAGCATG | AGCAGCACCC | TCACGTTGAC | CAAGGACGAG | TATGAACGAC 240 |
| ATAACAGCTA | TACCTGTGAT | GCCACTCACA | AGACATCAAC | TTCACCCATT | GTCAAGAGCT 300 |
| TCAACAGGAA | TGAGTGTTAA | TTCTAGACGG | CGC | | 333 |

( 2 ) INFORMATION FOR SEQ ID NO:74:

( i ) SEQUENCE CHARACTERISTICS:
    ( A ) LENGTH: 150 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:74:

| | | | | | |
|---|---|---|---|---|---|
| GCTGAGGGTG | ACGATCCGC | AAAAGCGGCC | TTTAACTCCC | TGCAAGCCTC | AGCGACCGAA 60 |
| TATATCGGTT | ATGCGTGGGC | GATGGTTGTT | GTCATTGTCG | GCGCAACTAT | CGGTATCAAG 120 |
| CTGTTTAAGA | AATTCACCTC | GAAAGCAAGC | | | 150 |

( 2 ) INFORMATION FOR SEQ ID NO:75:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:75:

GTGCCCAGGG ATTGTACTAG TGCTGAGGGT GACGAT            36

( 2 ) INFORMATION FOR SEQ ID NO:76:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:76:

ACTCGAATTC TATCAGCTTG CTTTCGAGGT GAA             33

( 2 ) INFORMATION FOR SEQ ID NO:77:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:77:

AGGTCCAGCT TCTCGAGTCT GG    22

( 2 ) INFORMATION FOR SEQ ID NO:78:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:78:

GTCACCCTCA GCACTAGTAC AATCCCTGGG CAC    33

( 2 ) INFORMATION FOR SEQ ID NO:79:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:79:

GAGACGACTA GTGGTGGCGG TGGCTCTCCA TTCGTTTGTG AATATCAA    48

( 2 ) INFORMATION FOR SEQ ID NO:80:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:80:

TTACTAGCTA GCATAATAAC GGAATACCCA AAAGAACTGG    40

( 2 ) INFORMATION FOR SEQ ID NO:81:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:81:

TATGCTAGCT AGTAACACGA CAGGTTTCCC GACTGG                                                                      36

( 2 ) INFORMATION FOR SEQ ID NO:82:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:82:

ACCGAGCTCG AATTCGTAAT CATGGTC                                                                                27

( 2 ) INFORMATION FOR SEQ ID NO:83:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:83:

AGCTGTTGAA TTCGTGAAAT TGTTATCCGC T                                                                           31

( 2 ) INFORMATION FOR SEQ ID NO:84:

( i ) SEQUENCE CHARACTERISTICS:
        ( A ) LENGTH: 186 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:84:

GTGCCCAGGG ATTGTACTAG TGCTGAGGGT GACGATCCCG CAAAAGCGGC CTTTAACTCC                                             60

CTGCAAGCCT CAGCGACCGA ATATATCGGT TATGCGTGGG CGATGGTTGT TGTCATTGTC                                            120

GGCGCAACTA TCGGTATCAA GCTGTTTAAG AAATTCACCT CGAAAGCAAG CTGATAGAAT                                            180

TCGAGT                                                                                                      186

( 2 ) INFORMATION FOR SEQ ID NO:85:

( i ) SEQUENCE CHARACTERISTICS:
        ( A ) LENGTH: 666 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:85:

| | | | | | | |
|---|---|---|---|---|---|---|
| CCATTCGTTT | GTGAATATCA | AGGCCAAGGC | CAATCGTCTG | ACCTGCCTCA | ACCTCCTGTC | 60 |
| AATGCTGGCG | GCGGCTCTGG | TGGTGGTTCT | GGTGGCGGCT | CTGAGGGTGG | TGGCTCTGAG | 120 |
| GGTGGCGGTT | CTGAGGGTGG | CGGCTCTGAG | GGAGGCGGTT | CCGGTGGTGG | CTCTGGTTCC | 180 |
| GGTGATTTTG | ATTATGAAAA | GATGGCAAAC | GCTAATAAGG | GGGCTATGAC | CGAAAATGCC | 240 |
| GATGAAAACG | CGCTACAGTC | TGACGCTAAA | GGCAAACTTG | ATTCTGTCGC | TACTGATTAC | 300 |
| GGTGCTGCTA | TCGATGGTTT | CATTGGTGAC | GTTTCCGGCC | TTGCTAATGG | TAATGGTGCT | 360 |
| ACTGGTGATT | TTGCTGGCTC | TAATTCCCAA | ATGGCTCAAG | TCGGTGACGG | TGATAATTCA | 420 |
| CCTTTAATGA | ATAATTTCCG | TCAATATTTA | CCTTCCCTCC | CTCAATCGGT | TGAATGTCGC | 480 |
| CCTTTTGTCT | TTAGCGCTGG | TAAACCATAT | GAATTTTCTA | TTGATTGTGA | CAAAATAAAC | 540 |
| TTATTCGGTG | TCTTTGCGTT | TCTTTTATAT | GTTGCCACCT | TTATGTATGT | ATTTTCTACG | 600 |
| TTTGCTAACA | TACTGCGTAA | TAAGGAGTCT | TAATCATGCC | AGTTCTTTTG | GGTATTCCGT | 660 |
| TATTAT | | | | | | 666 |

( 2 ) INFORMATION FOR SEQ ID NO:86:

( i ) SEQUENCE CHARACTERISTICS:
        ( A ) LENGTH: 708 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:86:

| | | | | | | |
|---|---|---|---|---|---|---|
| GAGACGACTA | GTGGTGGCGG | TGGCTCTCCA | TTCGTTTGTG | AATATCAAGG | CCAAGGCCAA | 60 |
| TCGTCTGACC | TGCCTCAACC | TCCTGTCAAT | GCTGGCGGCG | GCTCTGGTGG | TGGTTCTGGT | 120 |
| GGCGGCTCTG | AGGGTGGTGG | CTCTGAGGGT | GGCGGTTCTG | AGGGTGGCGG | CTCTGAGGGA | 180 |
| GGCGGTTCCG | GTGGTGGCTC | TGGTTCCGGT | GATTTTGATT | ATGAAAGAT | GGCAAACGCT | 240 |
| AATAAGGGGG | CTATGACCGA | AAATGCCGAT | GAAACGCGC | TACAGTCTGA | CGCTAAAGGC | 300 |
| AAACTTGATT | CTGTCGCTAC | TGATTACGGT | GCTGCTATCG | ATGGTTTCAT | TGGTGACGTT | 360 |
| TCCGGCCTTG | CTAATGGTAA | TGGTGCTACT | GGTGATTTTG | CTGGCTCTAA | TTCCCAAATG | 420 |
| GCTCAAGTCG | GTGACGGTGA | TAATTCACCT | TTAATGAATA | ATTTCCGTCA | ATATTTACCT | 480 |
| TCCCTCCCTC | AATCGGTTGA | ATGTCGCCCT | TTTGTCTTTA | GCGCTGGTAA | ACCATATGAA | 540 |
| TTTTCTATTG | ATTGTGACAA | AATAAACTTA | TTCCGTGGTG | TCTTTGCGTT | TCTTTTATAT | 600 |
| GTTGCCACCT | TTATGTATGT | ATTTTCTACG | TTTGCTAACA | TACTGCGTAA | TAAGGAGTCT | 660 |
| TAATCATGCC | AGTTCTTTTG | GGTATTCCGT | TATTATGCTA | GCTAGTAA | | 708 |

( 2 ) INFORMATION FOR SEQ ID NO:87:

( i ) SEQUENCE CHARACTERISTICS:
        ( A ) LENGTH: 201 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:87:

| | | | | | | |
|---|---|---|---|---|---|---|
| TATGCTAGCT | AGTAACACGA | CAGGTTTCCC | GACTGGAAAG | CGGGCAGTGA | GCGCAACGCA | 60 |
| ATTAATGTGA | GTTAGCTCAC | TCATTAGGCA | CCCCAGGCTT | TACACTTTAT | GCTTCCGGCT | 120 |
| CGTATGTTGT | GTGGAATTGT | GAGCGGATAA | CAATTTCACA | CAGGAAACAG | CTATGACCAT | 180 |
| GATTACGAAT | TCGAGCTCGG | T | | | | 201 |

( 2 ) INFORMATION FOR SEQ ID NO:88:

( i ) SEQUENCE CHARACTERISTICS:
        ( A ) LENGTH: 830 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:88:

| | | | | | | |
|---|---|---|---|---|---|---|
| AGGTCCAGCT | TCTCGAGTCT | GGACCTGGCC | TCGTGAAACC | TTCTCAGTCT | CTGTCTCTCA | 60 |
| CCTGCTCTGT | CACTGACTAC | TCCATCACCA | GTGCTTATTA | CTGGAACTGG | ATCCGGCAGT | 120 |
| TTCCAGGAAA | CAAACTGGAA | TGGATGGGCT | ACATAAGCTA | CGACGGTGTC | AATAAGTATG | 180 |
| ATCCATCTCT | CAAGAATCGA | ATCTCCATCA | CTCGTGACAC | ATCTAACAAT | CAGTTTTTCC | 240 |
| AGAAGTTGAT | TTCTGTGACT | TCTGAGGACA | CAGGAACATA | TGACTGTTCA | AGAGGGACTA | 300 |
| GGGCCTCTGC | TATGGACTAC | TGGGGTCAAG | GAATTTCAGT | CACCGTCTCC | TCAGCCAAAA | 360 |
| CGACACCCCC | ATCTGTCTAT | CCACTGGCCC | CTGGATCTGC | TGCCCAAACT | AACTCCATGG | 420 |
| TGACCCTGGG | ATGCCTGGTC | AAGGGCTATT | TCCCTGAGCC | AGTGACAGTG | ACCTGGAACT | 480 |
| CTGGATCCCT | GTCCAGCGGT | GTGCACACCT | TCCCAGCTGT | CCTGCAGTCT | GACCTCTACA | 540 |
| CTCTGAGCAG | CTCAGTGACT | GTCCCCTCCA | GCCCTCGGCC | CAGCGAGACC | GTCACCTGCA | 600 |
| ACGTTGCCCA | CCCGGCCAGC | AGCACCAAGG | TGGACAAGAA | AATTGTGCCC | AGGGATTGTA | 660 |
| CTAGTGCTGA | GGGTGACGAT | CCCGCAAAAG | CGGCCTTTAA | CTCCCTGCAA | GCCTCAGCGA | 720 |
| CCGAATATAT | CGGTTATGCG | TGGGCGATGG | TTGTTGTCAT | TGTCGGCGCA | ACTATCGGTA | 780 |
| TCAAGCTGTT | TAAGAAATTC | ACCTCGAAAG | CAAGCTGATA | GAATTCGAGT | | 830 |

( 2 ) INFORMATION FOR SEQ ID NO:89:

( i ) SEQUENCE CHARACTERISTICS:
        ( A ) LENGTH: 260 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:89:

| | | | | | | |
|---|---|---|---|---|---|---|
| ATGAAATACC | TATTGCCTAC | GGCAGCCGCT | GGATTGTTAT | TACTCGCTGC | CCAACCAGCC | 60 |
| ATGGCCCAGG | TGAAACTGCT | CGAGATTTCT | AGACTAGTGC | TGAGGGTGAC | GATCCCGCAA | 120 |
| AAGCGGCCTT | TAACTCCCTG | CAAGCCTCAG | CGACCGAATA | TATCGGTTAT | GCGTGGGCGA | 180 |

TGGTTGTTGT CATTGTCGGC GCAACTATCG GTATCAAGCT GTTTAAGAAA TTCACCTCGA         240

AAGCAAGCTG ATAGAATTCG                                                    260

( 2 ) INFORMATION FOR SEQ ID NO:90:

( i ) SEQUENCE CHARACTERISTICS:
        ( A ) LENGTH: 461 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:90:

GTACGCGCCC TGTAGCGGCG CATTAAGCGC GGCGGGTGTG GTGGTTACGC GCAGCGTGAC         60

CGCTACACTT GCCAGCGCCC TAGCGCCCGC TCCTTTTGCT TTCTTCCCTT CCTTTCTCGC         120

CACGTTCGCC GGCTTTCCCC GTCAAGCTCT AAATCGGGGG CTCCCTTTAG GGTTCCGATT         180

TAGTGCTTTA CGGCACCTCG ACCCCAAAAA ACTTGATTAG GGTGATGGTT CACGTAGTGG         240

GCCATCGCCC TGATAGACGG TTTTTCGCCC TTTGACGTTG GAGTCCACGT TCTTTAATAG         300

TGGACTCTTG TTCCAAACTG GAACAACACT CAACCCTATC TCGGTCTATT CTTTTGATTT         360

ATAAGGGATT TTGCCGATTT CGGCCTATTG GTTAAAAAAT GAGCTGATTT AACAAAAATT         420

TAACGCGAAT TTTAACAAAA TATTAACGTT TACAATTTAA A                            461

( 2 ) INFORMATION FOR SEQ ID NO:91:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:91:

Glu Gly Gly Gly Ser Glu Gly Gly Gly Ser Glu Gly Gly Gly Ser Glu
1               5                   10                  15

Gly Gly Gly Ser
            20

( 2 ) INFORMATION FOR SEQ ID NO:92:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:92:

CAGCTGCTCG AGCGGACACC AGAAATGCCT GTT                                     33

( 2 ) INFORMATION FOR SEQ ID NO:93:

( i ) SEQUENCE CHARACTERISTICS:
   ( A ) LENGTH: 33 base pairs
   ( B ) TYPE: nucleic acid
   ( C ) STRANDEDNESS: single
   ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:93:

AGGCTTACTA GTTTTCAGCC CCAGAGCGGC TTT        33

( 2 ) INFORMATION FOR SEQ ID NO:94:

( i ) SEQUENCE CHARACTERISTICS:
      ( A ) LENGTH: 63 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:94:

CTAGTGAGGG TGGTGGCTCT GAGGGTGGCG GTTCTGAGGG TGGCGGTTCT GAGGGTGGCG        60

GTT        63

( 2 ) INFORMATION FOR SEQ ID NO:95:

( i ) SEQUENCE CHARACTERISTICS:
      ( A ) LENGTH: 51 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:95:

GCCGCGTCTA GACCTAGGGG TGGCGGAGGT ACACCAGAAA TGCCTGTTCT G        51

( 2 ) INFORMATION FOR SEQ ID NO:96:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:96:

AGGCTTACTA GTTTTCAGCC CCAGAGCGGC TTT        33

( 2 ) INFORMATION FOR SEQ ID NO:97:

( i ) SEQUENCE CHARACTERISTICS:
      ( A ) LENGTH: 19 base pairs (B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:97:

TCCACTAGTT AGGGTGGTG                                                                 19

PHAGEMIDS COEXPRESSING A SURFACE RECEPTOR AND A SURFACE HETEROLOGOUS PROTEIN

This application is a 371 of PCT/US93/08364, filed Sep. 3, 1993, and a continuation-in-part of Ser. No. 07/941,369, filed Sep. 4, 1992, now abandoned.

This invention was made with government support under Contract No. CA56483 by the National Institutes of Health. The government has certain rights in the invention.

TECHNICAL FIELD

The present invention relates to cloning vectors and methods for producing a library of DNA molecules capable of expressing a heterodimeric receptor and a second dimeric heterologous indicator fusion polypeptide on the surface of a filamentous phage particle.

BACKGROUND

Filamentous bacteriophages are a group of related viruses that infect bacteria. They are termed filamentous because they are long and thin particles comprised of an elongated capsule that envelopes the deoxyribonucleic acid (DNA) that forms the bacteriophage genome. The F pili filamentous bacteriophage (Ff phage) infect only gram-negative bacteria by specifically adsorbing to the tip of F pili, and include fd, f1 and M13.

The mature capsule of Ff phage is comprised of a coat of five phage-encoded gene products: cpVIII, the major coat protein product of gene VIII that forms the bulk of the capsule; and four minor coat proteins, cpIII and cpIV at one end of the capsule and cpVII and cpIX at the other end of the capsule. The length of the capsule is formed by 2500 to 3000 copies of cpVIII in an ordered helix array that forms the characteristic filament structure. About five copies each of the minor coat proteins are present at the ends of the capsule. The gene III-encoded protein (cpIII) is typically present in 4 to 6 copies at one end of the capsule and serves as the receptor for binding of the phage to its bacterial host in the initial phase of infection. For detailed reviews of Ff phage structure, see Rasched et al., *Microbiol. Rev.*, 50:401–427 (1986); and Model et al., in "The Bacteriophages, Volume 2", R. Calendar, Ed., Plenum Press, pp. 375–456 (1988).

The assembly of a Ff phage particle involves highly complex mechanics. No phage particles are assembled within a host cell; rather, they are assembled during extrusion of the viral genome through the host cell's membrane. Prior to extrusion, the major coat protein cpVIII and the minor coat protein cpIII are synthesized and transported to the host cell's membrane. Both cpVIII and cpIII are anchored in the host cell membrane prior to their incorporation into the mature particle. In addition, the viral genome is produced and coated with cpV protein. During the extrusion process, cpV-coated genomic DNA is stripped of the cpV coat and simultaneously re-coated with the mature coat proteins. The assembly mechanisms that control transferral of these proteins from the membrane to the particle is not presently known.

Both cpIII and cpVIII proteins include two domains that provide signals for assembly of the mature phage particle. The first domain is a secretion signal that directs the newly synthesized protein to the host cell membrane. The secretion signal is located at the amino terminus of the polypeptide and targets the polypeptide at least to the cell membrane. The second domain is a membrane anchor domain that provides signals for association with the host cell membrane and for association with the phage particle during assembly. This second signal for both cpVIII and cpIII comprises at least a hydrophobic region for spanning the membrane.

cpVIII has been extensively studied as a model membrane protein because it can integrate into lipid bilayers such as the cell membrane in an asymmetric orientation with the acidic amino terminus toward the outside and the basic carboxy terminus toward the 100 inside of the membrane. The mature protein is about 50 amino acid residues in length of which 11 residues provide the carboxy terminus, 19 residues provide the hydrophobic transmembrane region, and the remaining residues comprise the amino terminus. Considerable research has been done on the secretion signal region of cpVIII to advance the study of membrane protein synthesis and targeting to membranes. However, little is known about the changes that are tolerated in the structure of the cpVIII membrane anchor region that would allow for assembly of phage particles.

Manipulation of the sequence of cpIII shows that the C-terminal 23 amino acid residue stretch of hydrophobic amino acids normally responsible for a membrane anchor function can be altered in a variety of ways and retain the capacity to associate with membranes. However, those anchor-modified cpIII proteins lost their ability to genetically complement gene III mutants indicating that the requirements of a membrane anchor for functional assembly have not been elucidated.

Ff phage-based expression vectors have been described in which the entire cpIII amino acid residue sequence was modified by insertion of short polypeptide "epitopes" [Parmely et al., *Gene*, 73:305–318 (1988); and Cwirla et al., *Proc. Natl. Acad. Sci. USA*, 87:6378–6382 (1990)] or an amino acid residue sequence defining a single chain antibody domain. McCafferty et al., *Science*, 348:552–554 (1990). These hybrid proteins were synthesized and assembled onto phage particles in amounts of about 5 copies per particle, a density at which normal cpIII is usually found.

Numerous other fusion polypeptides have been expressed on the surface of a filamentous phage particle by fusion to a coat protein membrane anchor, including model polypeptides in cpVIII [Il'ichev et al, *Molekulvarnava Biologiva*, 24:530–535 (1990)], and functional bovine pancreatic trypsin inhibitor (BPTI) fused to mature cpVIII [Markland et al, *Gene*, 109:13–19 (1991)]. In addition, enzymatically functional alkaline phosphatase has been expressed on the surface of filamentous phage particles as a fusion protein with cpIII. McCafferty et al, *Protein Eng.*, 4:955–961 (1991). Genes have also been constructed for expressing a bifunctional molecule in which a single-chain antigen binding protein is fused to a bacterial alkaline phosphatase protein, the latter of which allows for the detection of the bound single-chain binding protein when attached to target antigens. See, Wels et al., *Bio/Technology*, 10:1128–1132 (1992).

Recently, a surface-integration technology has been described for expressing a heterodimeric recombinant gene product such as an antibody molecule on the surface of a filamentous phage containing recombinant genes. The technology uses a filamentous phage coat protein membrane anchor domain as a means for linking gene-product and gene during the assembly stage of filamentous phage replication, and has been used for the cloning and expression of antibodies from combinatorial libraries. Kang et al., *Proc. Natl. Acad. Sci., USA*, 88:4363–4366 (1991).

Combinatorial libraries of antibodies have been produced using both the cpVIII membrane anchor [Kang et al., supra, (1991) and the cpIII membrane anchor. Barbas et al, *Proc. Natl. Acad. Sci., USA,* 88:7978–7982 (1991). Human combinatorial antibody libraries have been produced that immunoreact with hepatitis B virus surface antigens using the technology. Zebedee et al, *Proc. Natl. Acad. Sci., USA,* 89:3175–3179 (1992). The diversity of a filamentous phage-based combinatorial antibody library has been increased by shuffling of the heavy and light chain genes [Kang et al, *Proc. Natl. Acad. Sci., USA,* 88:11120–11123, (1991)], by altering the CDR3 regions of the cloned heavy chain genes of the library [Barbas et al, *Proc. Natl. Acad. Sci., USA,* 89:4457–4461, (1992)], and by introducing random mutations into the library by error-prone polymerase chain reactions (PCR) [Gram et al, *Proc. Natl. Acad. Sci., USA,* 89:3576–3580, (1992)]. In addition, single-chain Fv fragments have been displayed on the surface of phage as described by Marks et al., *J. Mol. Biol.,* 222:581–597 (1991).

Because these technologies involve the manipulation of large libraries containing $10^6$ to $10^9$ different members, there continues to be a need for improved methods to screen the library for the desired binding specificities.

Typical screening procedures involve the use of secondary antibodies directed against the surface-exposed antibody on the phage particle. The use of a secondary antibody can introduce non-specific artifacts in the screening procedure, and thereby alter the sensitivity of a screening procedure to identify phage particles having an expressed antibody of desired immunospecificity.

BRIEF DESCRIPTION OF THE INVENTION

It has now been discovered that different heterologous polypeptides can be engineered onto the surface of a single filamentous phage particle using either cpIII or cpVIII coat protein membrane anchors. Thus, a heterodimeric receptor can be expressed on the surface of the phage particle, together with a second heterologous polypeptide, such as an indicator polypeptide, on the surface of the phage particle.

The second heterologous polypeptide is present in the form of a fusion polypeptide containing a membrane anchor of the present invention. A preferred embodiment is a dimer having two heterologous polypeptide subunits. A preferred dimer of heterologous polypeptides is a dimer having a first subunit of the dimer comprising a heterologous polypeptide fused to a first filamentous phage coat protein membrane anchor and a second subunit that is a soluble non-anchored polypeptide. The anchored heterologous polypeptide is directly fused to the coat protein membrane anchor. A further preferred embodiment is the presence of a linker polypeptide fusing the heterologous polypeptide to the coat protein membrane anchor.

The second indicator fusion polypeptide can be utilized to provide an indicating means to the phage particle, such as where the polypeptide provides a detectable signal. The presence of an indicating means on a phage particle provides a system for screening phage libraries without the need for use of a secondary antibody.

Thus, the present invention contemplates a filamentous phage comprising a) a heterologous polypeptide fused to a first filamentous phage coat protein membrane anchor; and b) a heterodimeric receptor comprised of first and second receptor polypeptides wherein one of said receptor polypeptides is fused to a second filamentous phage coat protein membrane anchor. In preferred embodiments, the phage further comprises a dimer having a first subunit of the dimer comprising a heterologous polypeptide fused to a first filamentous phage coat protein membrane anchor and a second subunit of the dimer that is soluble. A preferred first phage coat protein is cpVIII and second phage coat protein is cpIII. A preferred heterologous polypeptide is fused to the coat protein membrane anchor through a linker polypeptide. A preferred linker peptide has the amino acid residue sequence in SEQ ID NO:91. In preferred embodiments, the first and second subunits of the dimer are both the same indicator polypeptide, preferably alkaline phosphatase.

Also described are libraries of filamentous phage particles of this invention, and methods of making and using the phage particles of this invention.

BRIEF DESCRIPTION OF THE DRAWINGS

In the drawings forming a portion of this disclosure:

FIG. 1 illustrates the sequence of the double-stranded synthetic DNA inserted into Lambda Zap to produce a Lambda Hc2 expression vector. The preparation of the double-stranded synthetic DNA insert is described in Example 1a(ii). The various features required for this vector to express the $V_H$-coding DNA homologs include the Shine-Dalgarno ribosome binding site, a leader sequence to direct the expressed protein to the periplasm as described by Mouva et al., *J. Biol. Chem.,* 255:27, 1980, and various restriction enzyme sites used to operatively link the $V_H$ homologs to the expression vector. The $V_H$ expression vector sequence also contains a short nucleic acid sequence that codes for amino acids typically found in variable regions heavy chain ($V_H$ backbone). This $V_H$ backbone is just upstream and in the proper reading as the $V_H$ DNA homologs that are operatively linked into the Xho I and Spe I cloning sites. The sequences of the top and bottom strands of the double-stranded synthetic DNA insert are listed respectively as SEQ ID NO:1 and SEQ ID NO:2. The synthetic DNA insert is directionally ligated into Lambda Zap II digested with the restriction enzymes Not 1 and Xho I to form Lambda Hc2 expression vector.

FIG. 3 illustrates the sequence of the double-stranded synthetic DNA inserted into Lambda Zap to produce a Lambda Lc2 expression vector. The various features required for this vector to express the $V_L$-coding DNA homologs are described in FIG. 1. The $V_L$-coding DNA homologs are operatively linked into the Lc2 sequence at the Sac I and Xho I restriction sites. The sequences of the top and bottom strands of the double-stranded synthetic DNA insert are listed respectively as SEQ ID NO:3 and SEQ ID NO:4. The synthetic DNA insert is directionally ligated into Lambda Zap II digested with the restriction enzymes Sac I and Not I to form Lambda Lc2 expression vector.

FIG. 13 (Parts A–D) illustrates attachment of a bacterial alkaline phosphatase (BAP) dimer to the phage coat protein. FIG. 13A shows that each half of the dimer is fused directly to coat protein 8 (g8p); FIG. 13B shown that each half of the dimer is attached to g8p by a flexible linker; FIG. 13C shows that one half of the dimer is fused to g8p, while the other half is free; and FIG. 13*d* shows that one half of the dimer is attached to g8p by a linker, while the other half is free.

FIG. 14 (Parts A–C) illustrates the expression vectors used test incorporation of BAP on phage. FIG. 14A illustrates pPho8B that produces BAP-g8p, has a p15A origin of replication, and a chloramphenicol resistance marker; FIG. 14B shows pPhoL8B that is identical to pPho8B except for the insertion of a sequence coding for the $(EGGGS)_4$ (SEQ ID NO:91) linker; and FIG. 14C shows vector pPhoC that produces free BAP, has a colE1 origin of replication, and a b-lactamase marker. Abbreviations: tac, tac promoter; lac, lac promoter; PelB, PelB leader sequence; rbs, ribosome binding site; bla, b-lactamase gene; PhoA, coding region for mature *E. coli* BAP; gVIII, coding region for mature phage coat protein g8p.

DETAILED DESCRIPTION OF THE INVENTION

A. Definitions

Figure 2:
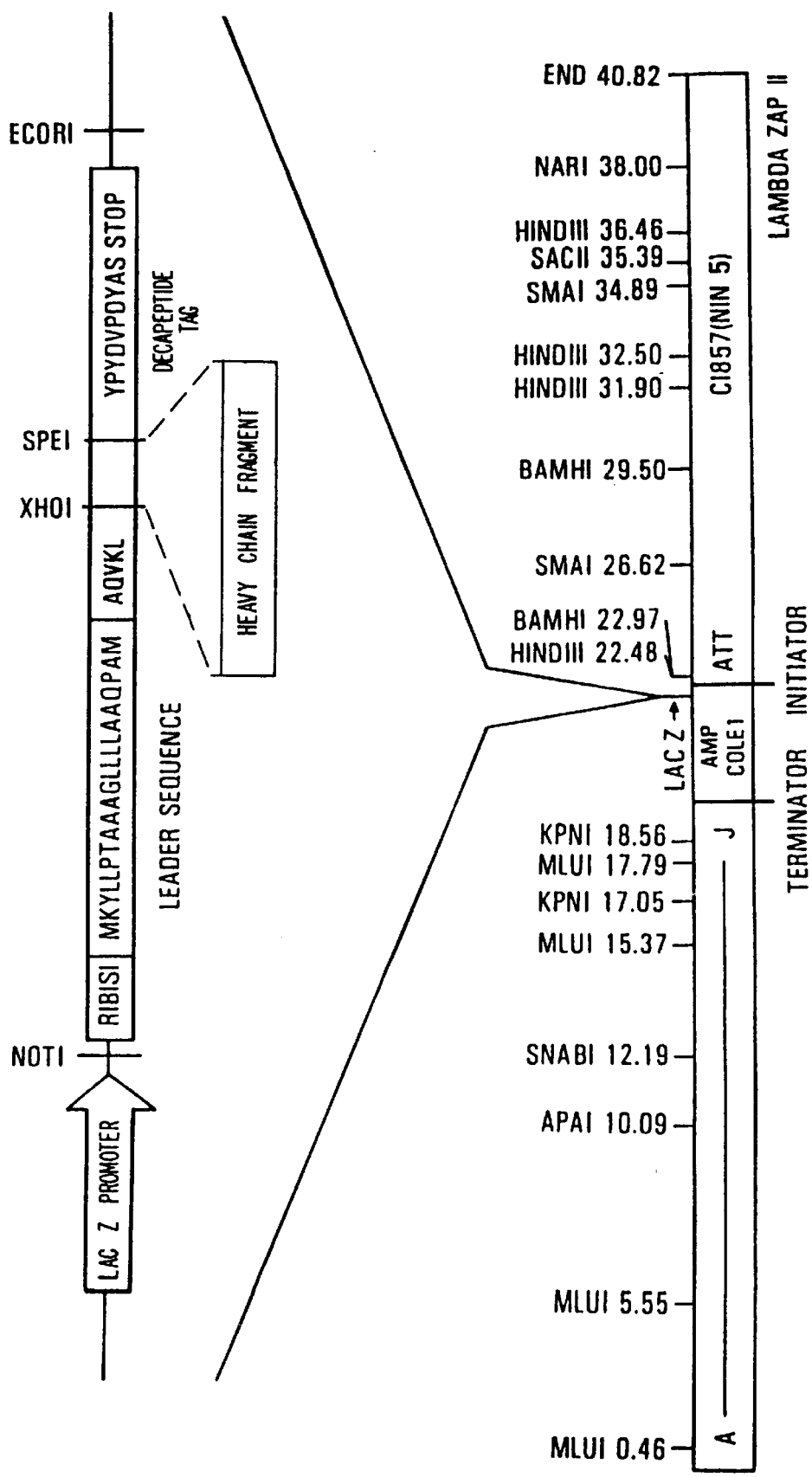
FIG. 2 illustrates the major features of the bacterial expression vector Lambda Hc2 ($V_H$ expression vector). The synthetic DNA sequence from FIG. 3 is shown at the top along with the LacZ promoter from Lambda Zap II. The orientation of the insert in Lambda Zap II is shown. The $V_H$ DNA homologs are inserted into the Xho I and Spe I cloning sites. The read through transcription produces the decapeptide epitope (tag) that is located just 3' of the cloning site.

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.,* 243:3552–59 (1969) and adopted at 37 C.F.R. 1.822(b)(2)), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences represented herein by formulae have a left-to-right orientation in the conventional direction of amino terminus to carboxy terminus. In addition, the phrase "amino acid residue" is broadly defined to include the amino acids listed in the Table of Correspondence and modified and unusual amino acids, such as those listed in 37 CFR 1.822(b)(4), and incorporated herein by reference. Furthermore, it should be noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

Recombinant DNA (rDNA) molecule: A DNA molecule produced by operatively linking two DNA segments. Thus, a recombinant DNA molecule is a hybrid DNA molecule comprising at least two nucleotide sequences not normally found together in nature. rDNA's not having a common biological origin, i.e., evolutionarily different, are said to be "heterologous".

Vector: A rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors". Particularly important vectors allow cloning of cDNA (complementary DNA) from mRNAs produced using reverse transcriptase.

Receptor: A receptor is a molecule, such as a protein, glycoprotein and the like, that can specifically (non-randomly) bind to another molecule.

Antibody: The term antibody in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', F(ab')$_2$ and F(v).

Antibody Combining Site: An antibody combining site is that structural portion of an antibody molecule comprised of a heavy and light chain variable and hypervariable regions that specifically binds (immunoreacts with) an antigen. The term immunoreact in its various forms means specific binding between an antigenic determinant-containing molecule and a molecule containing an antibody combining site such as a whole antibody molecule or a portion thereof.

Fusion Polypeptide: A polypeptide comprised of at least two polypeptides and a linking sequence to operatively link the two polypeptides into one continuous polypeptide. The two polypeptides linked in a fusion polypeptide are typically derived from two independent sources, and therefore a fusion polypeptide comprises two linked polypeptides not normally found linked in nature.

Upstream: In the direction opposite to the direction of DNA transcription, and therefore going from 5' to 3' on the non-coding strand, or 3' to 5' on the mRNA.

Downstream: Further along a DNA sequence in the direction of sequence transcription or read out, that is traveling in a 3'- to 5'-direction along the non-coding strand of the DNA or 5'- to 3'-direction along the RNA transcript.

Cistron: A sequence of nucleotides in a DNA molecule coding for an amino acid residue sequence and including upstream and downstream DNA expression control elements.

Leader Polypeptide: A short length of amino acid sequence at the amino end of a polypeptide, which carries or directs the polypeptide through the inner membrane and so ensures its eventual secretion into the periplasmic space and perhaps beyond. The leader sequence peptide is commonly removed before the polypeptide becomes active.

Reading Frame: A particular sequence of contiguous nucleotide triplets (codons) employed in translation. The reading frame depends on the location of the translation initiation codon.

Dimer: A polymer formed from two molecules of a monomer; also a molecule consisting of two identical subunits, but sometimes it consists of a supramolecular structure consisting of two distinct subunits.

B. Filamentous Phage

The present invention contemplates a filamentous phage comprising a matrix of proteins including a heterodimeric receptor comprised of first and second polypeptides surface-integrated into the matrix via a filamentous phage membrane anchor domain that is fused to at least one of the first or second polypeptides. Preferably, the matrix is encapsulating a genome encoding the first and second polypeptides that are capable of forming the heterodimeric receptor. The heterodimeric receptor has the capacity to bind ligand and therefor is referred to as a ligand-binding heterodimeric receptor.

In addition, the phage further contains a second fusion protein surface-integrated into the matrix via a filamentous phage membrane anchor domain, which is a polypeptide heterologous to filamentous phage, i.e., a heterologous fusion protein. Thus, in one embodiment, a heterologous polypeptide is attached to the phage membrane through an anchor domain coat protein. In a preferred embodiment, the heterologous fusion protein is provided in the structure of a dimer composed of first and second polypeptide subunits such that a first heterologous polypeptide subunit is fused to a first filamentous phage coat protein membrane anchor and a second heterologous polypeptide subunit is attached to the first subunit, thereby forming a dimer of heterologous polypeptides. To that end, the second heterologous polypeptide is in the form of a subunit monomer that is not a fusion protein with an anchor protein. Thus, the second heterologous polypeptide subunit is a soluble free monomer.

Stated differently, a filamentous phage of this invention comprises (1) a heterologous polypeptide fused to a first filamentous phage coat protein membrane anchor, and (2) a heterodimeric receptor comprised of first and second receptor polypeptides, wherein at least one of the receptor polypeptides is fused to a second filamentous phage coat protein membrane anchor. A preferred filamentous phage of this invention comprises (1) a dimer having a first heterologous polypeptide fused to a first filamentous phage coat protein membrane anchor forming a fusion protein, and having a second heterologous polypeptide, wherein the first heterologous polypeptide portion of the fusion protein binds with the second heterologous polypeptide subunit that is a free, soluble monomer, and (2) a heterodimeric receptor comprised of first and second receptor polypeptides, wherein at least one of the receptor polypeptides is fused to a second filamentous phage coat protein membrane anchor.

The heterodimeric receptor in a preferred embodiment is an epitope-binding complex. That is, a complex of first and second polypeptides capable of binding an epitope. Preferably, the first and second receptor polypeptides are antibody heavy chain and light chain polypeptides.

The first and second receptor polypeptides are capable of autogenous assembly into a functional epitope-binding complex (heterodimeric receptor), which is then expressed on the outer surface of the phage in a manner accessible to ligand, i.e., they are surface-integrated into the phage. Thus, an epitope-binding complex is typically present on the surface of a phage of this invention.

The heterologous polypeptide is also capable of expression on the surface of the phage. In one embodiment, the heterologous polypeptide is in the form of a fusion protein attached to a phage membrane coat protein. In a preferred embodiment, the first heterologous polypeptide segment of the fusion protein forms a dimer with a second heterologous polypeptide. Thus, the first and second heterologous polypeptides are capable of autogenous assembly into a functional heterologous polypeptide complex, forming a dimer from two monomers, the complex of which is then expressed on the outer surface by means of the phage anchor membrane protein attached to the first heterologous polypeptide subunit. Thus, the heterologous polypeptides and dimers thereof are expressed on the surface of the phage in a manner accessible to allow for function, i.e., they are surface-integrated into the phage. Thus, a heterologous polypeptide and a heterologous polypeptide dimer complex is typically present on the surface of a phage of this invention.

A dimer of this invention is defined as a polymer formed from two molecules of a monomer. In preferred embodiments, a dimer is a molecule consisting of two identical subunits. An alternative embodiment is a molecule having two distinct subunits. A dimer results from the expression of first and second receptor polypeptides resulting in the formation of a heterodimeric receptor. A separate and distinct dimer for use in this invention results from the joining of heterologous polypeptides monomers. Heterologous polypeptides are expressed in both non-anchored soluble monomeric forms and in attached monomeric forms, in which the latter is mediated through a phage membrane anchor coat protein.

A soluble heterologous polypeptide monomer is a monomer that is not anchored to a phage membrane coat protein, thus is referred to as non-anchored. Thus, by soluble, what is meant is non-anchored, unattached, free, non-fusion protein, non-fusion polypeptide, non-fastened, releasable from an anchored state by treatment of a dimer having intersubunits bonds, such as disulfide bonds between two cysteine residues, and the like. Therefore, the term soluble defines a heterologous polypeptide that is expressed from a vector of this invention without a membrane anchor that is free to bind to another soluble monomer or to an anchored monomer. In addition, the term soluble also defines a heterologous polypeptide that is released from a dimer by exposure of that dimer to a reducing agent, such as beta-mercaptoethanol, that results in the separation of the monomeric subunits.

The phage-anchored monomeric heterologous polypeptide is also referred to as a fusion protein. Dimers of heterologous polypeptides, in theory, can form from two soluble free monomeric forms, from a soluble free monomeric form with an attached monomeric form, or from two attached monomeric forms. Exemplary dimers for use in this invention are described below and in Example 8 and 9.

The surface integration of the heterologous fusion protein and the heterodimeric receptor is provided by the presence of the first and second filamentous phage coat protein membrane anchor domains fused thereto. Preferably, a coat protein is selected from the group consisting of cpIII and cpVIII. In a preferred embodiment described herein, the first and second anchors are not the same. That is, the heterologous fusion protein preferably contains a different coat protein membrane anchor than the heterodimeric receptor. This feature spaces the two functionalities apart onto different regions of the phage particle, which is advantageous in some applications. In a particularly preferred format the first membrane anchor (on the heterologous fusion protein) is cpVIII and the second membrane anchor (on the heterodimeric receptor) is cpIII.

A filamentous phage of this invention having two functionalities provides a variety of uses as described further herein.

In one particularly preferred embodiment, the phage particles are used as a structural linker between the heterodimeric receptor and the heterologous fusion polypeptide. That is, the phage matrix serves as a support for organized presentation of the two functions provided by (1) the heterologous fusion polypeptide and (2) the heterodimeric receptor. If the same membrane anchor is used for both functions, then the two functions are mixed on the phage particle. Where cpVIII is used for both, the majority of the matrix of the phage is coated with both functions randomly. Where cpIII is used for both, the functions are localized at one terminus of the phage particle.

More preferably, however, different membrane anchors are utilized, thereby separating the display of the heterologous polypeptide and the heterodimeric receptor. In particular, the invention contemplates placing the heterodimeric receptor at the terminus of the phage particle by fusion to cpIII in low copy number, and placing the heterologous polypeptide in high copy number throughout the matrix of the phage particle by fusion to cpVIII.

In a preferred embodiment, the heterologous polypeptide is displayed on a membrane anchor through a linker polypeptide. In particular, a linker polypeptide is a sequence of amino acid residues that provides a spacer region between the heterologous polypeptide and the membrane anchor. More specifically, the linker joins the carboxy terminus of the heterologous polypeptide and the amino terminus of the membrane anchor. The linker, while providing a connection between the heterologous polypeptide and the membrane anchor coat protein, allows for the heterologous polypeptide to be positioned further away from the membrane anchor coat protein expressed on the surface of the phage thereby providing a more accessible polypeptide that is less subject to physical and spatial constraints. The presence of the linker protein in the heterologous fusion protein is particularly preferred in the formation of a dimer of this invention as described herein. The linker is preferably an amino acid residue sequence of 1 to 100 amino acid residues in length, more preferably 5 to 50 residues in length, and most preferably 20 residues in length.

An exemplary polypeptide linker for use in this invention is the repeating polypeptide Glu-Gly-Gly-Gly-Ser or EGGGS (SEQ ID NO:91, from amino acid residue positions 1–5). The use of the preferred linker in the heterologous polypeptide fusion proteins of this invention is described in Examples 5–9. Conservative amino acid substitutions of the linker polypeptide are also contemplated. Polypeptide linkers having alternative amino acid residue sequences that provide the preferred function are similarly contemplated for use in this invention.

In one embodiment the heterodimeric receptor provides a targeting function, by virtue of its ligand binding specificity, transporting the function associated with the heterologous polypeptide to the vicinity of the preselected ligand. The targeting of a specific function is useful in diagnostic settings where the heterologous polypeptide provides an indicating means, as described further herein, such as where the heterologous polypeptide is an indicating polypeptide.

Alternatively, the targeting of a functional activity can have therapeutic utility where the functional property being targeted is of therapeutic usefulness. Thus the heterologous polypeptide can be any therapeutically relevant protein, including proteases for degrading proteins, such as in blood clotting, superoxide dismutases for removing superoxide radicals, and the like. In this embodiment, the heterodimeric receptor is selected to provide targeting to the relevant tissue based on its preselected binding specificity. Thus, the second fusion heterologous polypeptide can be utilized to provide a functional activity to the surface of the phage independent of the binding capability provided by the presence of a heterodimeric receptor having a preselected binding specificity, i.e., a bifunctional phage particle. In this embodiment, the bifunctional phage has the capacity to be targeted to a ligand of interest based on the binding specificity, thereby delivering the second functionality to the vicinity of the preselected ligand.

In a particular indicating embodiment, the present phage particle is useful as a screening tool for manipulating combinatorial antibody libraries, as described more fully herein. The presence of a detectable functionality in the heterologous polypeptide, such as an enzyme or other biological activity, provides a means for detecting the presence of the phage particle, and therefore the presence of a particular linked heterodimeric binding specificity.

Thus, the present phage can have an indicating polypeptide as the heterologous polypeptide fused to the first membrane anchor. A particularly preferred indicating polypeptide is an enzyme such as alkaline phosphatase, peroxidase, glucose oxidase, and the like enzymes amenable to rapid and sensitive detection as is well known in the immunological arts.

In the embodiment of a dimer having heterologous polypeptide subunits joined together, the preferred alkaline phosphatase indicating polypeptide forms a dimer mediated through a disulfide bond between cysteine residues from separate monomeric subunits of alkaline phosphatase. Thus, two monomers, either in the anchored or soluble conformation, will naturally form a dimer through a disulfide bridge. A preferred dimer results from the joining of a soluble alkaline phosphatase monomer to an anchored alkaline phosphatase monomer. A particularly preferred dimer is formed between two alkaline phosphatase monomers wherein the one anchored subunit is attached to the coat protein via a linker polypeptide. Enzymatic activity of the monomeric forms of alkaline phosphatase indicator polypeptide is enhanced when they are present in a dimer, thereby providing for an enhanced indicator detection system for use in this invention. The enhanced enzymatic activity of dimeric forms of alkaline phosphatase is described in Examples 8 and 9.

The possible multiple forms of dimers that are attached to the phage surface are schematically diagrammed in FIGS. 13A–D. Dimers theoretically can result from the joining of two soluble monomers, from a soluble monomer and an anchored monomer, and from two anchored monomers. Phage produced in the presence of a plasmid system that provides for the expression of both soluble and anchored heterologous polypeptide monomers, therefore, could have a mixture of heterodimers and homodimers on their surface. Thus, even if the expression of the soluble monomeric form is insufficient, dimers conceivably can form between two anchored monomers. However, as described in Example 8, two alkaline phosphatase monomers anchored to coat protein 8 through a 20 amino acid linker polypeptide were unable to form dimers on the surface of phage.

The inability to form dimers may be the result of steric hindrance or limitations imposed on the phage extrusion process in *E. coli*. As discussed in Example 8, the larger the protein being expressed through a fusion protein anchor to a phage membrane coat protein, the few the number of copies of the fusion protein that are presented on the phage. Size of the fusion protein alone thus can create steric limitations. The preferred indicator polypeptide for use in this invention is a large protein, alkaline phosphatase that is approximately 90 kilodaltons. Alternatively, a kinetic limitation occurs from competition of wild type coat protein 8 and a fusion protein for incorporation into phage. Markland et al., *Gene*, 109:13–19 (1991), have shown that lowering the expression of the wild type coat protein 8 with respect to the expression of a fusion protein resulted in an increase of the total number of fusion proteins expressed on the surface of phage. Thus, the extrusion process for either steric or kinetic bases may not provide for expression of fusion proteins in sufficient proximity to one another to allow for the formation of a sufficient number of dimers that provide adequate indicator polypeptide function.

Other limitations to the formation of a preferred dimer of heterologous indicator polypeptides is the formation of dimers between anchored subunits on different phage. This process results in the formation of insoluble, useless phage aggregates. In addition, dimers can form between two non-anchored soluble indicator polypeptide subunits. However, as discussed in Example 8, the formation of these non-preferred homodimer pairs produced as a result of the vector expression systems is substantially reduced in comparison to the formation of heterodimer pairs formed from one anchored fusion protein and one non-anchored soluble polypeptide. As a result, the preferred dimer having an anchored heterologous polypeptide joined to a non-anchored soluble polypeptide is the more prevalent and functional dimerized structure.

Because the heterodimeric receptor is linked to the phage in a surface accessible manner, the phage can also be advantageously used as a solid-phase affinity sorbent. In preferred embodiments, the phage are linked, preferably removably linked, to a solid (aqueous insoluble) matrix such as agarose, cellulose, synthetic resins, polysaccharides and the like. An aqueous composition containing a ligand that binds to the receptor expressed by the phage is then passed through the column at a predetermined rate and under receptor-binding conditions to form a solid-phase receptor-ligand complex. The column is then washed to remove unbound material, leaving the ligand bound to the solid-phase phage. The ligand can then be removed and recovered by washing the column with a buffer that promotes dissociation of the receptor-ligand complex.

Alternatively, purified phage can be admixed with a aqueous solution containing the ligand to be affinity purified. The receptor/ligand binding reaction admixture thus formed is maintained for a time period and under binding conditions sufficient for a phage-linked receptor-ligand complex to form. The phage-bound ligand (ligand-bearing phage) are then separated and recovered from the unbound materials, such as by centrifugation, electrophoresis, precipitation, and the like.

Phage of this invention can be labeled when used in a diagnostic method of this invention. Preferred labels include radioactively labeled nucleic acids incorporated into the phage genome, or radioactively labeled amino acids incorporated into protein components of the phage particle. Preparation of labeled phage can be routinely prepared by growing phage as described herein, but including radiolabeled nucleotides or radiolabeled amino acids in the culture medium for incorporation into nucleic acids or polypeptides of the phage, respectively. Exemplary labels are $^3$H-thymidine or $^{35}$S-methionine. Other isotopic labels and other nucleotide or amino acid precursors are readily available to one skilled in the art. The labeled phage preferably contains sufficient label to be detectable in a ligand binding assay of this invention, i.e., the phage is detectably labeled.

C. Phage Libraries

The present invention also contemplates a library of filamentous phage particles in the form of a population of different filamentous phage particles of this invention.

Thus, a phage library is a population of filamentous phage, preferably f1, fd or M13 filamentous phage, wherein the phage have packaged inside the particle a rDNA expression vector of this invention, the rDNA is encapsulated in the phage particle by the matrix proteins of the phage.

Stated differently, a phage library contains a plurality of filamentous phage particles, each different phage particle containing at least one epitope-binding complex on its surface, and further containing the heterologous fusion polypeptide on its surface, as described herein.

A preferred library is comprised of phage particles containing DNA molecules that encode at least $10^6$, preferably $10^7$ and more preferably $10^{8-9}$ different heterodimeric receptors of this invention. By different is meant different fusion receptor polypeptides differing in amino acid residue sequence. Even higher library diversities are available when the methods of random combination or mutagenesis are utilized to increase library diversity as described by Kang et al, *Proc. Natl. Acad. Sci., USA*, 88:11120–11123 (1991); Barbas et al, *Proc. Natl. Acad. Sci., USA*, 89:4457–4461 (1992); and Gram et al, *Proc. Natl. Acad. Sci., USA*, 89:3576–3580 (1992).

Because the phage's heterodimeric receptor is comprised of first and second polypeptides of an autogenously assembling receptor, e.g. $V_H$ and $V_L$ polypeptides that form a Fab, the library can also be characterized as containing or expressing a multiplicity of receptor specificities. Thus, libraries express at least $10^5$, preferably at least $10^6$ and more preferably at least $10^7$ different receptors, such as different antibodies, T cell receptors, integrins and the like.

The size of the library can vary depending on a number of factors, particularly the method in which the library is produced. As used herein, size connotes the complexity or diversity of the library, that is the number of different species making up the library, rather than the absolute number of particles in the library.

Thus, where a library is produced by first separately cloning two repertoires of genes, corresponding to the first and second polypeptides of the heterodimeric receptor, the resulting library size after randomly combining the two repertoires in the form of a dicistronic vector is greatly increased. For example, consider light chain and heavy chain variable antibody gene repertoires, each having $10^6$ different members. Combining the two repertoires theoretically yields a phage library containing $10^{12}$ possible different heterodimeric receptor species.

Isolation (segregation) of a phage particle containing a DNA molecule encoding one or both members of a heterodimeric receptor is typically conducted by segregation of the filamentous phage particle containing the gene or genes of interest away from the population of other phage particles comprising the library. Segregation of phage particles involves the physical separation and propagation of individual phage particles away from other particles in the library. Methods for physical separation of filamentous phage particles to produce individual particles, and the propagation of the individual particles to form populations of progeny phage derived from the individual segregated particle are generally well known in the filamentous phage arts.

A preferred separation method involves the identification of the expressed heterodimer on the surface of the phage particle by means of a ligand binding specificity between the phage particle and a preselected ligand. Exemplary and preferred is the use of "panning" methods whereby a suspension of phage particles is contacted with a solid phase ligand (antigen) and allowed to specifically bind (or immunoreact where the heterodimer includes an immunoglobulin variable domain). After binding, non-bound particles are washed off the solid phase, and the bound phage particles are those that contain ligand-specific heterodimeric receptor (heterodimer) on their surface. The bound particles can then be recovered by elution of the bound particle from the solid phase, typically by the use of aqueous solvents that interfere with the ligand-receptor interaction. Typical solvent include buffers having high ionic strength, low pH, or an amount of soluble competing ligand sufficient to disrupt the receptor-ligand binding interaction.

An alternate method for separating a phage particle based on the ligand specificity of the surface-expressed heterodimer from a population of particles is to precipitate the phage particles from the solution phase by crosslinkage with the ligand.

The use of the above particle segregation methods provides a means for screening a population of filamentous phage particles present in a phage library of this invention. As applied to a phage library, screening can be utilized to enrich the library for one or more particles that express a heterodimer having a preselected ligand binding specificity. Where the library is designed to contain multiple species of heterodimers that all have some detectable measure of ligand binding activity, but differ in protein structure, antigenicity, ligand binding affinity or avidity, and the like, the screening methods can be utilized sequentially to first produce a library enriched for a preselected binding specificity, and then to produce a second library further enriched by further screening comprising one or more isolated phage particles. Methods for measuring ligand binding activities, antigenicity and the like interactions between a ligand and a receptor are generally well known and are not discussed further as they are not essential features of the present invention.

Thus, in one embodiment, a phage library is a population of particles enriched for a preselected ligand binding specificity.

As described herein, a particular advantage of a filamentous phage in the present invention is that the DNA molecule present in the phage particle and encoding one or both of the members of the heterodimeric receptor can be segregated from other DNA molecules present in the library on the basis of the presence of the particular expressed heterodimeric receptor on the surface of the phage particle. Furthermore, the additional presence of an indicating fusion polypeptide provides an advantage in the screening procedure, in that it affords a direct signal of the presence of the phage particle. There is no need for the use of a secondary indicating reagent in library screening, such as a secondary labelled antibody.

For example, where a particular antibody reactivity is being sought in a library, the phage library is typically first adsorbed (immunoreacted) against a preselected antigen in the solid phase. Thereafter, the presence of a positive-reacting phage from the library can be detected in the solid phase using a labelled antibody specific for the class of antibodies in the library. This detection step requires a second incubation step, which adds to the manipulation. In addition, the use of the antibody can provide unwanted non-specific reactions, thereby obscuring the sensitivity of a screening procedure to identify a desired phage-containing antibody molecule. The use of direct detection of the indicator fusion polypeptide eliminates (1) the need for the secondary antibody incubation step, and (2) the loss in resolution due to non-specific binding in the secondary antibody screen.

The actual amount of fusion polypeptide present on the surface of a phage particle depends, in part, on the choice of coat protein membrane anchor present in the fusion polypeptide.

Where the anchor is derived from cpIII, there are typically about 1 to 4 fusion polypeptides per phage particle. Where the anchor is derived from the more preferred cpVIII, there is the potential for hundreds of fusion polypeptides on the particle surface depending on the growth conditions and other factors as discussed herein. The actual amount of fusion polypeptides present on a phage particle can be adjusted by controlling the amount "captured" by the phage particle as it is being synthesized in a host cell.

Typically, a phage particle in a library of this invention contains from about 10 to about 500 cpVIII-derived fusion polypeptides on the surface of each particle, and more preferably about 20 to 50 fusion polypeptides per particle.

In another embodiment, the present invention contemplates a population of phage particles that are the progeny of a single particle, and therefor all express the same heterodimer on the particle surface. Such a population of phage are homogeneous and clonally derived, and therefore provide a source for expressing large quantities of a particular fusion polypeptide or heterodimeric receptor.

D. Methods for Producing a Filamentous Phage

Because a filamentous phage particle of the invention contains two separate surface-accessible elements, namely a heterodimeric receptor and a heterologous polypeptide expressed from separate DNA expression vectors in the phage, the preparation of a phage particle is preferably accomplished by the introduction of two vectors into the same prokaryotic host cells. A further embodiment, however, contemplates the introduction of one vector in which both of the genes for surface expression of the heterodimeric receptor and heterologous polypeptide are present. The introduction of the vectors can be accomplished by a variety of means depending on the particular application of the present technology.

Generally, the method for producing filamentous phage particles having on the particle surface (i) a first fusion polypeptide and (ii) a heterodimeric receptor consisting of first and second receptor polypeptides comprises the steps of:

a) introducing into a prokaryotic host cell permissive for filamentous phage replication a first rDNA vector comprising a nucleotide sequence capable of expressing the first fusion polypeptide, wherein the first fusion polypeptide comprises a heterologous polypeptide operatively fused to a first filamentous phage coat protein membrane anchor;

b) introducing into the same prokaryotic host cell a second vector for expressing the heterodimeric receptor comprising a nucleotide sequence capable of expressing the first and second receptor polypeptides, wherein one of the receptor polypeptides is fused to a second filamentous phage coat protein membrane anchor; and c) maintaining the prokaryotic host cell containing the introduced first and second vectors under conditions sufficient for filamentous phage production and under conditions sufficient for expression of the first fusion polypeptide and expression of the heterodimeric receptor, thereby forming the phage particle.

The introducing steps can be accomplished simultaneously, as in a co-transformation of E. coli with a mixture of the rDNA vectors, or can be accomplished sequentially. Transformation of a prokaryotic host cell is well known and includes calcium-mediated transformation, electroporation and the like. Other introducing means include infection by a filamentous phage particle.

The method for producing filamentous phage particles further comprises having a first vector comprising:

(i) a first nucleotide sequence comprising a nonsense chain termination codon operatively linked downstream to the nucleotide sequence encoding the heterologous polypeptide, where the termination codon results in the expression of a soluble heterologous polypeptide, and;

(ii) a second nucleotide sequence comprising a tRNA suppressor gene, where the expression of the suppressor gene allows sufficient translation through the termination codon to result in the expression of a heterologous polypeptide fused to a first filamentous phage coat protein membrane anchor.

In preferred embodiments, the heterologous polypeptide of step (ii) is fused to a coat protein membrane anchor through a linker polypeptide.

A prokaryotic host cell useful for producing a filamentous phage of this invention is one permissive for filamentous infection and morphogenesis, and is well characterized in the filamentous phage arts. A preferred host is an E. coli cell, although other prokaryotic cells may be used.

A further embodiment for the production of filamentous phase includes a procaryotic host cell that is capable of producing soluble heterologous polypeptide. A preferred procaryotic host is a PhoR mutant capable of endogenously producing soluble alkaline phosphatase.

In preferred embodiments, the method for producing filamentous phage particles results in the formation of a first fusion polypeptide that comprises a dimer. The fusion polypeptide is an anchored heterologous indicator polypeptide monomer of this invention, preferably alkaline phosphatase anchored to phage coat protein 8 and more preferably anchored to the coat protein through a polypeptide linker. A dimer of this invention is formed from the joining of two heterologous polypeptide monomers. In a preferred embodiment, an anchored alkaline phosphatase monomer forms a dimer with a second alkaline phosphatase monomer through a disulfide bond between cysteine residues on each of the monomers. More preferably, the dimer results between an anchored monomer and a non-anchored soluble monomer. The prevalence of various forms of dimers is presented in Section B., entitled "Filamentous Phage".

Various methods of preparing a dimer are contemplated for use in this invention. Both non-anchored soluble and anchored monomeric forms of the heterologous indicator polypeptide are produced from an expression vector of this invention. Once expressed, the monomeric forms can form dimers through intersubunit bonds. The anchored and non-anchored soluble monomeric forms of the heterologous indicator polypeptide can be produced from two separate expression vectors. Exemplary methods for providing monomeric polypeptides in this aspect are described in Example 8.

A preferred embodiment for the expression of both anchored and non-anchored soluble heterologous polypeptides is the use of a single vector in which nucleotide sequences are present for encoding:

a) a suppressor tRNA gene capable of expressing a suppressor tRNA molecule; and b) an expression cassette for expressing a first and second heterologous polypeptide subunit.

The expression cassette comprises a transcriptional unit for producing a messenger RNA transcript that encodes both first and second subunits of the heterologous polypeptide. The cassette is designed to produce both subunits, one anchored to a phage membrane coat protein and the other not anchored, i.e, soluble, through the regulation of a nonsense chain termination codon and a tRNA suppressor gene. Exemplary expression cassettes for use with a tRNA suppressor gene are present in expression vectors, the latter of which are those that provide for the expression of bacterial alkaline in either the non-anchored soluble form such as pPhoC as described in Example 8, or in the anchored form such as pPho8, pPhoL8 and pPhoL8B as described in Example 5.

Nonsense suppression is a process where translation of messages in a transcriptional unit does not always stop when the ribosome encounters a chain termination codon, but sometimes continues, with a new amino acid inserted at the end of the growing polypeptide chain. Strains of E. coli in which nonsense suppression occurs are said to contain nonsense suppressors. The mechanism of nonsense suppression is the following: the bacterial cell contains a mutant species of tRNA in which the anticodon loop has mutated so that it base pairs with the UAG amber codon, for example. In the instant invention, by inserting a transcription stop codon, such as an amber stop (TAG) codon, into the nucleotide sequence encoding the anchor, one expression vector is used to produce both anchored and soluble forms of the heterologous polypeptide, where two plasmids were used before.

Induction of a chain termination codon-bearing plasmid of this invention, in the presence of an amber suppressor tRNA would give soluble alkaline phosphatase and anchored alkaline phosphatase resulting from partial suppression of the amber stop codon. The tRNA suppression gene reverses the effects of nonsense mutations, which allows for some translation through the nonsense codon. Exemplary tRNA suppressor genes are well known in the art. The use of nonsense suppression to generate altered proteins has been described by Miller et al., *Methods in Enzymology,* 208:543–563 (1991), the disclosure of which is hereby incorporated by reference. Preferred tRNA suppressor genes are supD, supE, supF, supG, supP and the like. In addition, new tRNA suppressor genes can be designed and constructed in vitro by annealing synthetic oligonucleotides. Suppressors are known that insert various amino acids in place of an amber stop codon, with various efficiencies.

Coding sequences for such suppressors could be incorporated into the pPhoAL8 expression vector described in Example 9 to form a vector, pPhoAL8S, which in the presence of a Fab-encoding pComb3 plasmid and helper phage results in improved phage-linked antibody and heterologous polypeptide systems, referred to as PhoPhabs, that have increased signal due to better incorporation of alkaline phosphatase in phage. An exemplary tRNA suppressor gene is described in Example 9. The system could be optimized for PhoPhab production by testing known suppressors that insert different amino acids at varying levels, and the position of the amber stop codon could be moved because suppression in known to be dependent on the context.

Exemplary nonsense chain termination codons include amber (UAG), ochre (UAA), and opal (UGA). The codons in parentheses indicate the mRNA. The corresponding nucleotide sequence present in the vector for amber is TAG. An exemplary termination codon-bearing plasmid of this invention is pPhoAL8S and is described in Example 9.

In addition to using expression vectors for obtaining monomeric subunits, also contemplated for use in this invention is the use of procaryotic host cells that are capable of endogenously producing monomeric forms of heterologous indicator polypeptides. Mutants of E. coli are well known in the art and have been studied for over 25 years. These strains can be obtained commercially or mutated by well known techniques to a PhoR- phenotype such that it would constitutively express BAP. See Miller, "Experiments in Molecular Genetics", Cold Spring Harbor Laboratory Press, (1972).

An exemplary procaryotic host cell is E. coli that is a phoR mutant, strain phoR8, capable of expressing bacterial alkaline phosphatase, as described by Kreuzer et al., *Genetics,* 81:459–468 (1975), the disclosure of which is hereby incorporated by reference. Mutant phoR constitutively express monomeric forms of bacterial alkaline phosphatase based on clonal variation phenotype. The alkaline phosphatase clonal variation is characterized by an alteration between a plus and negative phenotype regulated by the bacterial phoM operon and the presence of glucose. The switching of the phenotype occurs at the transcriptional level of the bacterial alkaline phosphatase structural gene, phoA, and it is recA independent. Exemplary methods of using such a host cell are described in Example 9.

Typically, the method for producing a filamentous phage particle of this invention is practiced to form a library of phage particles. In this regard, the rDNA being introduced is in the form of a plurality of rDNA vector molecules, and the host cell is present as a plurality of host cells.

Thus, a related embodiment contemplates a method for producing a library of phage particles of this invention as described above, except that the rDNA vectors and host cells are manipulated in populations.

Depending on the type of library to be produced, one can practice the above introducing steps for producing a library differently.

For example, a pre-existing combinatorial heterodimeric receptor phage library can be provided in which each phage particle contains a rDNA vector for expressing a heterodimeric receptor molecule. Such libraries have been previously described, and include the pComb3 and pComb8 based libraries described herein. The library can be manipulated into the form of (1) filamentous phage particles containing the rDNA molecule that encodes the heterodimeric receptor, (2) E. coli cells containing the rDNA molecules, or (3) purified rDNA molecules, prior to the preparation of a filamentous phage or phage library of this invention.

In the method, an rDNA vector that expresses the heterologous fusion polypeptide is combined with the provided rDNA vector (in one of its various forms) within a single E. coli host cell such that the host cell contains both the rDNA vector for expressing the heterologous fusion polypeptide and the rDNA vector for expressing the heterodimeric receptor. The combination can be repeated multiple times with multiple members of the library, such as in a batch process in which multiple species are present. Thus, a heterologous fusion polypeptide-expressing rDNA vector is combined with a pre-existing library of rDNA vectors that can express a heterodimeric receptor, thereby forming the phage library of this invention.

A filamentous phage particle of this invention is produced by standard filamentous phage particle preparation methods and depends on the presence in a DNA expression vector of this invention of a filamentous phage origin of replication as described herein to provide the signals necessary for (1) production of a single-stranded filamentous phage replicative form and (2) packaging of the replicative form into a filamentous phage particle. Such a DNA molecule can be packaged when present in a bacterial cell host upon introduction of genetic complementation to provide the filamentous phage proteins required for production of infectious phage particles.

Therefore, the maintaining step of step (c) above is conducted to facilitate expression and assembly of the genes in the introduced vector to form the phage particle. Typically, an rDNA vector contains the minimum genetic information for the preparation and manipulation of rDNA molecules, and as such, does not contain the complete range of genes required for production of a filamentous phage particle. A typical and preferred method for genetic complementation is to infect a bacterial host cell containing a DNA expression vector of this invention with a helper filamentous phage, thereby providing the genetic elements required for phage particle assembly. Exemplary helper rescue methods are described herein at Example 2, and described by Short et al., Nuc. Acids Res., 16:7583–7600 (1988).

Thus, the maintaining step typically includes a superinfection by helper phage combined with an incubation period under the conditions for allowing the helper genome to express the complementing genes and to assist the expression and assembly of a phage particle.

When practicing the method of producing a phage of this invention using two vectors, it is important to use different and compatible prokaryotic origins of replication on the two different rDNA vectors, as discussed herein, so that the two vectors can both be simultaneously maintained in the same host cell. Thus, in preferred embodiments, the first and second vectors contain different and compatible prokaryotic origins of replication. Preferably, these different and compatible origins of replication are ColE1 and p15A, although other replicons may be utilized so long as there is compatibility in a single host cell.

In addition, it is important to utilize a system of selection for maintaining both rDNA vectors in the same host cell. This is typically accomplished by providing separate and distinct selectable markers on the two rDNA vectors. Preferred are the use of the cat gene on the first rDNA vector and the amp gene on the second rDNA vector.

The level of heterodimeric receptor captured on the surface of a filamentous phage particle during the process of phage particle extrusion from the host cell can be controlled by a variety of means. In one embodiment, the levels of fusion polypeptides are controlled by the use of strong promoters in the first and second cistrons for expressing the polypeptides, such that transcription of the fusion polypeptide cistrons occurs at a relative rate equal to or greater than the rate of transcription of the cpVIII gene on the helper phage. In another embodiment, the helper phage can have an amber mutation in the gene for expressing cpVIII, such that less wild-type cpVIII is transcribed in the host cell than fusion polypeptides, thereby leading to increased ratios of fusion polypeptide compared to cpVIII during the extrusion process.

In another embodiment, the amount of heterodimeric receptor on the phage particle surface can be controlled by controlling the timing between expression of fusion polypeptides and the superinfection by helper phage. After introduction of the expression vector into the host cell, longer delay times before the addition of helper phage will allow for increased accumulation of the fusion polypeptides in the host cell, thereby increasing the amount of fusion polypeptide captured by the extruding phage particle.

In a further preferred embodiment, the heterologous indicator polypeptide in the form of a dimer requires that both components comprising the dimer are expressed at levels sufficient for forming a dimer. To that end, the amount of the anchored heterologous fusion protein expressed on the surface of the phage is dependent on the relative ratios of the fusion protein and of the wild type coat protein. The formation of a dimer between the two indicator polypeptide subunits is dependent on the expression of both the anchored fusion protein and the unanchored soluble monomer. Preferably, both the monomeric heterologous fusion protein and the soluble monomer subunit that join to form an indicator polypeptide dimer are in sufficient quantities to allow for dimerization.

Dimers theoretically can result from the joining of two soluble monomers, from a soluble monomer and an anchored monomer, and from two anchored monomers. Phage produced in the presences of a plasmid system that provides for the expression of both soluble and anchored heterologous polypeptide monomers therefore could have a mixture of heterodimers and homodimers on their surface. Thus, even if the expression of the soluble monomeric form is insufficient, dimers conceivably can form between two anchored monomers. However, as described in Example 8, two alkaline phosphatase monomers anchored to coat protein 8 through a 20 amino acid linker polypeptide were unable to form dimers on the surface of phage. The inability to form dimers may be the result of steric hindrance or limitations imposed on the phage extrusion process in E. coli.

As discussed in Example 8, the larger the protein being expressed through a fusion protein anchor to a phage membrane coat protein, the few the number of copies of the fusion protein that are presented on the phage. Size of the fusion protein alone thus can create steric limitations. The preferred indicator polypeptide for use in this invention is alkaline phosphatase that is approximately 90 kilodaltons. Alternatively, a kinetic limitation occurs from competition of wild type coat protein 8 and a fusion protein for incorporation into phage. Markland et al., Gene, 109:13–19 (1991), have shown that lowering the expression of the wild type coat protein 8 with respect to the expression of a fusion protein resulted in an increase of the total number of fusion proteins expressed on the surface of phage. Thus, the extrusion process for either steric or kinetic bases may not provide for expression of fusion proteins in sufficient proximity to one another to allow for the formation of a sufficient number of dimers that provide adequate indicator polypeptide function.

Other limitations to the formation of a preferred dimer of heterologous indicator polypeptides is the formation of dimers between anchored subunits on different phage. This process results in the formation of insoluble, useless phage aggregates. In addition, dimers can form between two non-anchored soluble indicator polypeptide subunits. However, as discussed in Example 8, the formation of the non-preferred homodimer pairs produced as a result of the vector expression systems is reduced in comparison to the formation of heterodimer pairs formed from one anchored fusion protein and one non-anchored soluble polypeptide.

In a related embodiment, the invention contemplates a method of producing a filamentous phage particle of this invention having a preselected binding specificity by screening a library of phage particles that each contain a rDNA vector that expresses a phage surface heterodimeric receptor. The method comprises the steps of:

a) providing a library of filamentous phage particles of this invention each comprising an indicator fusion polypeptide and a heterodimeric receptor on its surface;

b) binding members of the provided library onto a plurality of preselected ligand molecules present in the solid phase to form a plurality of solid-phase bound phage particles;

c) assaying the solid phase for the presence of the indicator polypeptide, and thereby the presence of a solid-phase bound phage particle containing the surface-exposed heterodimeric receptor having a preselected binding specificity; and d) recovering the solid-phase adsorbed phage particle that contains the heterodimeric receptor.

In the method of screening a library, a further embodiment comprises:

iii) a dimer having one subunit that is an indicator polypeptide fused to a filamentous phage coat protein membrane anchor and a second subunit of the dimer that is soluble, i.e., not anchored to a phage coat protein.

The preferred dimer is composed of two alkaline phosphatase polypeptides. Preferably, the anchored alkaline phosphatase subunit is fused to the coat protein membrane anchor through a linker polypeptide.

The provided library can be any library of filamentous phage particles of the present invention believed to contain surface exposed heterodimeric receptors that have a binding specificity for a preselected ligand. The library can be of any complexity. The preparation of heterodimeric libraries is described more fully elsewhere herein.

Methods for specifically binding a receptor to a ligand in the solid phase are generally well known in the receptor and immunological arts, and can be applied herein. See in particular, the phage binding reactions and conditions for binding described herein.

Assaying for the presence of the indicator polypeptide depends upon the biological activity of the indicating protein. The indicator polypeptide is selected to be readily detectable, and typically is an enzyme as described earlier. A preferred indicator enzyme is alkaline phosphatase, which can readily be detected in a localized manner, as is well known in the immunological arts. A preferred embodiment for the indicator polypeptide is a dimer of two alkaline phosphatase subunits where the dimer is formed between a free soluble alkaline phosphatase monomer and with an attached alkaline phosphatase monomer anchored to a coat protein by means of a linker polypeptide.

Having identified due to indicator activity species of phage in the library that are present in the solid phase, one recovers the bound phage to yield a particular phage particle. Recovery can be effected by washing in buffers that compete for the specific binding or that disrupt the binding interaction, thereby releasing the solid-phase bound phage particle. Exemplary buffers contain glycine and are at low pH. Elution conditions are described in the Examples.

The above screening and recovery method can be practiced in a variety of formats. For example, a library of phage can be screened for the presence of a heterodimeric receptor specific for a particular binding specificity. In that case, a solid phase ligand is provided in the solid phase and admixed with a liquid suspension of the phage library to form a binding admixture.

Alternatively, a different ligand can be provided in each of a plurality of containers, and aliquots of a single library applied to each container. Because only a few phage particles are expected to specifically bind, one must assay for the presence of the indicator protein's activity in discreet containers in order to determine the well in which the specifically binding heterodimeric receptor is located.

Still further, a "dot blot" format can be utilized in which each "dot" represents a different solid phase-adsorbed antigen, and a single phage library is adsorbed against the entire dot library. The "dot" that produces a detectable indicator protein activity is designated as having a desired heterodimeric receptor.

Other screening formats using a phage having the indicator fusion polypeptide are contemplated and will be readily apparent to one skilled in the immunological arts.

E. DNA Expression Vectors

1. Vectors For Producing Phagemid Surface Heterologous Protein

A vector of the present invention is a recombinant DNA (rDNA) molecule containing a nucleotide sequence that codes for and is capable of expressing a fusion polypeptide containing, in the direction of amino- to carboxy-terminus, (1) a prokaryotic secretion signal domain, (2) a heterologous polypeptide, and (3) a filamentous phage membrane anchor domain. The vector includes DNA expression control sequences for expressing the fusion polypeptide, preferably prokaryotic control sequences.

The filamentous phage membrane anchor is preferably a domain of the cpIII or cpVIII coat protein capable of associating with the matrix of a filamentous phage particle, thereby incorporating the fusion polypeptide onto the phage surface. In a particularly preferred embodiment, the membrane anchor is cpVIII.

The secretion signal is a leader peptide domain of a protein that targets the protein to the periplasmic membrane of gram negative bacteria.

A preferred secretion signal is a pelB secretion signal. The predicted amino acid residue sequences of the secretion signal domain from two pelB gene product variants from *Erwinia carotova* are shown in Table 1 as described by Lei, et al., *Nature,* 331:543–546 (1988). A particularly preferred pelB secretion signal is also shown in Table 1.

The leader sequence of the pelB protein has previously been used as a secretion signal for fusion proteins. Better et al., *Science,* 240:1041–1043 (1988); Sastry et al., *Proc. Natl. Acad. Sci., USA,* 86:5728–5732 (1989); and Mullinax et al., *Proc. Natl. Acad. Sci., USA,* 87:8095–8099 (1990).

Amino acid residue sequences for other secretion signal polypeptide domains from *E. coli* useful in this invention are also listed in Table 1. Oliver, In Neidhard, F. C. (ed.), *Escherichia coli* and Salmonella Typhimurium, American Society for Microbiology, Washington, D.C., 1:56–69 (1987).

TABLE 1

Leader Sequences

| SEQ ID NO: | Type | Amino Acid Residue Sequence |
|---|---|---|
| (5) | PelB[1] | MetLysTyrLeuLeuProThrAlaAlaAlaGlyLeuLeu LeuLeuAlaAlaGlnProAlaMet |
| (6) | pelB[2] | MetLysTyrLeuLeuProThrAlaAlaAlaGlyLeuLeu LeuLeuAlaAlaGlnProAlaGlnProAlaMetAla |
| (7) | pelB[3] | MetLysSerLeuIleThrProIleAlaAlaGlyLeuLeu LeuAlaPheSerGlnTyrSerLeuAla |
| (8) | MalE[4] | MetLysIleLysThrGlyAlaArgIleLeuAlaLeuSer AlaLeuThrThrMetMetPheSerAlaSerAla LeuAlaLysIle |
| (9) | OmpF[4] | MetMetLysArgAsnIleLeuAlaValIleValProAla LeuLeuValAlaGlyThrAlaAsnAlaAlaGlu |
| (10) | PhoA[4] | MetLysGlnSerThrIleAlaLeuAlaLeuLeuProLeu LeuPheThrProValThrLysAlaArgThr |
| (11) | Bla[4] | MetSerIleGlnHisPheArgValAlaLeuIleProPhe PheAlaAlaPheCysLeuProValPheAlaHisPro |
| (12) | LamB[4] | MetMetIleThrLeuArgLysLeuProLeuAlaValAla ValAlaAlaGlyValMetSerAlaGlnAlaMetAlaVal Asp |
| (13) | Lpp[4] | MetLysAlaThrLysLeuValLeuGlyAlaValIleLeu GlySerThrLeuLeuAlaGlyCysSer |
| (14) | cpVIII[5] | MetLysLysSerLeuValLeuLysAlaSerValAlaVal AlaThrLeuValProMetLeuSerPheAla |
| (15) | cpIII[6] | MetLysLysLeuLeuPheAlaIleProLeuValValPro PheTyrSerHisSer |

[1]pelB used in this invention
[2]pelB from *Erwinia carotovora* gene
[3]pelB from *Erwinia carotovora* EC 16 gene
[4]leader sequences from *E. coli*
[5]leader sequence for cpVIII
[6]leader sequence for cpIII The pelB secretion signal having the amino acid residue sequence shown in SEQ ID NO:5 is a preferred DNA sequence for inclusion in a DNA expression vector of this invention.

Preferred membrane anchors for this invention are obtainable from filamentous phage M13, f1, fd, and the like equivalent filamentous phage. Preferred membrane anchor domains are found in the coat proteins encoded by gene III and gene VIII.

The membrane anchor domain of a filamentous phage coat protein is a portion of the carboxy terminal region of the coat protein and includes a region of hydrophobic amino acid residues for spanning a lipid bilayer membrane, and a region of charged amino acid residues normally found at the cytoplasmic face of the membrane and extending away from the membrane.

In the phage f1, gene VIII coat protein's membrane spanning region comprises residue Trp-26 through Lys-40, and the cytoplasmic region comprises the carboxy-terminal 11 residues from 41 to 52. Ohkawa et al., *J. Biol. Chem.,* 256:9951–9958 (1981). An exemplary membrane anchor would consist of residues 26 to 40 of cpVIII.

Thus, the amino acid residue sequence of a preferred membrane anchor domain is derived from the M13 filamentous phage gene VIII coat protein (also designated cpVIII or cp8). A preferred cpVIII-derived membrane anchor has a sequence shown in SEQ ID NO:17 from residue 1 to residue 50. Gene VIII coat protein is present on a mature filamentous phage over the majority of the phage particle with typically about 2500 to 3000 copies of the coat protein.

In addition, the amino acid residue sequence of another preferred membrane anchor domain is derived from the M13 filamentous phage gene III coat protein (also designated cpIII). A preferred cpIII-derived membrane anchor has a sequence shown in SEQ ID NO 16 from residue 1 to residue 211. Gene III coat protein is present on a mature filamentous phage at one end of the phage particle with typically about 4 to 6 copies of the coat protein.

For detailed descriptions of the structure of filamentous phage particles, their coat proteins and particle assembly, see the reviews by Rached et al., *Microbiol. Rev.,* 50:401–427 (1986); and Model et al., in "The Bacteriophages: Vol. 2", R. Calendar, ed. Plenum Publishing Co., pp. 375–456, (1988).

DNA expression control sequences comprise a set of DNA expression signals for expressing a structural gene product and include both 5' and 3' transcriptional promotor and terminator elements, as is well known, operatively linked to the cistron such that the cistron is able to express a structural gene product. The set of nucleotides defining a DNA expression control sequences and the structural gene product are also referred collectively as an expression cassette. The 5' control sequences define a promoter for initiating transcription (transcriptional promoter) and a ribosome binding site operatively linked at the 5' terminus of the upstream translatable DNA sequence.

To achieve high levels of gene expression in *E. coli,* it is necessary to use not only strong promoters to generate large quantities of mRNA, but also ribosome binding sites to ensure that the mRNA is efficiently translated. In *E. coli,* the ribosome binding site includes an initiation codon (AUG), or translational initiator, and a sequence 3–9 nucleotides long located 3–11 nucleotides upstream from the initiation codon [Shine et al., *Nature,* 254:34 (1975)]. The sequence, AGGAGGU, which is called the Shine-Dalgarno (SD) sequence, is complementary to the 3' end of *E. coli* 16S mRNA. Binding of the ribosome to mRNA and the sequence at the 3' end of the mRNA can be affected by several factors:

(i) The degree of complementarity between the SD sequence and 3' end of the 16S tRNA.

(ii) The spacing and possibly the DNA sequence lying between the SD sequence and the AUG [Roberts et al., *Proc. Natl. Acad. Sci., USA,* 76:760 (1979a); Roberts et al., *Proc. Natl. Acad. Sci., USA,* 76:5596 (1979b); Guarente et al., *Science,* 209:1428 (1980); and Guarente et al., *Cell,* 20:543 (1980)] Optimization is achieved by measuring the level of expression of genes in plasmids in which this spacing is systematically altered. Comparison of different mRNAs shows that there are statistically preferred sequences from positions −20 to +13 (where the A of the AUG is position 0) [Gold et al., *Annu. Rev. Microbiol.,* 35:365 (1981)]. Leader sequences have been shown to influence translation dramatically (Roberts et al., 1979 a, b supra).

(iii) The nucleotide sequence following the AUG, which affects ribosome binding [Taniguchi et al.,*J. Mol. Biol.,* 118:533 (1978)].

Useful ribosome binding sites are shown in Table 2 below.

TABLE 2

| SEQ ID NO: | Ribosome Binding Sites[a] |
|---|---|
| 1. (18) | 5' AAUCUUGGAGGCUUUUUUAUGGUUCGUUCU |
| 2. (19) | 5' UAACUAAGGAUGAAAUGCAUGUCUAAGACA |
| 3. (20) | 5' UCCUAGGAGGUUUGACCUAUGCGAGCUUUU |
| 4. (21) | 5' AUGUACUAAGGAGGUUGUAUGGAACAACGC |

[a]Sequences of initiation regions for protein synthesis in four phage mRNA molecules are underlined.
AUG = initiation codon (double underlined)
1. = Phage øX174 gene-A protein
2. = Phage QB replicase
3. = Phage R17 gene-A protein
4. = Phage lambda gene-cro protein The 3' control sequences define at least one termination (stop) codon in frame with and operatively linked to the heterologous fusion polypeptide.

In preferred embodiments, the vector utilized includes a prokaryotic origin of replication or replicon i.e., a DNA sequence having the ability to direct autonomous replication and maintenance of the recombinant DNA molecule extra chromosomally in a prokaryotic host cell, such as a bacterial host cell, transformed therewith. Such origins of replication are well known in the art.

Preferred origins of replication are those that are efficient in the host organism. A preferred host cell is E. coli. For use of a vector in E. coli, a preferred origin of replication is ColE1 found in pBR322 and a variety of other common plasmids. Also preferred is the p15A origin of replication found on pACYC and its derivatives. The ColE1 and p15A replicon have been extensively utilized in molecular biology, are available on a variety of plasmids and are described at least by Sambrook et al, in "Molecular Cloning: a Laboratory Manual" 2nd edition, Cold Spring Harbor Laboratory Press, 1989.

The ColE1 and p15A replicons are particularly preferred for use in the present invention because they each have the ability to direct the replication of plasmid in E. coli while the other replicon is present in a second plasmid in the same E. coli cell. That is, ColE1 and p15A are non-interfering replicons that allow the maintenance of two plasmids in the same host. See, for example, Sambrook et al., supra, at pages 1.3–1.4. This feature is particularly important to the present invention because a single host cell permissive for phage replication must support the independent and simultaneous replication of two separate vectors, namely the vector for expressing a heterologous fusion polypeptide and the vector for expressing a heterodimeric receptor.

In addition, those embodiments that include a prokaryotic replicon also include a gene whose expression confers a selective advantage, such as drug resistance, to a bacterial host transformed therewith. Typical bacterial drug resistance genes are those that confer resistance to ampicillin, tetracycline, neomycin/kanamycin or cholamphenicol. Vectors typically also contain convenient restriction sites for insertion of translatable DNA sequences. Exemplary vectors are the plasmids pUC8, pUC9, pBR322, and pBR329 available from BioRad Laboratories, (Richmond, Calif.) and pPL and pKK223 available from Pharmacia, (Piscataway, N.J.).

A particularly preferred rDNA vector contains a heterologous fusion polypeptide that functions as an indicator on the surface of a filamentous phage of this invention. A preferred indicator polypeptide is alkaline phosphatase described further herein.

Figure 8:
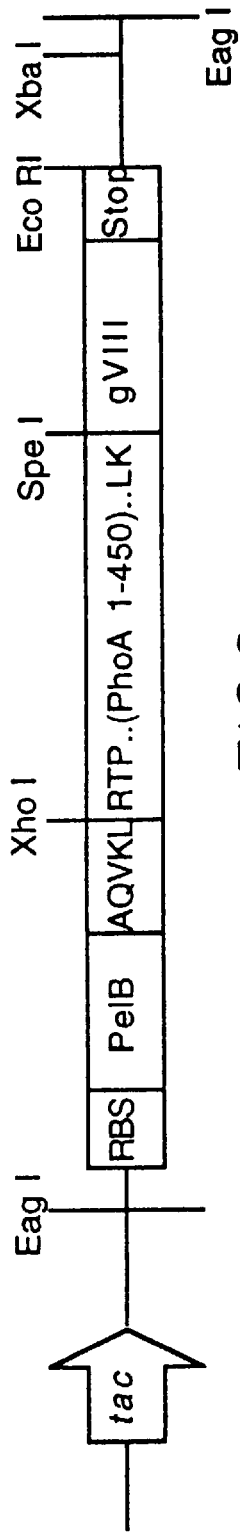
FIG. 8 is a schematic representation of the pPho8cat expression vector prepared as described in Example 5a having the following operatively linked elements: a tac promoter; a Eag restriction cloning site; a ribosome binding site (RBS); a pelB leader sequence followed by a nucleotide sequence that encodes a five amino acid residue linker; a Xho I restriction cloning site; the nucleotide sequence encoding the mature alkaline phosphatase protein (PhoA) of which the amino and carboxy terminal amino acids are shown; a Spe I restriction cloning site; the anchor or coat protein VIII (gVIII) followed by a stop codon and an EcoR I and Xba I restriction cloning site.

Preferred vectors contain the transcriptional unit (expression cassette) shown in FIG. 8 that defines an indicator fusion polypeptide of this invention that includes (1) transcriptional promotor (2) a ribosome binding site, (3) a translational start codon at the beginning of the Pel B prokaryotic secretion signal domain, (4) coding sequences for a short polypeptide linker of about 8 amino acid residues, (5) coding sequences for an alkaline phosphatase (APase) polypeptide of about 450 amino acid residues, (6) coding sequences for the cpVIII membrane anchor, (7) a translational stop codon, and (8) a transcriptional terminator. Exemplary vectors having this transcriptional unit are pPho8cat, pPho8B, pPhoL8 and pPhoL8B shown in FIGS. 9, 10, 11, and 12, respectively, and described in Example 5 and 8.

In a related embodiment, a preferred transcriptional unit of a vector of this invention is the same as the above alkaline phosphatase indicator polypeptide, except that a second linker polypeptide is located between the APase polypeptide and the membrane anchor. Preferably, the second linker is from 3 to 50 amino acid residues in length. In one embodiment, the linker is comprised of amino acid residues that predominantly form an alpha helix. In another embodiment, the second linker is comprised of the multimeric repeating polypeptide unit (EGGGS)n, (SEQ ID NO:91, amino acid residues 1–5) where n is 2 to 10, and preferably is 4. A vector in which the second linker is the repeating unit where n is 4 is the vector pPhoL8 illustrated in FIG. 11 and described in Example 5.

In addition, a preferred vector contains one of the above transcriptional units including APase, and further comprises a p15A origin of replication, and a selectable marker (cat) conferring resistance to chloramphenicol. Preferably, the vector also contain a filamentous phage origin of replication, preferably the f1 origin, that allows packaging of the vector into phage particles for delivery to permissive host cells by phage infection.

In another embodiment, the invention describes a method for producing both the soluble APase subunit and the APase fusion protein subunit from the same transcriptional unit by the use of suppressor tRNA molecules which can co-express the two subunits by suppression of the nonsense chain termination codon located between the alkaline phosphatase coding sequences and the filamentous phage coat protein membrane anchor coding sequences.

Thus, in this embodiment, the invention contemplates a vector for practicing the method. The vector can express both a first and second polypeptide subunits of an alkaline phosphatase dimer which upon expression is capable of assembly on the surface of a filamentous phage particle as described herein. The vector comprises a nucleotide sequence that encodes:

a) a suppressor tRNA gene capable of expressing a suppressor tRNA molecule; and b) an expression cassette for expressing the first and second polypeptide subunits, wherein the expression cassette comprises:

i) a transcriptional promoter and transcriptional terminator for producing a messenger RNA transcript that encodes the first and second polypeptide subunits;

ii) a first open reading frame that encodes soluble alkaline phosphatase beginning with a translational initiator and ending with a nonsense chain termination codon selected from the group consisting of amber, ochre and opal; and iii) a second open reading frame operatively linked downstream to the first open reading frame, the second open reading frame encoding a filamentous phage coat protein membrane anchor such that upon suppression of the nonsense chain termination codon by the suppressor tRNA molecule, the first and second open reading frames are translated as one polypeptide, the translated polypeptide being a fusion protein having alkaline phosphatase operatively linked in frame with the filamentous phage coat protein membrane anchor.

The use of suppressor tRNA genes to regulate "read through" of a translation termination codon and form a larger fusion protein is described in detail herein. Any of a variety of suppressor tRNA genes may be used, as is well known and discussed herein. The location of the suppressor tRNA gene in the vector relative to the expression cassette for producing the dimer is not critical, so long as both transcriptional units are able to independently express their respective structural genes.

A preferred vector for this purpose encodes a filamentous phage coat protein membrane anchor of this invention, and particularly preferred vectors encode a polypeptide linker in the fusion protein as described herein.

2. Vectors For Producing Phagemid Surface Heterodimeric Receptor

A vector for expression of a heterodimeric receptor on the surface of a filamentous phage particle is a recombinant DNA (rDNA) molecule adapted for receiving and expressing translatable first and second DNA sequences in the form of first and second receptor polypeptides wherein one of the receptor polypeptides is fused to a filamentous phage coat protein membrane anchor. That is, of the receptor polypeptides is a fusion polypeptide containing a filamentous phage membrane anchor domain and a prokaryotic secretion signal domain.

A DNA expression vector for expressing a heterodimeric receptor provides a system for independently cloning (inserting) the two translatable DNA sequences into two separate cassettes present in the vector, to form two separate cistrons for expressing the first and second polypeptides of a heterodimeric receptor, or the ligand binding portions of the polypeptides that comprise a heterodimeric receptor. The DNA expression vector for expressing two cistrons is referred to as a dicistronic expression vector.

The vector comprises a first cassette that includes upstream and downstream translatable DNA sequences operatively linked via a sequence of nucleotides adapted for directional ligation to an insert DNA. The upstream translatable sequence encodes the secretion signal as defined herein. The downstream translatable sequence encodes the filamentous phage membrane anchor as defined herein. The cassette preferably includes DNA expression control sequences for expressing the receptor polypeptide that is produced when an insert translatable DNA sequence (insert DNA) is directionally inserted into the cassette via the sequence of nucleotides adapted for directional ligation. The filamentous phage membrane anchor is preferably a domain of the cpIII or cpVIII coat protein capable of binding the matrix of a filamentous phage particle, thereby incorporating the fusion polypeptide onto the phage surface.

The receptor expressing vector also contains a second cassette for expressing a second receptor polypeptide. The second cassette includes a second translatable DNA sequence that encodes a secretion signal, as defined herein, operatively linked at its 3' terminus via a sequence of nucleotides adapted for directional ligation to a downstream DNA sequence of the vector that typically defines at least one stop codon in the reading frame of the cassette. The second translatable DNA sequence is operatively linked at its 5' terminus to DNA expression control sequences forming the 5' elements. The second cassette is capable, upon insertion of a translatable DNA sequence (insert DNA), of expressing the second fusion polypeptide comprising a receptor of the secretion signal with a polypeptide coded by the insert DNA.

An upstream translatable DNA sequence encodes a prokaryotic secretion signal as described earlier. The upstream translatable DNA sequence encoding the pelB secretion signal having the amino acid residue sequence shown in SEQ ID NO 5 is a preferred DNA sequence for inclusion in a receptor expression vector.

A downstream translatable DNA sequence encodes a filamentous phage membrane anchor as described earlier. Thus, a downstream translatable DNA sequence encodes an amino acid residue sequence that corresponds, and preferably is identical, to the membrane anchor domain of either a filamentous phage gene III or gene VIII coat polypeptide.

A cassette in a DNA expression vector of this invention is the region of the vector that forms, upon insertion of a translatable DNA sequence (insert DNA), a sequence of nucleotides capable of expressing, in an appropriate host, a receptor polypeptide. The expression-competent sequence of nucleotides is referred to as a cistron. Thus, the cassette comprises DNA expression control elements operatively linked to the upstream and downstream translatable DNA sequences. A cistron is formed when a translatable DNA sequence is directionally inserted (directionally ligated) between the upstream and downstream sequences via the sequence of nucleotides adapted for that purpose. The resulting three translatable DNA sequences, namely the upstream, the inserted and the downstream sequences, are all operatively linked in the same reading frame.

Thus, a DNA expression vector for expressing heterodimeric receptors provides a system for cloning translatable DNA sequences into the cassette portions of the vector to produce cistrons capable of expressing the first and second receptor polypeptides of a heterodimeric receptor.

An expression vector, whether it is used to express the heterologous fusion polypeptide or a heterodimeric receptor, is characterized as being capable of expressing, in a compatible host, a structural gene product.

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked.

Vectors therefore preferably contain the replicons and selectable markers described earlier.

As used herein with regard to DNA sequences or segments, the phrase "operatively linked" means the sequences or segments have been covalently joined, preferably by conventional phosphodiester bonds, into one strand of DNA, whether in single or double stranded form.

The choice of vector to which transcription unit or a cassette of this invention is operatively linked depends directly, as is well known in the art, on the functional properties desired, e.g., vector replication and protein expression, and the host cell to be transformed, these being limitations inherent in the art of constructing recombinant DNA molecules.

A sequence of nucleotides adapted for directional ligation, i.e., a polylinker, is a region of the DNA expression vector that (1) operatively links for replication and transport the upstream and downstream translatable DNA sequences and (2) provides a site or means for directional ligation of a DNA sequence into the vector. Typically, a directional polylinker is a sequence of nucleotides that defines two or more restriction endonuclease recognition sequences, or restriction sites. Upon restriction cleavage, the two sites yield cohesive termini to which a translatable DNA sequence can be ligated to the DNA expression vector. Preferably, the two restriction sites provide, upon restriction cleavage, cohesive termini that are non-complementary and thereby permit directional insertion of a translatable DNA sequence into the cassette. In one embodiment, the directional ligation means is provided by nucleotides present in the upstream translatable DNA sequence, downstream translatable DNA sequence, or both. In another embodiment, the sequence of nucleotides adapted for directional ligation comprises a sequence of nucleotides that defines multiple directional cloning means. Where the sequence of nucleotides adapted for directional ligation defines numerous restriction sites, it is referred to as a multiple cloning site.

In a preferred embodiment, a DNA expression vector is designed for convenient manipulation in the form of a filamentous phage particle encapsulating a genome according to the teachings of the present invention. In this embodiment, a DNA expression vector further contains a nucleotide sequence that defines a filamentous phage origin of replication such that the vector, upon presentation of the appropriate genetic complementation, can replicate as a filamentous phage in single stranded replicative form and be packaged into filamentous phage particles. This feature provides the ability of the DNA expression vector to be packaged into phage particles for subsequent segregation of the particle, and vector contained therein, away from other particles that comprise a population of phage particles.

A filamentous phage origin of replication is a region of the phage genome, as is well known, that defines sites for initiation of replication, termination of replication and packaging of the replicative form produced by replication. See, for example, Rasched et al., *Microbiol. Rev.,* 50:401–427 (1986); and Horiuchi, *J. Mol. Biol.,* 188:215–223 (1986).

A preferred filamentous phage origin of replication for use in the present invention is a M13, f1 or fd phage origin of replication. Particularly preferred is a filamentous phage origin of replication having a sequence shown in SEQ ID NO 90 and described by Short et al., *Nucl. Acids Res.,* 16:7583–7600 (1988). Preferred DNA expression vectors are the dicistronic expression vectors pComb8, pCKAB8, pComb2-8, pComb3, pCKAB3, pComb2-3 and pComb2-3' described in Example 1.

F. Methods for Producing a Library of Heterodimeric Receptors

1. General Rationale

In one embodiment the present invention provides a system for the simultaneous cloning and screening of pre-selected ligand-binding specificities from gene repertoires using the vectors described. This system provides linkage of cloning and screening methodologies and has several requirements. First, the expression of the polypeptide chains of a heterodimeric receptor in an in vitro expression host such as *E. coli* requires coexpression of the two polypeptide chains in order that a functional heterodimeric receptor can assemble to produce a receptor that binds ligand. Second, the screening of isolated members of the library for a preselected ligand-binding capacity requires a means to correlate (a linkage) the binding capacity of an expressed receptor molecule with a convenient means to isolate the gene that encodes the member from the library. Finally, a second heterologous fusion protein, comprised of a filamentous phage coat protein membrane anchor domain fused to an indicator polypeptide, is present on the surface of the phage to provide a means to screen the library for the presence of functional indicator, thereby simplifying the screening protocols.

Linkage of expression and screening is accomplished by the combination of targeting of a fusion polypeptide into the periplasm of a bacterial cell to allow assembly of a functional receptor with the targeting of the assembled receptor onto the coat of a filamentous phage particle during phage assembly to allow for convenient screening of the library member of interest. Periplasmic targeting is provided by the presence of a secretion signal domain in a fusion polypeptide of this invention. Targeting to a phage particle is provided by the presence of a filamentous phage coat protein membrane anchor domain (i.e., a cpIII- or cpVIII-derived membrane anchor domain) in a fusion polypeptide of this invention.

The preparation of libraries of antibodies has been described by others, and is exemplary of one component of this invention, namely the vectors and phages produced in libraries expressing heterodimeric receptors. See, for example the preparation of combinatorial antibody libraries on phagemids as described by Kang et al., *Proc. Natl. Acad. Sci., USA,* 88:4363–4366 (1991); Barbas et al, *Proc. Natl. Acad. Sci., USA,* 88:7978–7982 (1991); Zebedee et al, *Proc. Natl. Acad. Sci., USA,* 89:3175–3179 (1992); Kang et al, *Proc. Natl. Acad. Sci., USA,* 88:11120–11123 (1991); Barbas et al, *Proc. Natl. Acad. Sci., USA,* 89:4457–4461, (1992); and Gram et al, *Proc. Natl. Acad. Sci., USA,* 89:3576–3580 (1992), the disclosures of which are hereby incorporated by reference.

The present invention includes practicing a method for producing a library of DNA molecules, each DNA molecule comprising first and second cistrons for expressing first and second receptor polypeptides on the surface of a filamentous phage particle in the form of a heterodimeric receptor. The method generally comprises the steps of (a) forming a ligation admixture by combining in a ligation buffer (i) a repertoire of first receptor polypeptide-encoding genes and (ii) a plurality of DNA expression vectors in linear form adapted to form a first fusion polypeptide-expressing cistron, and (b) subjecting the admixture to ligation conditions for a time period sufficient for the repertoire of genes to become operatively linked (ligated) to the plurality of vectors to form the library. The process is repeated with a repertoire of second receptor polypeptide-encoding genes, ligating the genes into a second cistron of the vector to form a plurality of DNA vectors adapted to express the second receptor polypeptide, thereby forming a library that can express a heterodimeric receptor from a dicistronic vector.

The library so produced can be utilized for expression and screening of the expressed heterodimeric receptors encoded by the resulting library of dicistronic vectors represented in the library by the expression and screening methods described herein.

2. Production of Gene Repertoires

A gene repertoire is a collection of different genes, preferably polypeptide-encoding genes (polypeptide genes), and may be isolated from natural sources or can be generated artificially. Preferred gene repertoires are comprised of conserved genes. Particularly preferred gene repertoires comprise either or both genes that code for the members of a heterodimeric receptor molecule.

A gene repertoire useful in practicing the present invention contains at least $10^3$, preferably at least $10^4$, more preferably at least $10^5$, and most preferably at least $10^7$ different genes. Methods for evaluating the diversity of a repertoire of genes is well known to one skilled in the art.

Thus, in one embodiment, the present invention contemplates a method of isolating a pair of genes coding for a dimeric receptor having a preselected activity from a repertoire of conserved genes. Additionally, expressing the cloned pair of genes and isolating the resulting expressed dimeric receptor protein is also described. Preferably, the receptor will be a heterodimeric polypeptide capable of binding a ligand, such as an antibody molecule or immunologically active portion thereof, a cellular receptor, or a cellular adhesion protein coded for by one of the members of a family of conserved genes, i.e., genes containing a conserved nucleotide sequence of at least about 10 nucleotides in length.

Exemplary conserved gene families encoding different polypeptide chains of a dimeric receptor are those coding for immunoglobulins, major histocompatibility complex antigens of class I or II, lymphocyte receptors, integrins and the like.

Various well known methods can be employed to produce a useful gene repertoire. For instance, $V_H$ and $V_L$ gene repertoires can be produced by isolating $V_H$- and $V_L$-coding mRNA from a heterogeneous population of antibody producing cells, i.e., B lymphocytes (B cells), preferably rearranged B cells such as those found in the circulation or spleen of a vertebrate. Rearranged B cells are those in which immunoglobulin gene translocation, i.e., rearrangement, has occurred as evidenced by the presence in the cell of mRNA with the immunoglobulin gene V, D and J region transcripts adjacently located thereon. Typically, the B cells are collected in a 1–100 ml sample of blood which usually contains $10^6$ B cells/ml.

In some cases, it is desirable to bias a repertoire for a preselected activity, such as by using as a source of nucleic acid cells (source cells) from vertebrates in any one of various stages of age, health and immune response. For example, repeated immunization of a healthy animal prior to collecting rearranged B cells results in obtaining a repertoire enriched for genetic material producing a receptor of high affinity. Mullinax et al., *Proc. Natl. Acad. Sci., USA*, 87:8095–8099 (1990). Conversely, collecting rearranged B cells from a healthy animal whose immune system has not been recently challenged (i.e., a naive immune system) results in producing a repertoire that is not biased towards the production of high affinity $V_H$ and/or $V_L$ polypeptides.

It should be noted the greater the genetic heterogeneity of the population of cells for which the nucleic acids are obtained, the greater the diversity of the immunological repertoire (comprising $V_H$ - and $V_L$-coding genes) that will be made available for screening according to the method of the present invention. Thus, cells from different individuals, particularly those having an immunologically significant age difference, and cells from individuals of different strains, races or species can be advantageously combined to increase the heterogeneity (diversity) of a repertoire.

Thus, in one preferred embodiment, the source cells are obtained from a vertebrate, preferably a mammal, which has been immunized or partially immunized with an antigenic ligand (antigen) against which activity is sought, i.e., a preselected antigen. The immunization can be carried out conventionally. Antibody titer in the animal can be monitored to determine the stage of immunization desired, which stage corresponds to the amount of enrichment or biasing of the repertoire desired. Partially immunized animals typically receive only one immunization and cells are collected from those animals shortly after a response is detected. Fully immunized animals display a peak titer, which is achieved with one or more repeated injections of the antigen into the host mammal, normally at 2 to 3 week intervals. Usually three to five days after the last challenge, the spleen is removed and the genetic repertoire of the splenocytes, about 90% of which are rearranged B cells, is isolated using standard procedures. See, *Current Protocols in Molecular Biology*, Ausubel et al., eds., John Wiley & Sons, NY. Nucleic acids coding for $V_H$ and $V_L$ polypeptides can be derived from cells producing IgA, IgD, IgE, IgG or IgM, most preferably from IgM and IgG, producing cells.

Methods for preparing fragments of genomic DNA from which immunoglobulin variable region genes can be cloned as a diverse population are well known in the art. See for example Herrmann et al., *Methods In Enzymol.*, 152:180–183, (1987); Frischauf, *Methods In Enzymol.*, 152:183–190 (1987); Prischauf, *Methods In Enzymol.*, 152:190–199 (1987); and DiLella et al., *Methods In Enzymol.*, 152:199–212 (1987). (The teachings of the references cited herein are hereby incorporated by reference.)

The desired gene repertoire can be isolated from either genomic material containing the gene expressing the variable region or the messenger RNA (mRNA) which represents a transcript of the variable region. The difficulty in using the genomic DNA from other than non-rearranged B lymphocytes is in juxtaposing the sequences coding for the variable region, where the sequences are separated by introns. The DNA fragment(s) containing the proper exons must be isolated, the introns excised, and the exons then spliced in the proper order and in the proper orientation. For the most part, this will be difficult, so that the alternative technique employing rearranged B cells will be the method of choice because the V, D and J immunoglobulin gene regions have translocated to become adjacent, so that the sequence is continuous (free of introns) for the entire variable regions.

Where mRNA is utilized the cells will be lysed under RNase inhibiting conditions. In one embodiment, the first step is to isolate the total cellular mRNA. Poly A+ mRNA can then be selected by hybridization to an oligo-dT cellulose column. The presence of mRNAs coding for the heavy and/or light chain polypeptides can then be assayed by hybridization with DNA single strands of the appropriate genes. Conveniently, the sequences coding for the constant portion of the $V_H$ and $V_L$ can be used as polynucleotide probes, which sequences can be obtained from available sources. See for example, Early and Hood, *Genetic Engineering*, Setlow and Hollaender, eds., Vol. 3, Plenum Publishing Corporation, NY, (1981), pages 157–188; and Kabat et al., *Sequences of Immunological Interest*, National Institutes of Health, Bethesda, Md., (1987).

In preferred embodiments, the preparation containing the total cellular mRNA is first enriched for the presence of $V_H$ and/or $V_L$ coding mRNA. Enrichment is typically accomplished by subjecting the total mRNA preparation or partially purified mRNA product thereof to a primer extension reaction employing a polynucleotide synthesis primer as described herein. Exemplary methods for producing $V_H$ and $V_L$ gene repertoires using polynucleotide synthesis primers are described in PCT Application No. PCT/US 90/02836 (International Publication No. WO 90/14430). Particularly preferred methods for producing a gene repertoire rely on the use of preselected oligonucleotides as primers in a polymerase chain reaction (PCR) to form PCR reaction products as described herein.

In preferred embodiments, isolated B cells are immunized in vitro against a preselected antigen. In vitro immunization is defined as the clonal expansion of epitope-specific B cells in culture, in response to antigen stimulation. The end result is to increase the frequency of antigen-specific B cells in the immunoglobulin repertoire, and thereby decrease the number of clones in an expression library that must be screened to identify a clone expressing an antibody of the desired specificity. The advantage of in vitro immunization is that human monoclonal antibodies can be generated against a limitless number of therapeutically valuable antigens, including toxic or weak immunogens. For example, antibodies specific for the polymorphic determinants of tumor-associated antigens, rheumatoid factors, and histocompatibility antigens can be produced, which can not be elicited in immunized animals. In addition, it may be possible to generate immune responses which are normally suppressed in vivo.

In vitro immunization can be used to give rise to either a primary or secondary immune response. A primary immune response, resulting from first time exposure of a B cell to an antigen, results in clonal expansion of epitope-specific cells and the secretion of IgM antibodies with low to moderate apparent affinity constants ($10^6$–$10^8$ $M^{-1}$). Primary immunization of human splenic and tonsillar lymphocytes in culture can be used to produce monoclonal antibodies against a variety of antigens, including cells, peptides, macromolecule, haptens, and tumor-associated antigens. Memory B cells from immunized donors can also be stimulated in culture to give rise to a secondary immune response characterized by clonal expansion and the production of high affinity antibodies (>$10^9$ $M^{-1}$) of the IgG isotype, particularly against viral antigens by clonally expanding sensitized lymphocytes derived from seropositive individuals.

3. Preparation of Polynucleotide Primers for Producing Immunoglobulin Gene Repertoires $V_H$ and $V_L$ gene repertoires can be separately prepared prior to their utilization in the present invention. Repertoire preparation is typically accomplished by primer extension, preferably by primer extension in a polymerase chain reaction (PCR) format.

To produce a repertoire of $V_H$-coding DNA homologs by primer extension, the nucleotide sequence of a primer is selected to hybridize with a plurality of immunoglobulin heavy chain genes at a site substantially adjacent to the $V_H$-coding region so that a nucleotide sequence coding for a functional (capable of binding) polypeptide is obtained. To hybridize to a plurality of different $V_H$-coding nucleic acid strands, the primer must be a substantial complement of a nucleotide sequence conserved among the different strands. Such sites include nucleotide sequences in the constant region, any of the variable region framework regions, preferably the third framework region, leader region, promoter region, J region and the like.

If the repertoires of $V_H$-coding and $V_L$-coding DNA homologs are to be produced by (PCR) amplification, two primers, i.e., a PCR primer pair, must be used for each coding strand of nucleic acid to be amplified.

In PCR, each primer works in combination with a second primer to amplify a target nucleic acid sequence. The choice of PCR primer pairs for use in PCR is governed by considerations as discussed herein for producing gene repertoires. That is, the primers have a nucleotide sequence that is complementary to a sequence conserved in the repertoire. Useful $V_H$ and $V_L$ priming sequences are shown in Tables 5 and 6, herein below.

4. Polymerase Chain Reaction to Produce Gene Repertoires

The strategy used for cloning the $V_H$ and $V_L$ genes contained within a repertoire will depend, as is well known in the art, on the type, complexity, and purity of the nucleic acids making up the repertoire. Other factors include whether or not the genes are contained in one or a plurality of repertoires and whether or not they are to be amplified and/or mutagenized.

The $V_H$- and $V_L$-coding gene repertoires are comprised of polynucleotide coding strands, such as mRNA and/or the sense strand of genomic DNA. If the repertoire is in the form of double stranded genomic DNA, it is usually first denatured, typically by melting, into single strands. A repertoire is subjected to a PCR reaction by treating (contacting) the repertoire with a PCR primer pair, each member of the pair having a preselected nucleotide sequence. The PCR primer pair is capable of initiating primer extension reactions by hybridizing to nucleotide sequences, preferably at least about 10 nucleotides in length and more preferably at least about 20 nucleotides in length, conserved within the repertoire. The first primer of a PCR primer pair is sometimes referred to herein as the "sense primer" because it hybridizes to the coding or sense strand of a nucleic acid. In addition, the second primer of a PCR primer pair is sometimes referred to herein as the "anti-sense primer" because it hybridizes to a non-coding or anti-sense strand of a nucleic acid, i.e., a strand complementary to a coding strand.

The PCR reaction is performed by mixing the PCR primer pair, preferably a predetermined amount thereof, with the nucleic acids of the repertoire, preferably a predetermined amount thereof, in a PCR buffer to form a PCR reaction admixture. The admixture is maintained under polynucleotide synthesizing conditions for a time period, which is typically predetermined, sufficient for the formation of a PCR reaction product, thereby producing a plurality of different $V_H$-coding and/or $V_L$-coding DNA homologs.

A plurality of first primer and/or a plurality of second primers can be used in each amplification, e.g., one species of first primer can be paired with a number of different second primers to form several different primer pairs. Alternatively, an individual pair of first and second primers can be used. In any case, the amplification products of amplifications using the same or different combinations of first and second primers can be combined to increase the diversity of the gene library.

PCR amplification methods are described in detail in U.S. Pat. Nos. 4,683,195, 4,683,202, 4,800,159, and 4,965,188, and at least in several texts including "PCR Technology: Principles and Applications for DNA Amplification", H. Erlich, ed., Stockton Press, New York (1989); and "PCR Protocols: A Guide to Methods and Applications", Innis et al., eds., Academic Press, San Diego, Calif. (1990).

5. Preparation of Dicistronic Gene Libraries

In practicing the present invention, a library of dicistronic DNA molecules capable of expressing heterodimeric receptors on phagemids is prepared. A dicistronic DNA molecule is a single DNA molecule having the capacity to express two separate polypeptides from two separate cistrons. Each dicistronic molecule is capable of expressing first and second polypeptides from first and second cistrons, respectively, that can form, in a suitable host, a heterodimeric receptor on the surface of a filamentous phage particle.

The method for producing a library of dicistronic DNA molecules comprises the steps of:
 (a) Forming a first ligation admixture by combining in a ligation buffer:
  (i) a repertoire of first polypeptide genes in the form of dsDNA, each having cohesive termini adapted for directional ligation, and (ii) a plurality of DNA expression vectors in linear form, each having upstream and downstream first cohesive termini that are (a) adapted for directionally receiving the first polypeptide genes in a common reading frame, and (b) operatively linked to respective upstream and downstream translatable DNA sequences. The upstream translatable DNA sequence encodes a pelB secretion signal, the downstream translatable DNA sequence encodes a filamentous phage coat protein membrane anchor, and translatable DNA sequences are operatively linked to respective upstream and downstream DNA expression control sequences.

(b) Subjecting the admixture to ligation conditions for a time period sufficient to operatively link the first polypeptide genes to the vectors and produce a plurality of circular DNA molecules each having a first cistron for expressing the first polypeptide.

(c) Treating the plurality of circular DNA molecules under DNA cleavage conditions to produce a plurality of DNA expression vectors in linear form that each have upstream and downstream second cohesive termini that are (i) adapted for directionally receiving a repertoire of second polypeptide genes in a common reading frame, and (ii) operatively linked to respective upstream and downstream DNA sequences. The upstream DNA sequence is a translatable sequence encoding a secretion signal, the downstream DNA sequence has at least one stop codon in the reading frame, and the translatable DNA sequence is operatively linked to a DNA expression control sequence.

(d) Forming a second ligation admixture by combining in a ligation buffer:
  (i) the plurality of DNA expression vectors formed in step (c), and
  (ii) the repertoire of second polypeptide genes in the form of dsDNA, each having cohesive termini adapted for directional ligation to the plurality of DNA expression vectors; and (e) Subjecting the second admixture to ligation conditions for a time period sufficient to operatively link the second polypeptide genes to said vectors and produce a plurality of circular DNA molecules each having the second cistron for expressing the second polypeptide, thereby forming the library.

In preferred embodiments a secretion signal is a pelB secretion signal. Also preferred is the use of a filamentous phage membrane anchor that is derived from cpIII or cpVIII as described herein.

DNA expression vectors useful for practicing the above method are the dicistronic expression vectors described in greater detail before.

In practicing the method of producing a library of dicistronic DNA molecules, it is preferred that the upstream and downstream first cohesive termini do not have the same nucleotide sequences as the upstream and downstream second cohesive termini. In this embodiment, the treating step (c) to linearize the circular DNA molecules typically involves the use of restriction endonucleases that are specific for producing said second termini, but do not cleave the circular DNA molecule at the sites that formed the first termini. Exemplary and preferred first and second termini are the termini defined by cleavage of pCBAK8 with Xho I and Spe I to form the upstream and downstream first termini, and defined by cleavage of pCBAK8 with Sac I and Xba I to form the upstream and downstream second termini. In this embodiment, other pairs of cohesive termini can be utilized at the respective pairs of first and second termini, so long as the four termini are each distinct, non-complementary termini. Exemplary are the termini found on the vectors pComb3, pComb2-3, pComb2-3', pComb8 and pComb2-8 described herein.

Methods of treating the plurality of circular DNA molecules under DNA cleavage conditions to form linear DNA molecules are generally well known and depend on the nucleotide sequence to be cleaved and the mechanism for cleavage. Preferred treatments involve admixing the DNA molecules with a restriction endonuclease specific for a endonuclease recognition site at the desired cleavage location in an amount sufficient for the restriction endonuclease to cleave the DNA molecule. Buffers, cleavage conditions, and substrate concentrations for restriction endonuclease cleavage are well known and depend on the particular enzyme utilized. Exemplary restriction enzyme cleavage conditions are described in Example 2.

G. Diagnostic Systems

The present invention also describes a diagnostic system, preferably in kit form, for assaying for the presence of a preselected ligand, or antigen, in a sample where it is desirable to detect the presence, and preferably the amount, of the ligand or antigen in a sample according to the diagnostic methods described herein.

The sample can be a tissue, tissue extract, tissue section, fluid sample or body fluid sample, such as blood, plasma or serum. The sample can also be present on a chromatographic medium, paper or fabric, such as the product of a Western Blot, and the like.

The diagnostic system includes, in an amount sufficient to perform at least one assay, a filamentous phage comprising on its surface a ligand-binding heterodimeric receptor and an indicator fusion polypeptide according to the present invention, as a separately packaged reagent.

Exemplary diagnostic systems for detecting a preselected ligand and utilizing a filamentous phage of this invention are described in the Examples.

Instructions for use of the packaged reagent(s) are also typically included.

As used herein, the term "package" refers to a solid matrix or material such as glass, plastic (e.g., polyethylene, polypropylene or polycarbonate), paper, foil and the like capable of holding within fixed limits a filamentous phage or library of phage of the present invention. Thus, for example, a package can be a glass vial used to contain milligram quantities of a contemplated labeled phage preparation, or it can be a microtiter plate well to which microgram quantities of a contemplated phage particle(s) have been operatively affixed, i.e., linked so as to be capable of binding a ligand.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

A diagnostic system of the present invention preferably also includes a indicating means capable of signaling the formation of a binding reaction complex containing a phage complexed with the preselected ligand.

The word "complex" as used herein refers to the product of a specific binding reaction such as an phage-ligand or receptor-ligand reaction. Exemplary complexes are immunoreaction products.

As used herein, the term "indicating means" refers to additional reagents required to visualize the fact that a receptor-ligand complex (immunoreactant) has formed.

Such additional reagents for alkaline phosphatase (Apase) include para-nitro-phenyl phosphate (PNPP) and the like detectable substrates, and additional reagents, for horseradish peroxidase (HRP) include hydrogen peroxide and an oxidation dye precursor such as diaminobenzidine. An additional reagent useful with glucose oxidase is 2,2'-amino-di-(3-ethyl-benzthiazoline-G-sulfonic acid) (ABTS).

The diagnostic kits of the present invention can be used in an "ELISA" format to detect the quantity of a preselected ligand in a sample. "ELISA" refers to an enzyme-linked immunosorbent assay that employs an antibody or antigen bound to a solid phase and an enzyme-antigen or enzyme-antibody conjugate to detect and quantify the amount of an antigen present in a sample and is readily applicable to the present methods. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. No. 3,654,090; U.S. Pat. No. 3,850,752; and U.S. Pat. No. 4,016,043, which are all incorporated herein by reference.

Thus, in some embodiments, a polypeptide, ligand, antigen, or a phage of the present invention can be affixed to a solid matrix to form a solid support that comprises a package in the subject diagnostic systems.

A reagent is typically affixed to a solid matrix by adsorption from an aqueous medium although other modes of affixation applicable to proteins and polypeptides can be used that are well known to those skilled in the art. Exemplary adsorption methods are described herein.

Useful solid matrices are also well known in the art. Such materials are water insoluble and include the cross-linked dextran available under the trademark "SEPHADEX" from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, or indicating means of any diagnostic system described herein can be provided in solution, as a liquid dispersion or as a substantially dry power, e.g., in lyophilized form. Where the indicating means is an enzyme substrate, the substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems.

H. Assay Methods

The present invention contemplates various assay methods for determining the presence, and preferably amount, of a preselected ligand, typically present in an aqueous composition such as a biological fluid sample using a phage or plurality of phages of this invention as a ligand-binding reagent to form a binding reaction product whose amount relates, either directly or indirectly, to the amount of the preselected ligand in the sample.

Those skilled in the art will understand that there are numerous well known clinical diagnostic chemistry procedures in which a binding reagent of this invention can be used to form an binding reaction product whose amount relates to the amount of the ligand in a sample. Thus, while exemplary assay methods are described herein, the invention is not so limited.

Various heterogenous and homogeneous protocols, either competitive or noncompetitive, can be employed in performing an assay method of this invention.

In one embodiment, the invention contemplates a direct binding assay using a phage containing a ligand-binding heterodimeric receptor of this invention as a binding reagent to detect the presence of a preselected ligand with which the receptor binds. The method comprises the steps of a) admixing (contacting) a sample suspected to contain a preselected antigen with a filamentous phage particle of this invention that binds to the preselected ligand under binding conditions sufficient for the phage surface-accessible heterodimeric receptor to bind the ligand and form a ligand-phage complex; b) maintaining the admixture under binding reaction conditions sufficient for the heterodimeric receptor on the phage particle to bind to the ligand an form a ligand-phage complex; and c) detecting the presence of the ligand-phage complex. Typically, the detection of complex is conducted by detecting the indicating polypeptide present in the complex, thereby detecting the preselected ligand.

Binding conditions are those that maintain the ligand-binding activity of the receptor. Those conditions include a temperature range of about 4 to 50 degrees Centigrade, a pH value range of about 5 to 9 and an ionic strength varying from about that of distilled water to that of about one molar sodium chloride.

The detecting step can be directed, as is well known in the immunological arts, to either the complex or the binding reagent (the receptor component of the complex), although direct detection of the indicating polypeptide by measuring indicator activity is the preferred detection method. However, a secondary binding reagent such as an antibody specific for the receptor may be utilized.

Methods for detecting the presence, and preferably amount, of an indicator polypeptide are generally well unknown in the immunological arts and will not be discussed in detail herein.

A further diagnostic method utilizes the multivalency of a filamentous phage particle to cross-link ligand, thereby forming an aggregation of multiple ligands and phage particles, producing a precipitable aggregate. This embodiment is comparable to the well known methods of immune precipitation. This embodiment comprises the steps of admixing a sample with a plurality of phage particle of this invention to form a binding admixture under binding conditions, followed by a separation step to isolate the formed binding complexes. Typically, isolation is accomplished by centrifugation or filtration to remove the aggregate from the admixture. The presence of binding complexes indicates the presence of the preselected ligand to be detected. The presence of aggregates or complexes can be detected by detecting activity of the indicator polypeptide.

EXAMPLES

The following examples are intended to illustrate, but not limit, the scope of the invention.

1. Construction of a Dicistronic Expression Vector for Producing a Heterodimeric Receptor on Phage Particles To obtain a vector system for generating a large number of Fab antibody fragments that can be screened directly, expression libraries in bacteriophage Lambda have previously been constructed as described in Huse et al., *Science*, 246:1275–1281 (1989). These systems did not contain design features that provide for the expressed Fab to be targeted to the surface of a filamentous phage particle.

The main criterion used in choosing a vector system was the necessity of generating the largest number of Fab fragments which could be screened directly. Bacteriophage Lambda was selected as the starting point to develop an expression vector for three reasons. First, in vitro packaging of phage DNA was the most efficient method of reintroducing DNA into host cells. Second, it was possible to detect protein expression at the level of single phage plaques. Finally, the screening of phage libraries typically involved less difficulty with nonspecific binding. The alternative, plasmid cloning vectors, are only advantageous in the analysis of clones after they have been identified. This advantage was not lost in the present system because of the use of a dicistronic expression vector such as pCombVIII, thereby permitting a plasmid containing the heavy chain, light chain, or Fab expressing inserts to be excised.

a. Construction of Dicistronic Expression Vector pCOMB (i) Preparation of Lambda ZaP ™II Lambda Zap™ II is a derivative of the original Lambda Zap (ATCC Accession Number 40,298) that maintains all of the characteristics of the original Lambda Zap including 6 unique cloning sites, fusion protein expression, and the ability to rapidly excise the insert in the form of a phagemid (Bluescript SK-), but lacks the SAM 100 mutation, allowing growth on many Non-Sup F strains, including XL1-Blue. The "LAMBDA ZAP" II was constructed as described in Short et al., *Nuc. Acids Res.,* 16:7583–7600, (1988), by replacing the Lambda S gene contained in a 4254 base pair (bp) DNA fragment produced by digesting Lambda Zap with the restriction enzyme Nco I. This 4254 bp DNA fragment was replaced with the 4254 bp DNA fragment containing the Lambda S gene isolated from Lambda gt10 (ATCC Accession Number 40,179) after digesting the vector with the restriction enzyme Nco I. The 4254 bp DNA fragment isolated from lambda gt10 was ligated into the original Lambda Zap vector using T4 DNA ligase and standard protocols such as those described in *Current Protocols in Molecular Biology,* Ausubel et al., eds., John Wiley and Sons, NY, 1987, to form ,"LAMBDA ZAP" II.

(ii) Preparation of Lambda Hc2

To express a plurality of $V_H$-coding DNA homologs in an *E. coli* host cell, a vector designated Lambda Hc2 was constructed. The vector provided the following: the capacity to place the $V_H$-coding DNA homologs in the proper reading frame; a ribosome binding site as described by Shine et al., *Nature,* 254:34, 1975; a leader sequence directing the expressed protein to the periplasmic space designated the pelB secretion signal; a polynucleotide sequence that coded for a known epitope (epitope tag); and also a polynucleotide that coded for a spacer protein between the $V_H$-coding DNA homolog and the polynucleotide coding for the epitope tag.

Lambda Hc2 has been previously described by Huse et al., *Science,* 246:1275–1281 (1989).

To prepare Lambda Hc2, a synthetic DNA sequence containing all of the above features was constructed by designing single stranded polynucleotide segments of 20–40 bases that would hybridize to each other and form the double stranded synthetic DNA sequence shown in FIG. 1. The individual single-stranded polynucleotide segments are shown in Table 3.

Polynucleotides N2, N3, N9-4, N11, N10-5, N6, N7 and N8 (Table 3) were kinased by adding 1 microliter (ul) of each polynucleotide 0.1 micrograms/microliter (ug/ul) and 20 units of $T_4$ polynucleotide kinase to a solution containing 70 mM Tris-HCl at pH 7.6, 10 mM $MgCl_2$, 5 mM dithiothreitol (DTT), 10 mM beta-mercaptoethanol and 500 micrograms per milliliter (ug/ml) bovine serum albumin (BSA). The solution was maintained at 37 degrees Centigrade (37 C.) for 30 minutes and the reaction stopped by maintaining the solution at 65 C. for 10 minutes. The two end polynucleotides, 20 ng of polynucleotides N1 and polynucleotides N12, were added to the above kinasing reaction solution together with ¹⁄₁₀ volume of a solution containing 20 mM Tris-HCl at pH 7.4, 2 mM $MgCl_2$ and 50 mM NaCl. This solution was heated to 70 C. for 5 minutes and allowed to cool to room temperature, approximately 25 C., over 1.5 hours in a 500 ml beaker of water. During this time period all 10 polynucleotides annealed to form the double stranded synthetic DNA insert shown in FIG. 3. The individual polynucleotides were covalently linked to each other to stabilize the synthetic DNA insert by adding 40 ul of the above reaction to a solution containing 50 mM Tris-HCl, pH 7.5, 7 mM $MgCl_2$, 1 mM DTT, 1 mM adenosine triphosphate (ATP) and 10 units of T4 DNA ligase. This solution was maintained at 37 C. for 30 minutes and then the T4 DNA ligase was inactivated by maintaining the solution at 65 C. for 10 minutes. The end polynucleotides were kinased by mixing 52 ul of the above reaction, 4 ul of a solution containing 10 mM ATP and 5 units of T4 polynucleotide kinase. This solution was maintained at 37 C. for 30 minutes and then the T4 polynucleotide kinase was inactivated by maintaining the solution at 65 C. for 10 minutes.

TABLE 3

| SEQ. ID. NO.: | | |
|---|---|---|
| (22) N1) | 5' | GGCCGCAAATTCTATTTCAAGGAGACAGTCAT 3' |
| (23) N2) | 5' | AATGAAATACCTATTGCCTACGGCAGCCGCTGGATT 3' |
| (24) N3) | 5' | GTTATTACTCGCTGCCCAACCAGCCATGGCCC 3' |
| (25) N6) | 5' | CAGTTTCACCTGGGCCATGGCTGGTTGGG 3' |
| (26) N7) | 5' | CAGCGAGTAATAACAATCCAGCGGCTGCCGTAGGCAATAG 3' |
| (27) N8) | 5' | GTATTTCATTATGACTGTCTCCTTGAAATAGAATTTGC 3' |
| (28) N9-4) | 5' | AGGTGAAACTGCTCGAGATTTCTAGACTAGTTACCCGTAC 3' |
| (29) N10-5) | 5' | CGGAACGTCGTACGGGTAACTAGTCTAGAAATCTCGAG 3' |
| (30) N11) | 5' | GACGTTCCGGACTACGGTTCTTAATAGAATTCG 3' |
| (31) N12) | 5' | TCGACGAATTCTATTAAGAACCGTAGTC 3' |

The completed synthetic DNA insert was ligated directly into the "LAMBDA ZAP" II vector described in Example 1a(i) that had been previously digested with the restriction enzymes, Not I and Xho I. The ligation mixture was packaged according to the manufacture's instructions using Gigapack II Gold packing extract available from Stratagene, La Jolla, Calif. The packaged ligation mixture was plated on XL1-Blue cells (Stratagene). Individual lambda plaques were cored and the inserts excised according to the in vivo excision protocol for "LAMBDA ZAP" II provided by the manufacturer (Stratagene). This in vivo excision protocol moved the cloned insert from the Lambda Hc2 vector into a phagemid vector to allow easy for manipulation and sequencing. The accuracy of the above cloning steps was confirmed by sequencing the insert using the Sanger dideoxy method described in by Sanger et al., *Proc. Natl. Acad. Sci., USA,* 74:5463–5467, (1977) and using the manufacture's instructions in the AMV Reverse Transcriptase $^{35}$S-ATP sequencing kit (Stratagene). The sequence of the resulting double-stranded synthetic DNA insert in the $V_H$ expression vector (Lambda Hc2) is shown in FIG. 1. The sequence of each strand (top and bottom) of Lambda Hc2 is listed in the sequence listing as SEQ ID NO:1 and SEQ ID NO:2, respectively. The resultant Lambda Hc2 expression vector is shown in FIG. 2.

(iii) Preparation of Lambda Lc2

To express a plurality of $V_L$-coding DNA homologs in an *E. coli* host cell, a vector designated Lambda Lc2 was constructed having the capacity to place the $V_L$-coding DNA homologs in the proper reading frame, provided a ribosome binding site as described by Shine et al., *Nature,* 254:34 (1975), provided the pelB gene leader sequence secretion signal that has been previously used to successfully secrete Fab fragments in *E. coli* by Lei et al., *J. Bac.,* 169:4379 (1987) and Better et al., *Science,* 240:1041 (1988), and also provided a polynucleotide containing a restriction endonuclease site for cloning. Lambda Lc2 has been previously described by Huse et al., *Science,* 246:1275–1281 (1989).

A synthetic DNA sequence containing all of the above features was constructed by designing single stranded polynucleotide segments of 20–60 bases that would hybridize to each other and form the double stranded synthetic DNA sequence shown in FIG. 3. The sequence of each individual single-stranded polynucleotide segment (01-08) within the double stranded synthetic DNA sequence is shown in Table 4.

Polynucleotides 02, 03, 04, 05, 06 and 07 (Table 4) were kinased by adding 1 ul (0.1 ug/ul) of each polynucleotide and 20 units of $T_4$ polynucleotide kinase to a solution containing 70 mM Tris-HCl at pH 7.6, 10 mM MgCl, 5 mM DTT, 10 mM beta-mercaptoethanol and 500 mg/ml of BSA. The solution was maintained at 37 C. for 30 minutes and the reaction stopped by maintaining the solution at 65° C. for 10 minutes. The 20 ng each of the two end polynucleotides, 01 and 08, were added to the above kinasing reaction solution together with 1/10 volume of a solution containing 20 mM Tris-HCl at pH 7.4, 2 mM MgCl and 15 mM sodium chloride (NaCl). This solution was heated to 70 C. for 5 minutes and allowed to cool to room temperature, approximately 25 C., over 1.5 hours in a 500 ml beaker of water. During this time period all 8 polynucleotides annealed to form the double stranded synthetic DNA insert shown in FIG. 3.

The individual polynucleotides were covalently linked to each other to stabilize the synthetic DNA insert by adding 40 ul of the above reaction to a solution containing 50 ml Tris-HCl at pH 7.5, 7 ml MgCl, 1 mm DTT, 1 mm ATP and 10 units of T4 DNA ligase. This solution was maintained at 37 C. for 30 minutes and then the T4 DNA ligase was inactivated by maintaining the solution at 65 C. for 10 minutes. The end polynucleotides were kinased by mixing 52 ul of the above reaction, 4 ul of a solution containing 10 mM ATP and 5 units of T4 polynucleotide kinase. This solution was maintained at 37 C. for 30 minutes and then the T4 polynucleotide kinase was inactivated by maintaining the solution at 65 C. for 10 minutes.

TABLE 4

| SEQ ID NO: | | |
|---|---|---|
| (32) 01) | 5' | TGAATTCTAAACTAGTCGCCAAGGAGACAGTCAT 3' |
| (33) 02) | 5' | AATGAAATACCTATTGCCTACGGCAGCCGCTGGATT 3' |
| (34) 03) | 5' | GTTATTACTCGCTGCCCAACCAGCCATGGCC 3' |
| (35) 04) | 5' | GAGCTCGTCAGTTCTAGAGTTAAGCGGCCG 3' |
| (36) 05) | 5' | GTATTTCATTATGACTGTCTCCTTGGCGACTAGTTTAGAATTCAAGCT 3' |
| (37) 06) | 5' | CAGCGAGTAATAACAATCCAGCGGCTGCCGTAGGCAATAG 3' |
| (38) 07) | 5' | TGACGAGCTCGGCCATGGCTGGTTGGG 3' |
| (39) 08) | 5' | TCGACGGCCGCTTAACTCTAGAAC 3' |

The completed synthetic DNA insert was ligated directly into the "LAMBDA ZAP" II vector described in Example 1(a)(i) that had been previously digested with the restriction enzymes Sac I and Xho I. The ligation mixture was packaged according to the manufacture's instructions using Gigapack II Gold packing extract (Stratagene). The packaged ligation mixture was plated on XL1-Blue cells (Stratagene). Individual lambda plaques were cored and the inserts excised according to the in vivo excision protocol for "LAMBDA ZAP" II provided by the manufacturer (Stratagene). This in vivo excision protocol moved the cloned insert from the Lambda Lc2 vector into a plasmid phagemid vector allow for easy manipulation and sequencing. The accuracy of the above cloning steps was confirmed by sequencing the insert using the manufacture's instructions in the AMV Reverse Transcriptase $^{35}$S-dATP sequencing kit (Stratagene). The sequence of the resulting Lc2 expression vector (Lambda Lc2) is shown in FIG. 3. Each strand is separately listed in the Sequence Listing as SEQ ID NO:3 and SEQ ID NO:4. The resultant Lc2 vector is schematically diagrammed in FIG. 4.

A preferred vector for use in this invention, designated Lambda Lc3, is a derivative of Lambda Lc2 prepared above. Lambda Lc2 contains a Spe I restriction site (ACTAGT) located 3' to the EcoR I restriction site and 5' to the Shine-Dalgarno ribosome binding site as shown in the sequence in FIG. 3 and in SEQ ID NO 3. A Spe I restriction site is also present in Lambda Hc2 as shown in FIGS. 1 and 2 and in SEQ ID NO 1. A combinatorial vector, designated pComb, was constructed by combining portions of Lambda Hc2 and Lc2 together as described in Example 1a(iv) below. The resultant combinatorial pComb vector contained two Spe I restriction sites, one provided by Lambda Hc2 and one provided by Lambda Lc2, with an EcoR I site in between. Despite the presence of two Spe I restriction sites, DNA homologs having Spe I and EcoR I cohesive termini were successfully directionally ligated into a pComb expression vector previously digested with Spe I and EcoR I as described in Example 1b below. The proximity of the EcoR I restriction site to the 3' Spe I site, provided by the Lc2 vector, inhibited the complete digestion of the 3' Spe I site. Thus, digesting pComb with Spe I and EcoR I did not result in removal of the EcoR I site between the two Spe I sites.

The presence of a second Spe I restriction site may be undesirable for ligations into a pComb vector digested only with Spe I as the region between the two sites would be eliminated. Therefore, a derivative of Lambda Lc2 lacking the second or 3' Spe I site, designated Lambda Lc3, is produced by first digesting Lambda Lc2 with Spe I to form a linearized vector. The ends are filled in to form blunt ends which are ligated together to result in Lambda Lc3 lacking a Spe I site. Lambda Lc3 is a preferred vector for use in constructing a combinatorial vector as described below.

(iv) Preparation of pComb

Phagemids were excised from the expression vectors Lambda Hc2 or Lambda Lc2 using an in vivo excision protocol described above. Double stranded DNA was prepared from the phagemid-containing cells according to the methods described by Holmes et al., Anal. Biochem., 114:193 (1981). The phagemids resulting from in vivo excision contained the same nucleotide sequences for antibody fragment cloning and expression as did the parent vectors, and are designated phagemid Hc2 and Lc2, corresponding to Lambda Hc2 and Lc2, respectively.

For the construction of combinatorial phagemid vector pComb, produced by combining portions of phagemid Hc2 and phagemid Lc2, phagemid Hc2 was first digested with Sac I to remove the restriction site located 5' to the LacZ promoter. The linearized phagemid was then blunt ended with T4 polymerase and ligated to result in a Hc2 phagemid lacking a Sac I site. The modified Hc2 phagemid and the Lc2 phagemid were then separately restriction digested with Sca I and EcoR I to result in a Hc2 fragment having from 5' to 3' Sca I, Not I Xho I, Spe I and EcoR I restriction sites and a Lc2 fragment having from 5' to 3' EcoR I, Sac I, Xba I and Sac I restriction sites. The linearized phagemids were then ligated together at their respective cohesive ends to form pComb, a circularized phagemid having a linear arrangement of restriction sites of Not I, Xho I, Spe I, EcoR I, Sac I, Xba I, Not I, Apa I and Sca I. The ligated phagemid vector was then inserted into an appropriate bacterial host and transformants were selected on the antibiotic ampicillin.

Figure 5:
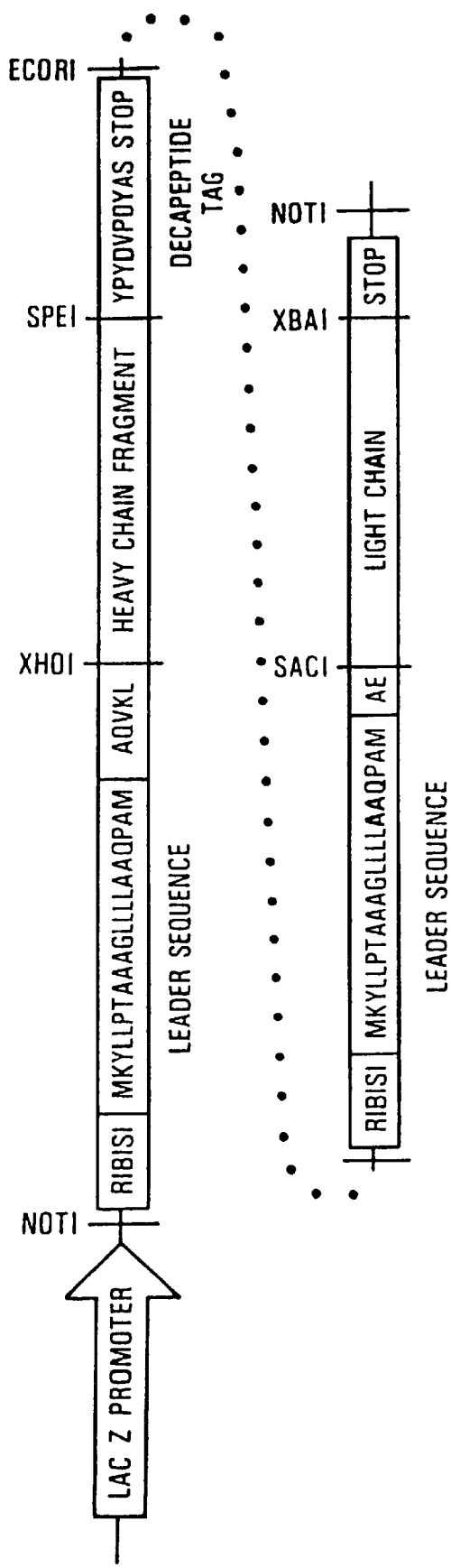
FIG. 5 illustrates the dicistronic expression vector, pComb, in the form of a phagemid expression vector. To produce pComb, phagemids were first excised from the expression vectors, Lambda Hc2 and Lambda Lc2, using an in vivo excision protocol according to manufacturers instructions (Stratagene, La Jolla, Calif.). The pComb expression vector is prepared from Lambda Hc2 and Lambda Lc2 which do not contain $V_H$-coding or $V_L$-coding DNA homologs. The in vivo excision protocol moved the cloned insert from the Lambda Hc2 and Lc2 vectors into a phagemid vector. The resultant phagemids contained the same nucleotide sequences for antibody fragment cloning and expression as did the parent vectors. Hc2 and Lc2 phagemid expression vectors were separately restriction digested with Sca I and EcoR I. The linearized phagemids were ligated via the Sca I and EcoR I cohesive termini to form the dicistronic (combinatorial) vector, pComb.

Selected ampicillin resistant transformants were screened for the presence of two Not I sites. The resulting ampicillin resistant combinatorial phagemid vector was designated pComb, the schematic organization of which is shown in FIG. 5. The resultant combinatorial vector, pComb, consisted of a DNA molecule having two cassettes to express two fusion proteins and having nucleotide residue sequences for the following operatively linked elements listed in a 5' to 3' direction: a first cassette consisting of an inducible LacZ promoter upstream from the LacZ gene; a Not I restriction site; a ribosome binding site; a pelB leader; a spacer; a cloning region bordered by a 5' Xho and 3' Spe I restriction site; a decapeptide tag followed by expression control stop sequences; an EcoR I restriction site located 5' to a second cassette consisting of an expression control ribosome binding site; a pelB leader; a spacer region; a cloning region bordered by a 5' Sac I and a 3' Xba I restriction site followed by expression control stop sequences and a second Not I restriction site.

A preferred combinatorial vector for use in this invention, designated pComb2, is constructed by combining portions of phagemid Hc2 and phagemid Lc3 as described above for preparing pComb. The resultant combinatorial vector, pComb2, consists of a DNA molecule having two cassettes identical to pComb to express two fusion proteins identically to pComb except that a second Spe I restriction site in the second cassette is eliminated.

b. Construction of Vectors pCombVIII and pCombIII for Expressing Fusion Proteins Having a Bacteriophage Coat Protein Membrane Anchor Because of the multiple endonuclease restriction cloning sites, the pComb phagemid expression vector prepared above is a useful cloning vehicle for modification for the preparation of an expression vector of this invention. To that end, pComb is digested with EcoR I and Spe I followed by phosphatase treatment to produce linearized pComb.

(i) Preparation of pCombVIII

A PCR product produced in Example 2g and having a nucleotide sequence that defines a filamentous bacteriophage coat protein VIII (cpVIII) membrane anchor domain and cohesive Spe I and EcoR I termini was admixed with the linearized pComb to form a ligation admixture. The cpVIII-membrane anchor-encoding PCR fragment was directionally ligated into the pComb phagemid expression vector at corresponding cohesive termini, that resulted in forming pCombVIII (also designated pComb8). pCombVIII contains a cassette defined by the nucleotide sequence shown in SEQ ID NO:89 from nucleotide base 1 to base 208, and contains a pelB secretion signal operatively linked to the cpVIII membrane anchor.

A preferred phagemid expression vector for use in this invention, designated either pComb2-VIII or pComb2-8, was prepared as described above by directionally ligating the cpVIII membrane anchor-encoding PCR fragment into a pComb2 phagemid expression vector via Spe I and EcoR I cohesive termini. The pComb2-8 had only one Spe I restriction site.

(ii) Preparation of pCombIII

A separate phagemid expression vector was constructed using sequences encoding bacteriophage cpIII membrane anchor domain. A PCR product defining the cpIII membrane anchor containing a LacZ promotor region sequence 3' to the membrane anchor for expression of the light chain and Spe I and EcoR I cohesive termini was prepared as described for cpVIII, the details of which are described in Example 2g. The cpIII-derived PCR product was then ligated into linearized pComb2 vector having only one Spe I site to form the vector pComb2-3 (also designated pComb2-III).

A more preferred phagemid expression vector for use in this invention having additional restriction enzyme cloning sites, designated pComb-III' or pComb2-3', was prepared as described above for pComb2-3 with the addition of a 51 base pair fragment from pBluescript as described by Short et al., Nuc. Acids Res., 16:7583–7600 (1988) and commercially available from Stratagene. To prepare pComb2-3', pComb2-3 was first digested with Xho I and Spe I restriction enzymes to form a linearized pComb2-3. The vector pBluescript was digested with the same enzymes releasing a 51 base pair fragment containing the restriction enzyme sites Sal I, Acc I, Hinc II, Cla I, Hind III, EcoR V, Pst I, Sma I and BamH I. The 51 base pair fragment was ligated into the linearized pComb2-3 vector via the cohesive Xho I and Spe I termini to form pComb2-3'.

c. Construction of pCBAK Vectors Having a Chloramphenicol Resistance Marker

In order to utilize a different selectable marker gene, such as chloramphenicol acetyl transferase (CAT), for the selection of bacteria transformed with a vector of this invention, expression vectors based on pComb were developed having a gene encoding CAT and are designated pCBAK vectors. The pCBAK vectors are prepared by combining portions of pCB and pComb.

(i) Preparation of pCB pBlueScript phagemid vectors, pBC SK(−) and pBS SK(−), (Stratagene), were modified and combined to generate a third vector designated pCB as described below.

pBC SK(−), which contains a chloramphenicol resistance selectable marker gene, was digested with Bst BI and blunt ended with T4 polymerase. A second digestion with Pvu I allowed for the removal of a 1 kilobase (kb) fragment leaving a 2.4 kb linearized vector which retained the CAT selectable resistance marker gene, an inducible LacZ promoter upstream from the LacZ gene and a ColE1 origin region. The 2.4 kb fragment was recovered. The pBS SK(−) vector was digested with Aat II and blunt ended with T4 polymerase. A second digestion with Pvu I allowed for the isolation of an 800 base pair (bp) fragment containing the f1 origin of replication. Ligation of the pBS derived 800 bp f1 fragment with the 2.4 kb pBC fragment created a pCB precursor vector containing a Sac I site, an f1 origin of replication, a CAT selectable resistance marker gene, ColE1 origin, a multiple cloning site (MCS) flanked by $T_3$ and $T_7$ promoters, and an inducible LacZ promoter upstream from LacZ gene.

The pCB precursor vector was then digested with Sac I and blunt-ended with T4 polymerase. The T4 polymerase-treated pCB vector was then religated to form pCB vector and is lacking a Sac I site.

(ii) Preparation of pCBAK0

The pCB vector containing the CAT selectable resistance marker gene was digested with Sac II and Apa I and treated with phosphatase to prevent religation and to form linearized pCB vector. The pComb vector prepared in Example 1(a)(iv) was restriction digested with Sac II and Apa I to release a fragment containing nucleotide residue sequences starting 5' to the LacZ promoter and extending past the 3' end of the second Not I site. The Sac II and Apa I pComb DNA fragment was then directionally ligated into the similarly digested pCB vector to form phagemid expression vector pCBAK0. Preferred pCBAK expression vectors are constructed with pComb2. The resultant pCBAK expression vector contained only one Spe I restriction site.

(iii) Preparation of pCBAK8

To prepare a pCBAK-based phagemid expression vector which encodes a bacteriophage coat protein membrane anchor domain in the expressed fusion protein, pCB phagemid cloning vector prepared in Example 1c(ii) was linearized by digestion with Sac II and Apa I. The pCombVIII phagemid expression vector, prepared in Example 1b(i), was restriction digested with Sac II and Apa I to form a fragment containing a nucleotide residue sequence starting 5' to the LacZ promoter and extending past the 3' end of the second Not 1 site. The fragment was directionally ligated into the linearized pCB cloning vector to form phagemid expression vector pCBAK8.

(iv) Preparation of pCBAK3

The phagemid expression vector, pCBAK3, for the expression of fusion protein having cpIII membrane anchor domains, was similarly constructed by directionally ligating the Sac II and Apa I restriction digested fragment from pCombIII with Sac II and Apa I linearized pCB cloning vector.

2. Construction of Dicistronic Expression Vectors for Expressing Anti-NPN Heterodimer on Phage Surfaces In practicing this invention, the heavy (Fd consisting of $V_H$ and $C_H1$) and light (kappa) chains ($V_L$, $C_L$) of antibodies are first targeted to the periplasm of *E. coli* for the assembly of heterodimeric Fab molecules. In order to obtain expression of antibody Fab libraries on a phage surface, the nucleotide residue sequences encoding either the Fd or light chains must be operatively linked to the nucleotide residue sequence encoding a filamentous bacteriophage coat protein membrane anchor. Two preferred coat proteins for use in this invention in providing a membrane anchor are VIII and III (cpVIII or cp8 and cpIII or cp3, respectively). In the Examples described herein, methods for operatively linking a nucleotide residue sequence encoding a Fd chain to either cpVIII or cpIII membrane anchors in a fusion protein of this invention are described.

In a phagemid vector, a first and second cistron consisting of translatable DNA sequences are operatively linked to form a dicistronic DNA molecule. Each cistron in the dicistronic DNA molecule is linked to DNA expression control sequences for the coordinate expression of a fusion protein, Fd-cpVIII or Fd-cpIII, and a kappa light chain.

The first cistron encodes a periplasmic secretion signal (pelB leader) operatively linked to the fusion protein, either Fd-cpVIII or Fd-cpIII. The second cistron encodes a second pelB leader operatively linked to a kappa light chain. The presence of the pelB leader facilitates the coordinated but separate secretion of both the fusion protein and light chain from the bacterial cytoplasm into the periplasmic space.

The process described above is schematically diagrammed in FIG. 6. Briefly, the phagemid expression vector carries a chloramphenicol acetyl transferase (CAT) selectable resistance marker gene in addition to the Fd-cpVIII fusion and the kappa chain. The f1 phage origin of replication facilitates the generation of single stranded phagemid. The isopropyl thiogalactopyranoside (IPTG) induced expression of a dicistronic message encoding the Fd-cpVIII fusion ($V_H$, $C_{H1}$, cpVIII) and the light chain ($V_L$, $C_L$) leads to the formation of heavy and light chains. Each chain is delivered to the periplasmic space by the pelB leader sequence, which is subsequently cleaved. The heavy chain is anchored in the membrane by the cpVIII membrane anchor domain while the light chain is secreted into the periplasm. The heavy chain in the presence of light chain assembles to form Fab molecules. This same result can be achieved if, in the alternative, the light chain is anchored in the membrane via a light chain fusion protein having a membrane anchor and heavy chain is secreted via a pelB leader into the periplasm.

Figure 6:
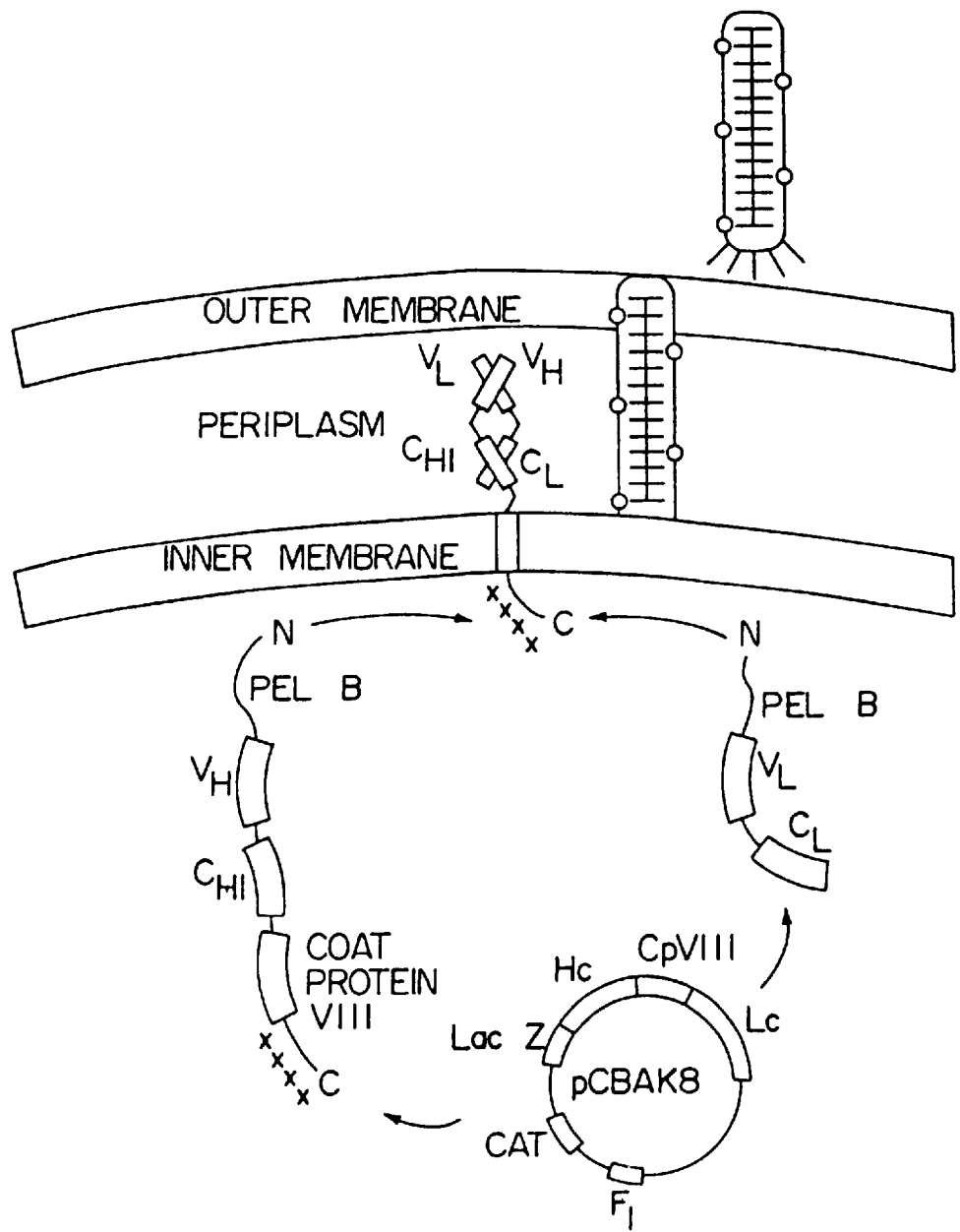
FIG. 6 illustrates a schematic diagram of the composition of pCBAK8-2b phagemid vector, the pathway for Fab assembly and incorporation in phage coat. The vector carries the chloramphenicol acetyl transferase (CAT) marker gene in addition to the nucleotide residue sequences encoding the Fd-cpVIII fusion polypeptide and the kappa chain. The f1 phage origin of replication facilitates the generation of single stranded phagemid. Expression of a dicistronic message encoding the Fd-cpVIII fusion ($V_H$, $C_{H1}$, cpVIII) and the light chain ($V_L$, $C_L$) leads to the formation of heavy and light chains. Each chain is delivered to the periplasmic space by the pelB target sequence, which is subsequently cleaved. The heavy chain is anchored in the membrane by cpVIII fusion while the light chain is secreted into the periplasm. The heavy chain in the presence of light chain assembles to form Fab molecules. The Fabs are incorporated into phage particles via cpVIII (black dots).

With subsequent infection of *E. coli* with a helper phage, as the assembly of the filamentous bacteriophage progresses, the coat protein VIII is incorporated along the entire length of the filamentous phage particles as shown in FIG. 6. A multiplicity of binding sites, consisting of approximately 2700 cpVIII monomers assembled in a tubular array, exist along the particle surface and the construct does not interfere with phage infectivity. If cpIII is used, the accumulation occurs on the tail of the bacteriophage.

a. Polynucleotide Selection

The nucleotide sequences encoding the immunoglobulin protein CDR's are highly variable. However, there are several regions of conserved sequences that flank the V region domains of either the light or heavy chain, for instance, and that contain substantially conserved nucleotide sequences, i.e., sequences that will hybridize to the same primer sequence.

Polynucleotide synthesis (amplification) primers that hybridize to the conserved sequences and incorporate restriction sites into the DNA homolog produced that are therefore suitable for operatively linking the synthesized DNA fragments to a vector were constructed. More specifically, the primers are designed so that the resulting DNA homologs produced can be inserted into an expression vector of this invention in reading frame with the upstream translatable DNA sequence at the region of the vector containing the directional ligation means. Amplification with the primers described herein is performed on cDNA templates produced from mRNA isolated from NPN-KLH-immunized mice as described in Examples 2b and 2c below.

(i) $V_H$ Primers

For amplification of the $V_H$ domains, primers are designed to introduce cohesive termini compatible with directional ligation into the unique Xho I and Spe I sites of the phagemid Hc2 expression vector. In all cases, the 5' primers listed in SEQ ID NOs:40–49 are chosen to be complementary to the first strand cDNA in the conserved N-terminus region (antisense strand). Initially amplification is performed with a mixture of 32 primers (SEQ ID NO:40) that were degenerate at five positions. Hybridoma mRNA could be amplified with mixed primers, but initial attempts to amplify mRNA from spleen yield variable results. Therefore, several alternatives to amplification using the mixed 5' primers are compared.

The first alternative is to construct multiple unique primers, eight of which are shown in Table 5, corresponding to individual members of the mixed primer pool. The individual primers listed in SEQ ID Nos:41–48 are constructed by incorporating either of the two possible nucleotides at three of the five degenerate positions.

The second alternative is to construct a primer containing inosine (SEQ ID NO:49) at four of the variable positions based on the published work of Takahashi, et al., *Proc. Natl. Acad. Sci., USA*, 82:1931–1935, (1985) and Ohtsuka et al., *J. Biol. Chem.*, 260: 2605–2608, (1985). This primer has the advantage that it is not degenerate and, at the same time minimizes the negative effects of mismatches at the unconserved positions as discussed by Martin et al., *Nuc. Acids Res.*, 13:8927 (1985). However, it is not known if the presence of inosine nucleotides would result in incorporation of unwanted sequences in the cloned $V_H$ regions. Therefore, inosine is not included at the one position that remains in the amplified fragments after the cleavage of the restriction sites. As a result, inosine is not in the cloned insert.

Additional $V_H$ amplification primers including the unique 3' primer are designed to be complementary to a portion of the first constant region domain of the gamma 1 heavy chain mRNA (SEQ ID NOs:54 and 55). These primers will produce DNA homologs containing polynucleotides coding for amino acids from the $V_H$ and the first constant region domains of the heavy chain. These DNA homologs can therefore be used to produce Fab fragments rather than $F_v$.

Additional unique 3' primers designed to hybridize to similar regions of another class of immunoglobulin heavy chain such as IgM, IgE and IgA are contemplated. Other 3' primers that hybridize to a specific region of a specific class of $CH_1$ constant region and are adapted for transferring the $V_H$ domains amplified using this primer to an expression vector capable of expressing those $V_H$ domains with a different class of heavy or light chain constant region are also contemplated.

As a control for amplification from spleen or hybridoma mRNA, a set of primers hybridizing to a highly conserved region within the constant region IgG, heavy chain gene are constructed. The 5' primer (SEQ ID NO:50) is complementary to the cDNA in the $C_H2$ region whereas the 3' primer (SEQ ID NO:52) is complementary to the mRNA in the $C_H3$ region. It is believed that no mismatches are present between these primers and their templates.

Amplification is performed in eight separate reactions, each containing one of the 5' primers shown in SEQ ID NOs:41–48 and a 3' primer shown in SEQ ID NO:54. The remaining 5' primers used for amplification in a single reaction are either a degenerate primer (SEQ ID NO:40) or a primer that incorporates inosine at four degenerate positions as shown in SEQ ID NOs: 49, 69 and 70. The remaining 3' primer (SEQ ID NO:68) is used to construct $F_v$ fragments. Many of the 5' primers incorporate a Xho I site, and the 3' primers incorporate a Spe I restriction site for insertion of the $V_H$ DNA homolog into the phagemid Hc2 expression vector (FIG. 2).

$V_H$ amplification primers designed to amplify human heavy chain variable regions are contemplated. One of the 5' heavy chain primer contains inosine residues at degenerate nucleotide positions allowing a single primer to hybridize to a large number of variable region sequences. Primers designed to hybridize to the constant region sequences of various IgG mRNAs are also contemplated.

(ii) $V_L$ Primers

The nucleotide sequences encoding the $V_L$ CDRs are highly variable. However, there are several regions of conserved sequences that flank the $V_L$ CDR domains including the $J_L$, $V_L$ framework regions and $V_L$ leader/promotor. Therefore, amplification primers are constructed that hybridized to the conserved sequences and incorporate restriction sites that allow cloning the amplified fragments into the phagemid Lc2 vector cut with Sac I and Xba I.

Figure 4:
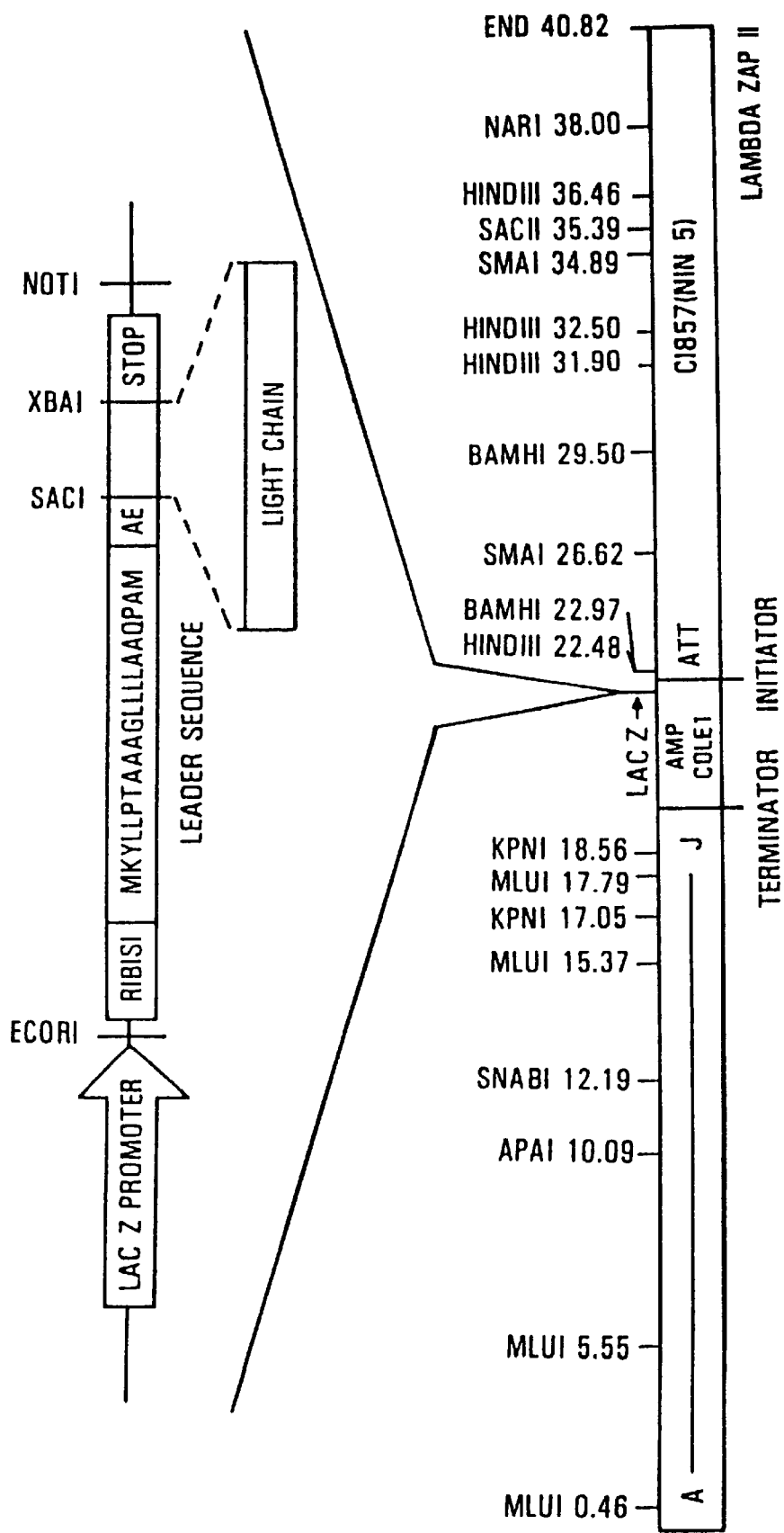
FIG. 4 illustrates the major features of the bacterial expression vector Lc2 ($V_L$ expression vector). The synthetic DNA sequence from FIG. 3 is shown at the top along with the LacZ promoter from Lambda Zap II. The orientation of the insert in Lambda Zap II is shown. The $V_L$ DNA homologs are inserted into the Sac I and Xho I cloning sites.

For amplification of the $V_L$ CDR domains, the 5' primers (SEQ ID NOs:56–63) are designed to be complementary to the first strand cDNA in the conserved N-terminus region. These primers also introduce a Sac I restriction endonuclease site to allow the $V_L$ DNA homolog to be cloned into the phagemid Lc2 expression vector. The 3' $V_L$ amplification primer (SEQ ID NO:64) is designed to be complementary to the mRNA in the $J_L$ regions and to introduce the Xba I restriction endonuclease site required to insert the $V_L$ DNA homolog into the phagemid Lc2 expression vector (FIG. 4).

Additional 3' $V_L$ amplification primers are designed to hybridize to the constant region of either kappa or lambda mRNA (SEQ ID NOs:65 and 66). These primers allow a DNA homolog to be produced containing polynucleotide sequences coding for constant region amino acids of either kappa or lambda chain. These primers make it possible to produce a Fab fragment rather than an $F_v$.

The primers used for amplification of kappa light chain sequences for construction of Fabs are listed in the Sequence Listing. Amplification with these primers is performed in 5 separate reactions, each containing one of the 5' primers (SEQ ID NOs:58–61) and one of the 3' primers (SEQ ID NO:67). The remaining 3' primer (SEQ ID NO:64) has been used to construct $F_v$ fragments. The 5' primers contain a Sac I restriction site and the 3' primers contain a Xba I restriction site.

$V_L$ amplification primers designed to amplify human light chain variable regions of both the lambda and kappa isotypes are also contemplated.

All primers and synthetic polynucleotides described herein, were either purchased from Research Genetics in Huntsville, Ala. or synthesized on an Applied Biosystems DNA synthesizer, model 381A, using the manufacturer's instruction.

b. Preparation of a Repertoire of Genes

Encoding Immunoglobulin Variable Domain Nitrophenylphosphonamidate (NPN) is selected as one of the ligands for receptor binding in preparing a heterodimeric receptor according to the methods of the invention. Others used in practicing this invention are described in Example 6.

Keyhole limpet hemocyanin (KLH) is conjugated to NPN to form a NPN-KLH conjugate used for immunizing a mouse to produce an anti-NPN immune response and thereby provide a source of ligand specific heterodimeric receptor genes.

The NPN-KLH conjugate is prepared by admixing 250 ul of a solution containing 2.5 mg of NPN in dimethylformamide with 750 ul of a solution containing 2 mg of KLH in 0.01 Molar (M) sodium phosphate buffer (pH 7.2). The two solutions are admixed by slow addition of the NPN solution to the KLH solution while the KLH solution is being agitated by a rotating stirring bar. Thereafter the admixture is maintained at 4 C. for 1 hour with the same agitation to allow conjugation to proceed. The conjugated NPN-KLH is isolated from the nonconjugated NPN and KLH by gel filtration through Sephadex G-25. The isolated NPN-KLH conjugate is injected into mice as described below.

The NPN-KLH conjugate is prepared for injection into mice by adding 100 ug of the conjugate to 250 ul of phosphate buffered saline (PBS). An equal volume of complete Freund's adjuvant is added and emulsified the entire solution for 5 minutes. A 129 $G_{IX+}$ mouse is injected with 300 ul of the emulsion. Injections are given subcutaneously at several sites using a 21 gauge needle. A second immunization with NPN-KLH is given two weeks later. This injection is prepared as follows: 50 micrograms (ug) of NPN-KLH were diluted in 250 ul of PBS and an equal volume of alum is admixed to the NPN-KLH solution. Five hundred ul of the solution is then injected into the mouse intraperitoneally using a 23 gauge needle. One month later the mice are given a final injection of 50 ug of the NPN-KLH conjugate diluted to 200 ul in PBS. This injection is given intravenously in the lateral tail vein using a 30 gauge needle. Five days after this final injection the mice are sacrificed and total cellular RNA is isolated from their spleens.

Total cellular RNA is prepared from the spleen of a single mouse immunized with KLH-NPN as described above using the RNA preparation methods described by Chomczynski et al., *Anal Biochem.*, 162:156–159 (1987) and using the RNA isolation kit (Stratagene) according to the manufacturer's instructions. Briefly, immediately after removing the spleen from the immunized mouse, the tissue is homogenized in 10 ml of a denaturing solution containing 4.0M guanine isothiocyanate, 0.25M sodium citrate at pH 7.0, and 0.1M beta-mercaptoethanol using a glass homogenizer. One ml of sodium acetate at a concentration of 2M at pH 4.0 is admixed with the homogenized spleen. One ml of phenol that is previously saturated with $H_2O$ is also admixed to the denaturing solution containing the homogenized spleen. Two ml of a chloroform:isoamyl alcohol (24:1 v/v) mixture are added to this homogenate. The homogenate is mixed vigorously for ten seconds and maintained on ice for 15 minutes. The homogenate is then transferred to a thick-walled 50 ml polypropylene centrifuged tube (Fisher Scientific Company, Pittsburg, Pa.). The solution is centrifuged at 10,000×g for 20 minutes at 4 C. The upper RNA-containing aqueous layer is transferred to a fresh 50 ml polypropylene centrifuge tube and mixed with an equal volume of isopropyl alcohol. This solution is maintained at −20 C. for at least one hour to precipitate the RNA. The solution containing the precipitated RNA is centrifuged at 10,000×g for 20 minutes at 4 C. The pelleted total cellular RNA is collected and dissolved in 3 ml of the denaturing solution described above. Three ml of isopropyl alcohol is added to the re-suspended total cellular RNA and vigorously mixed. This solution is maintained at −20 C. for at least 1 hour to precipitate the RNA. The solution containing the precipitated RNA is centrifuged at 10,000×g for 10 minutes at 4 C. The pelleted RNA was washed once with a solution containing 75% ethanol. The pelleted RNA is dried under vacuum for 15 minutes and then re-suspended in dimethyl pyrocarbonate (DEPC) treated (DEPC-$H_2O$) $H_2O$.

Messenger RNA (mRNA) enriched for sequences containing long poly A tracts is prepared from the total cellular RNA using methods described in *Molecular Cloning: A Laboratory Manual*, Maniatis et al., eds., Cold Spring Harbor, N.Y., (1982). Briefly, one half of the total RNA isolated from a single immunized mouse spleen prepared as described above is resuspended in 1 ml of DEPC-$H_2O$ and maintained at 65 C. for 5 minutes. One ml of 2×high salt loading buffer consisting of 100 mM Tris-HCl, 1M NaCl, 2.0 mM EDTA at pH 7.5, and 0.2% sodium dodecyl sulfate (SDS) is added to the re-suspended RNA and the mixture allowed to cool to room temperature. The mixture is then applied to an oligo-dT (Collaborative Research Type 2 or Type 3) column that was previously prepared by washing the oligo-dT with a solution containing 0.1M sodium hydroxide and 5 mM EDTA and then equilibrating the column with DEPC-$H_2O$. The eluate is collected in a sterile polypropylene tube and reapplied to the same column after heating the eluate for 5 minutes at 65 C.

The oligo-dT column is then washed with 2 ml of high salt loading buffer consisting of 50 mM Tris-HCl at pH 7.5, 500 mM NaCl, 1 mM EDTA and 0.1% SDS. The oligo dT column is then washed with 2 ml of 1×medium salt buffer consisting of 50 mM Tris-HCl at pH 7.5, 100 mM, 1 mM EDTA and 0.1% SDS. The messenger RNA is eluted from the oligo-dT column with 1 ml of buffer consisting of 10 mM Tris-HCl at pH 7.5, 1 mM EDTA and 0.05% SDS. The messenger RNA is purified by extracting this solution with phenol/chloroform followed by a single extraction with 100% chloroform. The messenger RNA is concentrated by ethanol precipitation and resuspended in DEPC $H_2O$.

The messenger RNA (mRNA) isolated by the above process contains a plurality of different $V_H$ coding polynucleotides, i.e., greater than about $10^4$ different $V_H$-coding genes, and contains a similar number of $V_L$-coding genes. Thus, the mRNA population represents a repertoire of variable region-coding genes. Also contemplated for use in this invention are repertoires of variable region-coding genes resulting from immunization with diverse antigens such as tetanus toxoid, gammaglobulin, various hapten-antigen conjugates and the like. Preferred antigen-specific libraries for use are described in Example 6.

c. Preparation of DNA Homologs

In preparation for PCR amplification, mRNA prepared above is used as a template for cDNA synthesis by a primer extension reaction. In a typical 50 ul transcription reaction, 5–10 ug of spleen mRNA in water is first hybridized (annealed) with 500 ng (50.0 pmol) of the 3' $V_H$ primer listed in SEQ ID NO:51, at 65 C. for five minutes. Subsequently, the mixture is adjusted to 1.5 mM DATP, dCTP, dGTP and dTTP, 40 mM Tris-HCl at pH 8.0, 8 mM $MgCl_2$ 50 mM NaCl, and 2 mM spermidine. Moloney-Murine Leukemia virus reverse transcriptase (Stratagene), 26 units, is added and the solution is maintained for 1 hour at 37 C.

PCR amplification is performed in a 100 ul reaction containing the products of the reverse transcription reaction (approximately 5 ug of the cDNA/RNA hybrid), 300 ng of 3' $V_H$ primer (SEQ ID NO:51), 300 ng each of the 5' $V_H$ primers (SEQ ID NOs:41–49) 200 mM of a mixture of dNTP's, 50 mM KCl, 10 mM Tris-HCl at pH 8.3, 15 mM $MgCl_2$, 0.1% gelatin and 2 units of *Thermus aquaticus* (Taq) DNA polymerase (Perkin-Elmer-Cetus, Emeryville, Calif.). The reaction mixture is overlaid with mineral oil and subjected to 40 cycles of amplification. Each amplification cycle includes denaturation at 92 C. for 1 minute, annealing at 52 C. for 2 minutes and polynucleotide synthesis by primer extension (elongation) at 72 C. for 1.5 minutes. The amplified $V_H$-coding DNA homolog containing samples are then extracted twice with phenol/chloroform, once with chloroform, ethanol precipitated and are stored at −70 C. in 10 mM Tris-HCl at pH 7.5 containing 1 mM EDTA.

Using unique 5' primers (SEQ ID NOs:41 to 48), efficient $V_H$-coding DNA homolog synthesis and amplification from the spleen mRNA is achieved as shown by agarose gel electrophoresis. The amplified cDNA ($V_H$-coding DNA homolog) is seen as a major band of the expected size (360 bp). The amount the amplified $V_H$-coding polynucleotide fragment in each reaction is similar, indicating that all of these primers were about equally efficient in initiating amplification. The yield and quality of the amplification with these primers is reproducible.

The primer containing inosine also synthesizes amplified $V_H$-coding DNA homologs from spleen mRNA reproducibly, leading to the production of the expected sized fragment, of an intensity similar to that of the other amplified cDNAs. The presence of inosine also permits efficient DNA homolog synthesis and amplification, clearly indicating that such primers are useful in generating a plurality of $V_H$-coding DNA homologs. Amplification products obtained from the constant region primers (SEQ ID NOs: 50 and 52) are more intense indicating that amplification was more efficient, possibly because of a higher degree of homology between the template and primers. Following the above procedures, a $V_H$-coding gene library is constructed from the products of eight amplifications, each performed with a primer. different 5' primer. Equal portions of the products from each primer extension reaction are mixed and the mixed product is then used to generate a library of $V_H$-coding DNA homolog-containing vectors.

DNA homologs of the $V_L$ are also prepared from the purified mRNA prepared as described above. In preparation for PCR amplification, mRNA prepared according to the above examples is used as a template for cDNA synthesis. In a typical 50 ul transcription reaction, 5–10 ug of spleen mRNA in water is first annealed with 300 ng (50.0 pmol) of the 3' $V_L$ primer (SEQ ID NO:53), at 65 C. for five minutes. Subsequently, the mixture is adjusted to 1.5 mM DATP, dCTP, dGTP, and dTTP, 40 mM Tris-HCl at pH 8.0, 8 mM $MgCl_2$, 50 mM NaCl, and 2 mM spermidine. Moloney-Murine Leukemia virus reverse transcriptase (Stratagene), 26 units, is added and the solution is maintained for 1 hour at 37 C. The PCR amplification is performed in a 100 ul reaction containing approximately 5 ug of the cDNA/RNA hybrid produced as described above, 300 ng of the 3' $V_L$ primer (SEQ ID NO: 53), 300 ng of the 5' $V_L$ primer (SEQ ID NO:54), 200 mM of a mixture of dNTP's, 50 mM KCl, 10 mM Tris-HCl at pH 8.3, 15 mM $MgCl_2$, 0.1% gelatin and 2 units of Taq DNA polymerase. The reaction mixture is overlaid with mineral oil and subjected to 40 cycles of amplification. Each amplification cycle includes denaturation at 92 C. for 1 minute, annealing at 52 C. for 2 minutes and elongation at 72 C. for 1.5 minutes. The amplified samples are then extracted twice with phenol/chloroform, once with chloroform, ethanol precipitated and are stored at −70 C. in 10 mM Tris-HCl at pH 7.5 and 1 mM EDTA.

d. Insertion of DNA Homologs into a DNA Expression Vector

To prepare an expression library enriched in $V_H$ sequences, DNA homologs enriched in $V_H$ sequences are prepared according to Example 2c using the same set of 5' primers but with primer in SEQ ID NO:53 as the 3' primer.

The resulting PCR amplified products (2.5 ug/30 ul of 150 mM NaCl, 8 mM Tris-HCl at pH 7.5, 6 mM $MgSO_4$, 1 mM DTT, 200 ug/ml BSA) are digested at 37 C. with restriction enzymes Xho I (125 units) and Spe I (125 units). In cloning experiments which required a mixture of the products of the amplification reactions, equal volumes (50 ul, 1–10 ug concentration) of each reaction mixture are combined after amplification but before restriction digestion. The $V_H$ homologs are purified on a 1% agarose gel using the standard electroelution technique described in *Molecular Cloning A Laboratory Manual*, Maniatis et al., eds., Cold Spring Harbor, N.Y., (1982). After gel electrophoresis of the digested PCR amplified spleen mRNA, the region of the gel containing DNA fragments of approximate 350 bp is excised, electroeluted into a dialysis membrane, ethanol precipitated and resuspended in a TE solution containing 10 mM Tris-HCl at pH 7.5 and 1 mM EDTA to a final concentration of 50 ng/ul. The resulting $V_H$ DNA homologs represent a repertoire of polypeptide genes having cohesive termini adapted for directional ligation to the vector Lambda Hc2 . These prepared $V_H$ DNA homologs are then directionally ligated into linearized Lambda Hc2 expression vector prepared as described below.

The Lambda Hc2 expression DNA vector is prepared for inserting a DNA homolog by admixing 100 ug of this DNA to a solution containing 250 units each of the restriction endonucleases Xho I and Spe I (both from Boehringer Mannheim, Indianapolis, Ind.) and a buffer recommended by the manufacturer. This solution is maintained at 37 C. from 1.5 hours. The solution is heated at 65 C. for 15 minutes to inactivate the restriction endonucleases. The solution is chilled to 30 C. and 25 units of heat-killable (HK) phosphatase (Epicenter, Madison, Wis.) and $CaCl_2$ is admixed to it according to the manufacturer's specifications. This solution is maintained at 30 C. for 1 hour. The DNA is purified by extracting the solution with a mixture of phenol and chloroform followed by ethanol precipitation.

The Lambda Hc2 expression vector is now ready for ligation to the $V_H$ DNA homologs prepared in the above examples. These prepared $V_H$ DNA homologs are then directly inserted into the Xho I and Spe I restriction digested Lambda Hc2 expression vector that prepared above by ligating 3 moles of $V_H$ DNA homolog inserts with each mole of the Hc2 expression vector overnight at 5 C. Approximately $3.0 \times 10^5$ plague forming units are obtained after packaging the DNA with Gigapack II Bold (Stratagene) of which 50% are recombinants. The ligation mixture containing the $V_H$ DNA homologs are packaged according to the manufacturer's specifications using Gigapack Gold II Packing Extract (Stratagene). The resulting Lambda Hc2 expression libraries are then transformed into XL1-Blue cells.

To prepare a library enriched in $V_L$ sequences, PCR amplified products enriched in $V_L$ sequences are prepared according to Example 2c. These $V_L$DNA homologs are digested with restriction enzymes Sac I and Xba I and the digested $V_L$ DNA homologs are purified on a 1% agarose gel as described above for the $V_H$ DNA homologs to form a repertoire of $V_L$-polypeptide genes adapted for directional ligation. The prepared $V_L$ DNA homologs are then directionally ligated into the Lambda Lc2 expression vector previously digested with the restriction enzymes, Sac I and Xba I as described for Lambda Hc2 . The ligation mixture containing the $V_L$ DNA homologs is packaged to form a Lambda Lc2 expression library as described above and is ready to be plated on XL1-Blue cells.

e. Randomly Combining $V_H$ and $V_L$ DNA Homologs on the Same Expression Vector The construction of a library containing vectors for expressing two cistrons that express heavy and light chains is accomplished in two steps. In the first step, separate heavy and light chain libraries are constructed in the expression vectors Lambda Hc2 and Lambda Lc2, respectively, as described using gene repertoires obtained from a mouse immunized with NPN-KLH as described above. In the second step, these two libraries are combined at the antisymmetric EcoR I sites present in each vector. This resulted in a library of clones each of which potentially co-expresses a heavy and a light chain. The actual combinations are random and do not necessarily reflect the combinations present in the B-cell population in the parent animal.

The spleen mRNA resulting from the above immunizations (Example 2b) is isolated and used to create a primary library of $V_H$ gene sequences using the Lambda Hc2 expression vector. The primary library contains $1.3 \times 10^6$ plaque-forming units (pfu) and can be screened for the expression of the decapeptide tag to determine the percentage of clones expressing $V_H$ and $C_H1$ (Fd) sequences. The sequence for this peptide is only in frame for expression following the cloning of a Fd (or $V_H$) fragment into the vector. At least 80% of the clones in the library express Fd fragments based on immunodetection of the decapeptide tag.

The light chain library is constructed in the same way as the heavy chain and contains $2.5 \times 10^6$ members. Plaque screening, using an anti-kappa chain antibody, indicates that 60% of the library contained express light chain inserts. A small percentage of inserts results from incomplete dephosphorylation of vector after cleavage with Sac I and Xba I.

Once obtained, the two libraries are used to construct a combinatorial library by crossing them at the EcoR I site. To accomplish the cross, DNA is first purified from each library.

The Lambda Lc2 library prepared in Example 2d is amplified and 500 ug of Lambda Lc2 expression library phage DNA is prepared from the amplified phage stock using the procedures described in *Molecular Cloning: A Laboratory Manual*, Maniatis et al., eds., Cold Spring Harbor, N.Y. (1982). Fifty ug of this amplified expression library phage DNA is maintained in a solution containing 100 units of MLu I restriction endonuclease (Boehringer Mannheim, Indianapolis, Ind.) in 200 ul of a buffer supplied by the endonuclease manufacturer for 1.5 hours at 37 C. The solution is then extracted with a mixture of phenol and chloroform. The DNA is then ethanol precipitated and resuspended in 100 ul of water. This solution is admixed with 100 units of the restriction endonuclease EcoR I (Boehringer) in a final volume of 200 ul of buffer containing the components specified by the manufacturer. This solution is maintained at 37 C. for 1.5 hours and the solution is then extracted with a mixture of phenol and chloroform. The DNA is ethanol precipitated then resuspended in TE.

The Lambda Hc2 expression library prepared in Example 2d is amplified and 500 ug of Lambda Hc2 expression library phage DNA is prepared using the methods detailed above. Fifty ug of this amplified library phage DNA is maintained in a solution containing 100 units of Hind III restriction endonuclease (Boehringer) in 200 ul of a buffer supplied by the endonuclease manufacturer for 1.5 hours at 37 C. The solution is then extracted with a mixture of phenol and chloroform saturated with 0.1M Tris-HCl at pH 7.5. The DNA is then ethanol precipitated and re-suspended in 100 ul of water. This solution is admixed with 100 units of the restriction endonuclease EcoR I (Boehringer) in a final volume of 200 ul of buffer containing the components specified by the manufacturer. This solution is maintained at 37 C. for 1.5 hours and the solution is then extracted with a mixture of phenol and chloroform. The DNA is ethanol precipitated and resuspended in TE.

The restriction digested Hc2 and Lc2 expression libraries are ligated together. To that end, a DNA admixture consisting of 1 ug of Hc2 and 1 ug of Lc2 phage library DNA is prepared in a 10 ul reaction using the reagents supplied in a ligation kit (Stratagene). The DNA admixture is warmed to 45 C. for 5 minutes to melt any cohesive termini that may reanneal. The admixture is then chilled to 0° C. to prevent religation. Bacteriophage T4 DNA ligase (0.1 Weiss units which is equivalent to 0.02 units as determined in an exonuclease resistance assay) is admixed into the chilled DNA solution along with 1 ul of 5 mM ATP and 1 ul 10×bacteriophage T4 DNA ligase buffer (10×buffer is prepared by admixing 200 mM Tris-HCl at pH 7.6, 50 mM $MgCl_2$, 50 mM DTT, and 500 ug/ml BSA) to form a ligation admixture. After ligation for 16 hours at 4 C., 1 ul of the ligated the phage DNA is packaged with Gigapack Gold II packaging extract and plated on XL1-Blue cells prepared according to the manufacturer's instructions to form a Lambda phage library of dicistronic expression vectors capable of expressing heavy and light chains derived from the NPN-immunized mouse. A portion of the clones obtained are used to determine the effectiveness of the combination.

f. Selection of Anti-NPN Reactive Heterodimer-Producing Dicistronic Vectors

The combinatorial Fab expression library prepared above in Example 2a is screened to identify clones having affinity for NPN. To determine the frequency of the phage clones which co-expressed the light and heavy chain fragments, duplicate lifts of the light chain, heavy chain and combinatorial libraries are screened as above for light and heavy chain expression. In this study of approximately 500 recombinant phage, approximately 60% co-expressed light and heavy chain proteins.

All three libraries, the light chain, the heavy chain and the combinatorial, are screened to determine if they contained recombinant phage that expressed antibody fragments which bound NPN. In a typical procedure 30,000 phage are plated on XL1-Blue cells and duplicate lifts with nitrocellulose are screened for binding to NPN coupled to $^{125}I$ labeled BSA. The BSA is iodinated following the Chloramine-T method as described by Bolton et al., *Biochem.*, 133:529–534 (1973).

To assess the ability to screen large numbers of clones and obtain a more quantitative estimate of the frequency of antigen binding clones in the combinatorial library, one million phage plaques are screened and approximately 100 clones which bound to antigen are identified. For six clones which are believed to bind NPN, a region of the plate containing the six positive and approximately 20 surrounding bacteriophage plaques is selected and each plaque is cored, replated, and screened with duplicate lifts.

Clone 2b, one of the plaques which reacts with NPN, is excised according to an in vivo excision protocol where 200 ul of phage stock and 200 ul of a F+ derivative of XL1-Blue ($A_{600}=1.00$) (Stratagene) are admixed with 1 ul of M13 mp8 helper phage ($1 \times 10^{10}$ pfu/ml and maintained at 37 C. for 15 minutes. After a 4 hour maintenance in Luria-Bertani (LB) medium and heating at 70 C. for 20 minutes to heat kill the XL1-Blue cells, the phagemids are re-infected into XL1-Blue cells and plated onto LB plates containing ampicillin. This procedure converts the cloned insert from the Lambda Zap II vector into a plasmid vector to allow easy manipulation and sequencing (Stratagene). The phagemid DNA encoding the $V_H$ and part of the $V_L$ is then determined by DNA sequencing using the Sanger dideoxy method described in Sanger et al., *Proc. Natl. Acad. Sci.*, 74:5463–5467 (1977) using a Sequenase kit according to manufacturer's instructions (US Biochemical Corp., Cleveland, Ohio). The nucleotide residue sequence of Clone 2b Fd chain is listed in the Sequence Listing as SEQ ID NO 71. The nucleotide residue sequences of the kappa light chain variable and constant regions are listed in the Sequence Listing as SEQ ID NO:72 and SEQ ID NO:73, respectively.

g. Preparation of a DNA Sequence Encoding a Filamentous Phage Coat Protein Membrane Anchor cpVIII Membrane Anchor: M13 mp18, a commercially available bacteriophage vector (Pharmacia, Piscataway, N.J.), was used as a source for isolating the gene encoding cpVIII. The sequence of the gene encoding the membrane anchor domain of cpVIII listed in Sequence Listing as SEQ ID NO:74, was modified through PCR amplification to incorporate the restriction endonuclease sites, Spe I and EcoR I, and two stop codons prior to the EcoR I site. The corresponding amino acid residue sequence of the membrane anchor domain of cpVIII is listed as SEQ ID NO:17.

To prepare a modified cpVIII, replicative form DNA from M13 mp18 was first isolated. Briefly, into 2 ml of LB (Luria-Bertani medium), 50 ul of a culture of a bacterial strain carrying an F' episome (JM107, JM109 or TG1) was admixed with a one tenth suspension of bacteriophage particles derived from a single plaque. The admixture was incubated for 4 to 5 hours at 37 C. with constant agitation. The admixture was then centrifuged at 12,000×g for 5 minutes to pellet the infected bacteria. After the supernatant was removed, the pellet was resuspended by vigorous vortexing in 100 ul of ice-cold solution I. Solution I was prepared by admixing 50 mM glucose, 10 mM EDTA and 25 mM Tris-HCl at pH 8.0, and autoclaving for 15 minutes.

To the bacterial suspension, 200 ul of freshly prepared Solution II was admixed and the tube was rapidly inverted five times. Solution II was prepared by admixing 0.2N NaOH and 1% SDS. To the bacterial suspension, 150 ul of ice-cold Solution III was admixed and the tube was vortexed gently in an inverted position for 10 seconds to disperse Solution III through the viscous bacterial lysate. Solution III was prepared by admixing 60 ml of 5M potassium acetate, 11.5 ml of glacial acetic acid and 28.5 ml of water. The resultant bacterial lysate was then stored on ice for 5 minutes followed by centrifugation at 12,000×g for 5 minutes at 4 C. in a microfuge. The resultant supernatant was recovered and transferred to a new tube. To the supernatant was added an equal volume of phenol/chloroform and the admixture was vortexed. The admixture was then centrifuged at 12,000×g for 2 minutes in a microfuge. The resultant supernatant was transferred to a new tube and the double-stranded bacteriophage DNA was precipitated with 2 volumes of ethanol at room temperature. After allowing the admixture to stand at room temperature for 2 minutes, the admixture was centrifuged to pellet the DNA. The supernatant was removed and the pelleted replicative form DNA was resuspended in 25 ul of Tris-HCl at pH 7.6, and 10 mM EDTA (TE).

The double-stranded M13 mp18 replicative form DNA was then used as a template for PCR. Primers, AK 5 (SEQ ID NO:75) and AK 6 (SEQ ID NO:76), the sequences of which are listed in Table 5 below, were used in the PCR reaction to amplify the mature gene for cpVIII member anchor domain and incorporate the two cloning sites, Spe I and EcoR I. For the PCR reaction, 2 ul containing 1 ng of M13mp18 replicative form DNA was admixed with 10 ul of 10×PCR buffer purchased commercially (Promega Biotech, Madison, Wis.) in a 0.5 ml microfuge tube. To the DNA admixture, 8 ul of a 2.5 mM solution of dNTPs (DATP, dCTP, dGTP, dTTP) was admixed to result in a final concentration of 200 uM. Three ul (equivalent to 60 picomoles (pM)) of the 5' forward AK 5 primer and 3 ul (60 pM) of the 3' backward AK 6 primer was admixed into the DNA solution. To the admixture, 73 ul of sterile water and 1 ul/5 units of polymerase (Promega Biotech) was added. Two drops of mineral oil were placed on top of the admixture and 40 rounds of PCR amplification in a thermocycler were performed. The amplification cycle consisted of 52 C. for 2 minutes, 72 C. for 1.5 minutes and 91 C. for 2 minutes. The resultant PCR modified cpVIII membrane anchor domain DNA fragment from M13 mp18 containing samples were then purified with Gene Clean (BIO101, La Jolla, Calif.), extracted twice with phenol/chloroform, once with chloroform followed by ethanol precipitation and were stored at −70 C. in 10 mM Tris-HCl at pH 7.5, and 1 mM EDTA.

TABLE 5

| SEQ ID NO: | Primer | |
|---|---|---|
| (75)[1] | AK 5 (F) | 5' GTGCCCAGGGATTGTACTAGTGCTGAGGGTGACGAT 3' |
| (76)[2] | AK 6 (B) | 5' ACTCGAATTCTATCAGCTTGCTTTCGAGGTGAA 3' |
| (77)[3] | Hc3 (F) | 5' AGGTCCAGCTTCTCGAGTCTGG 3' |
| (78)[4] | AK 7 (B) | 5' GTCACCCTCAGCACTAGTACAATCCCTGGGCAC 3' |
| (79)[5] | G-3 (F) | 5' GAGACGACTAGTGGTGGCGGTGGCTCTCCATTCGTTTGTGAATATCAA 3' |
| (80)[6] | G-3 (B) | 5' TTACTAGCTAGCATAATAACGGAATACCCAAAAGAACTGG 3' |
| (81)[7] | LAC-F | 5' TATGCTAGCTAGTAACACGACAGGTTTCCCGACTGG 3' |
| (82)[8] | LAC-B | 5' ACCGAGCTCGAATTCGTAATCATGGTC 3' |
| (83)[9] | LAC-B' | 5' AGCTGTTGAATTCGTGAAATTGTTATCCGCT 3' |

F Forward Primer
B Backward Primer
[1]From 5' to 3': the overlapping sequence for $C_H1$ 3' end is double underlined; the Spe I restriction site sequence is single underlined; the overlapping sequence for cpVIII is double underlined.
[2]EcoR I restriction site sequence is single underlined.
[3]Xho I restriction site sequence is underlined.
[4]From 5' to 3': the overlapping sequence for cpVIII is double underlined; the Spe I restriction site sequence is single underlined; the overlapping sequence for $C_H1$ 3' end is double underlined.
[5]From 5' to 3': Spe I restriction site sequence is single underlined; the overlapping sequence with the 5' end of cpIII is double underlined
[6]From 5' to 3': Nhe I restriction site sequence is single underlined; the overlapping sequence with 3' end of cpIII is double underlined.

TABLE 5-continued

SEQ
ID NO: Primer

[7]From 5' to 3': overlapping sequence with the 3' end of cpIII is double underlined; Nhe I restriction sequence begins with the nucleotide residue "G" at position 4 and extends 5 more residues = GCTAGC.
[8]EcoR I restriction site sequence is single underlined.
[9]Alternative backwards primer for amplifying LacZ; EcoR I restriction site sequence is single underlined.

To verify amplification of the modified cpVIII membrane anchor domain, the PCR purified DNA products were electrophoresed in a 1% agarose gel. The expected size of the cpVIII was approximately 150 base pairs. The area in the agarose containing the modified cpVIII DNA fragment was isolated from the agarose as described above. The sequence of the isolated modified cpVIII DNA fragment is listed as SEQ ID NO:84. The isolated cpVIII DNA fragment was then admixed with a similarly prepared fragment of modified Fd as described below in Example 2i in order to form a DNA segment encoding the fusion protein Fd-cpVIII.

cpIII Membrane Anchor: M13 mp18 was also used as a source for isolating the gene encoding the membrane anchor domain at cpIII, the sequence of which is listed in the Sequence Listing as SEQ ID NO:85. The amino acid residue sequence of membrane anchor domain cpIII is listed in SEQ ID NO:16. M13 mp18 replicative form DNA was prepared as described above and used as a template for two PCR amplifications for construction of a DNA fragment consisting of the mature gene for cpIII membrane anchor domain located 5' to a sequence encoding the LacZ promoter, operator and cap-binding site for controlling light chain expression. The restriction sites, Spe I and EcoR I, were created in the amplification reactions and were located at the 5' and 3' ends of the fragment respectively. The procedure for creating this fragment by combining the products of two separate PCR amplifications is described below.

The primer pair, G-3(F) (SEQ ID NO:79) and G-3(B) (SEQ ID NO:80) listed in Table 5, was used in the first PCR reaction as performed above to amplify the cpIII membrane anchor gene and incorporate Spe I and Nhe I restriction sites into the fragment. The amplified PCR fragment also contained nucleotide sequences for encoding a five amino acid tether composed of four glycerine residues and one serine juxtaposed between the heavy chain and cpIII encoding domains. Once expressed, the five amino acid sequence lacking an orderly secondary structure served to minimize the interaction between the Fab and cpIII domains. The resultant PCR modified cpIII DNA fragment having Spe I and Nhe I sites in the 5' and 3' ends, respectively, of the fragment was verified and purified as described above. The sequence of the PCR modified cpIII membrane anchor domain DNA fragment is listed in the Sequence Listing as SEQ ID NO:86. A second PCR amplification using the primer pairs, Lac-F (SEQ ID NO:81) and Lac-B (SEQ ID NO:82) listed in Table 7, was performed on a separate aliquot of M13 mp18 replicative form template DNA to amplify the LacZ promoter, operator and Cap-binding site having a 5' Nhe I site and a 3' EcoR I site. The primers used for this amplification were designed to incorporate a Nhe I site on the 5' end of the amplified fragment to overlap with a portion of the 3' end of the cpIII gene fragment and of the Nhe I site 3' to the amplified cpIII fragment. The reaction and purification of the PCR product was performed as described above. The sequence of the resultant PCR modified cpIII DNA fragment having a 5' Nhe I and 3' EcoR I restriction site is listed in the Sequence Listing as SEQ ID NO:87.

An alternative Lac-B primer for use in constructing the cpIII membrane anchor and LacZ promotor region was Lac-B' as shown in Table 5. The amplification reactions were performed as described above with the exception that in the second PCR amplification, Lac-B' was used with Lac-F instead of Lac-B. The product from the amplification reaction is listed in the sequence listing as SEQ ID NO:87 from nucleotide position 1 to nucleotide position 172. The use of Lac-B' resulted in a LacZ region lacking 29 nucleotides on the 3' end but was functionally equivalent to the longer fragment produced with the Lac-F and Lac-B primers.

The products of the first and second PCR amplifications using the primer pairs 6-3(F) and 6-3(B) and Lac-F and Lac-B were then recombined at the nucleotides corresponding to cpIII membrane anchor overlap and Nhe I restriction site and subjected to a second round of PCR using the G3-F (SEQ ID NO:79) and Lac-B (SEQ ID NO:82) primer pair to form a recombined PCR DNA fragment product consisting of the following: a 5' Spe I restriction site; a cpIII DNA membrane anchor domain beginning at the nucleotide residue sequence which corresponds to the amino acid residue 198 of the entire mature cpIII protein; an endogenous stop site provided by the membrane anchor at amino acid residue number 112; a Nhe I restriction site, a LacZ promoter, operator and Cap-binding site sequence; and a 3' EcoR I restriction site. The recombined PCR modified cpIII membrane anchor domain DNA fragment was then restriction digested with Spe I and EcoR I to produce a DNA fragment for directional ligation into a pComb2 phagemid expression vector having only one Spe I site prepared in Example 1a(iv) to form a pComb2-III (also referred to as pComb2-III) phagemid expression vector as described in Example 1b(ii).

h. Isolation of Anti-NPN Coding $V_H$ DNA Segment

To prepare modified Fd fragments for recombination with the PCR modified cpVIII membrane anchor domain fragment to form a Fd-cpVIII DNA fusion product, PCR amplification as described above was performed using Clone 2b, prepared in Example 2f, as a template. The primers, Hc3 (SEQ ID NO:77) and AK 7 (SEQ ID NO:78), the sequences of which are listed in Table 5, were used in PCR to amplify the Fd portion of the Clone 2b and incorporate Xho I and Spe I cloning sites along with a cpVIII overlapping sequence. The amplified PCR modified Fd product was purified, electrophoresed and isolated from 1% agarose gels as described above. The size of the Fd fragment was 680 base pairs.

i. Preparation of a DNA Segment Encoding a Portion of the Fusion Protein Fd-cpVIII The purified PCR modified Fd DNA fragment containing cpVIII overlapping nucleotide sequences prepared above was then admixed with the PCR modified cpVIII membrane anchor domain fragment to form an admixture. The fragments in the admixture were allowed to recombine at their complementary regions. The admixture containing the recombined PCR fragments was then subjected to a second round of PCR amplification as described above using the end primer pair AK 6 (SEQ ID NO:76) and Hc3 (SEQ ID NO:77) (Table 5). The corresponding product of the PCR amplification was purified and electrophoresed on agarose gels as described above. The PCR product was determined to be approximately 830 base pairs (Fd=680+150) confirming the fusion of Fd with cpVIII. The sequence of the PCR product linking the Fd sequence with the cpVIII sequence in frame in a 5' to 3' direction is listed as SEQ ID NO 88. The Fd-cpVIII fusion product was then used in directional ligations described in Example 2j for the construction of a pCBAK8-2b dicistronic phagemid expression vector.

j. Construction of pCBAK8-2b Dicistronic Expression Vector

To construct a phagemid vector for the coordinate expression of a Fd-cpVIII fusion protein with kappa light chain, the PCR amplified Fd-cpVIII fusion product prepared in above in Example 2i is first ligated into Clone 2b phagemid expression vector isolated from the NPN combinatorial library prepared in Example 2f. For the ligation, the Fd-cpVIII PCR fusion product is first restriction digested with Xho I and EcoR I. Clone 2b phagemid vector is similarly digested resulting in the removal of the cloning and decapeptide regions. The digested Fd-cpVIII fragment is admixed and ligated into the digested Clone 2b at the cohesive termini generated by Xho I and EcoR I restriction digestion. The ligation results in operatively linking the nucleotide residue sequence encoding the Fd-cpVIII polypeptide fusion protein to a second cassette having the nucleotide residue sequences encoding the ribosome binding site, a pelB leader sequence and the kappa light chain already present in Clone 2b to form a dicistronic DNA molecule in the original Clone 2b phagemid expression vector.

E. coli, strain TG1, is then transformed with the phagemid containing the dicistronic DNA molecule and transformants are selected on ampicillin as the original Clone 2b contained an ampicillin selectable resistance marker gene. For high efficiency electro-transformation of E. coli, a 1:100 volume of an overnight culture of TG1 cells is inoculated into one liter of L-broth (1% Bacto tryptone, 0.5% Bacto yeast extract, 0.5% NaCl). The cell suspension is maintained at 37 C. with vigorous shaking to a absorbance at 600 nm of 0.5 to 1.0. The cell suspension in log phase growth is then harvested by first chilling the flask on ice for 15 to 30 minutes followed by centrifugation in a cold rotor at 4000×g for 15 minutes to pellet the bacteria. The resultant supernatant is removed and the bacterial cell pellet is resuspended in a total of one liter of cold water to form a cell suspension. The centrifugation and resuspension procedure is repeated two more times and after the final centrifugation, the cell pellet is resuspended in 20 ml of cold 10% glycerol. The resuspended cell suspension is then centrifuged to form a cell pellet. The resultant cell pellet is resuspended to a final volume of 2 to 3 ml in cold 10% glycerol resulting in a cell concentration of 1 to $3 \times 10^{10}$ cells/ml. For the electro-transformation procedure, 40 ul of the prepared cell suspension is admixed with 1 to 2 ul of phagemid DNA to form a cell-phagemid DNA admixture. The resultant admixture is mixed and allowed to sit on ice for one minute. An electroporation apparatus, for example a Gene Pulsar, is set a 25 uF and 2.5 kV. The pulse controller is set to 200 ohms. The cell-DNA admixture is transferred to a cold 0.2 cm electroporation cuvette. The cuvette is then placed in the chilled safety chamber and pulsed once at the above settings. To the pulsed admixture, 1 ml of SOC medium is then admixed and the cells are resuspended with a Pasteur pipette (SOC medium is prepared by admixing 2% Bacto tryptone, 0.5% Bacto yeast extract, 10 mM NaCl, 2.5 mM KCl, 10 mM $MgCl_2$, 10 mM $MgSO_4$, and 20 mM glucose). The cells suspension is then transferred to a 17×100 mm polypropylene tube and maintained at 37 C. for 1 hour. After the maintenance period, the transformed TG1 cells are then plated on ampicillin LB plates for selection of ampicillin resistant colonies containing the phagemid which provides the selectable marker gene.

Ampicillin resistant colonies are selected and analyzed for the correct insert size and expression of Fab. Briefly, DNA minipreps of selected colonies are prepared for the isolation of phagemid DNA. The isolated phagemid DNA from each miniprep is restriction digested with Xho I and EcoR I and the digests were electrophoresed on a 1% agarose gel. Clone AK16 is selected as an 830 bp fragment is visualized on the gels confirming the insertion of the Fd-cpVIII PCR fusion product into digested Clone 2b.

Clone AK16 phagemid is then restriction digested with Xho I and Xba I and the nucleotide residue sequence of the dicistronic DNA molecule encoding the Fd-cpVIII fusion protein, the ribosome binding site and pelB leader sequence for expression of the light chain, a spacer region and the 2b kappa light chain is isolated by agarose gel electrophoresis. The isolated dicistronic DNA fragment is then ligated into a Xho I and Xba I restriction digested pCBAKO expression vector prepared in Example 1c(ii) to form a dicistronic phagemid expression vector designated pCBAK8-2b.

The resultant pCBAK8-2b expression vector consists of nucleotide residue sequences encoding the following elements: f1 filamentous phage origin of replication; a chloramphenicol acetyl transferase selectable resistance marker gene; an inducible LacZ promoter upstream from the LacZ gene; a multiple cloning site flanked by T3 and T7 polymerase promoters; and the dicistronic DNA molecule (a first cassette consisting of a ribosome binding site, a pelB leader, and a Fd-cpVIII DNA fusion product operatively linked to a second cassette consisting of a second ribosome binding site, a second pelB leader, and a kappa light chain).

k. Construction of pCBAK3-2b Dicistronic Expression Vector

To construct a phagemid vector for the coordinate expression of a Fd-cpIII fusion protein with kappa light chain, the PCR amplified and recombined cpIII membrane anchor and LacZ promotor region fragment prepared in Example 2g having a 5' Spe I and 3' EcoR I restriction site is first directionally ligated into a pComb2 phagemid expression vector previously digested with Spe I and EcoR I prepared in Example 1a(iv) to form a pComb2-3 (also called pComb2-III) phagemid vector. See Example 1b(ii) for details of vector construction. This vector is used in this invention when ampicillin resistant vectors are preferred. Thus, the resultant pComb2-3 vector, having only one Spe I restriction site, contains separate LacZ promoter/operator sequences for directing the separate expression of the heavy chain (Fd)-cpIII fusion product and the light chain protein. The expressed proteins are directed to the periplasmic space by pelB leader sequences for functional assembly on the membrane. Inclusion of the phage F1 intergenic region in the vector allows for packaging of single stranded phagemid with the aid of helper phage. The use of helper phage superinfection leads to expression of two forms of cpIII. Thus, normal phage morphogenesis is perturbed by competition between the Fab-cpIII fusion and the native cpIII of the helper phage for incorporation into the virion as schematically shown in FIG. 6 for Fab-cpVIII fusions.

For producing chloramphenicol resistant vectors for use in this invention, the resultant pComb2-3 phagemid vector is then restriction digested with Sac II and Apa I to form an isolated fragment. The resultant isolated fragment containing the expression control sequences and the cpIII sequence is then directionally ligated into a similarly digested pCBAKO phagemid vector prepared in Example 1c(ii) to form a pCBAK3 phagemid expression vector. This vector lacks Fd and kappa light chain sequences.

A chloramphenicol-resistant phagemid expression vector, pCBAK3-2b, for the expression of a fusion protein and kappa light chain is then constructed. Briefly, the pCBAK3 phagemid expression vector prepared above is first digested with Xho I and Spe I to form a linearized pCBAK3 phagemid expression vector. PCR amplified and modified Fd fragment, prepared in Example 2h containing Xho I and Spe I sites, is subsequently restriction digested with Xho I and Spe I. The resultant Fd fragment is then directionally ligated via cohesive termini into the Xho I and Spe I restriction digested pCBAK3 phagemid expression vector to form a second phagemid expression vector in which the PCR modified Fd fragment is operatively linked in-frame to nucleotide residue sequences encoding cpIII. E. coli strain XL1-Blue (Stratagene) is then transformed with the above phagemid vector containing Fd-cpIII. Transformants containing the Fd-cpIII encoding phagemid are selected on chloramphenicol. Phagemid DNA is isolated from chloramphenicol resistant clones and is restriction digested with Sac I and Xba I to form a linearized phagemid expression vector into which a Sac I and Xba I light chain fragment prepared below is directionally ligated.

Phagemid Clone 2b, isolated from the original combinatorial library as described in Example 2a, is restriction digested with Sac I and Xba I to isolate the nucleotide residue sequence encoding the kappa light chain. The isolated kappa light chain sequence is then directionally ligated into the Sac I and Xba I restriction digested phagemid expression vector prepared above containing Fd-cpIII to form the phagemid expression vector, pCBAK3-2b. The resultant vector contains the nucleotide residue sequence of a dicistronic DNA molecule for the coordinate expression of a Fd-cpIII fusion protein with kappa light chain. The resultant phagemid expression vector consists of nucleotide residue sequences encoding the following elements: f1 filamentous phage origin of replication; a chloramphenicol acetyl transferase selectable resistance marker gene; an inducible LacZ promoter upstream from the LacZ gene; a multiple cloning site flanked by T3 and T7 polymerase promoters; and the dicistronic molecule (a first cassette consisting of a first ribosome binding site and pelB leader operatively linked to Fd-cpIII operatively linked to a second cassette consisting of a second LacZ, a second ribosome binding site, and a second pelB leader operatively linked to a kappa light chain).

XL1-Blue cells are then transformed with the phagemid expression vector pCBAK3-2b. Transformed colonies containing the chloramphenicol resistant phagemids are selected as described above and analyzed for the correct size insert and expression of Fab as described in Example 2j. Following verification of the insert and expression of Fab in the pCBAK3-2b phagemid vector, XL1-Blue cells are then transformed and induced for the expression of Fab antibodies as described in Examples 3 and 4.

The results of the expression, selection and screening of the Fab-cpIII fusions reveals an advantage of monovalent display provided by Fab-cpIII fusions over multivalent displays provided by Fab-cpVIII fusions as it allowed for the sorting of clones based on affinity as well as specificity, as does the immune system. A 253-fold enrichment of the tight binding clone 10 C. over the weaker binding clone 7E was obtained using the pComb3 system as described in Barbas et al., Proc. Natl. Acad. Sci., USA, 88:7978–7982 (1991).

Studies with peptide libraries on phage that displayed four to five copies of the peptide on the phage surface have shown that multivalency prevented the separation of phage displaying moderate affinity peptides ($10^{-6}$M) from those displaying high affinity peptides ($10^{-9}$M). Cwirla et al., Proc. Natl. Acad. Sci., USA, 87:6378–6382 (1990). Multivalency leads to a chelation effect that reduces the ability to discriminate between phage-bearing high affinity Fabs from those bearing low affinity Fabs.

The use of the system was further demonstrated by sorting a previously characterized (one binder per 5000 clones) human combinatorial antitetanus toxoid Fab library as described by Persson et al., Proc. Natl. Acad. Sci., USA, 88: 2432–2436 (1991). The library, originally in a lambda phage vector system, was reconstructed in pComb2-3 retaining the original pairings of heavy and light chains. The library size, $10^7$ clones was 10-fold larger than the original lambda phage library. After a single round of panning, 13 or 57 clones picked were determined to be tetanus toxoid binders which represented a $10^3$-fold enrichment. Following the third panning, the phage yield had increased 200-fold, indicating enrichment of specific phage. All the clones were thus antigen-specific binders. Large combinatorial libraries of $10^8$ members are thus accessible using this system. Even larger libraries can be achieved by mutagenesis.

3. Expression of Anti-NPN Heterodimer on Phage Surfaces

For expression of antibody Fab directed against NPN on phage surfaces, XL1-Blue cells are separately transformed with the phagemid vectors, pCBAK8-2b and pCBAK3-2b, prepared in Examples 2j and 2k, respectively. The transformants are selected on LB plates containing 30 ug/ml chloramphenicol. Antibiotic resistant colonies are selected for each phagemid transformation and grown in liquid cultures at 37 C. in super broth (super broth is prepared by admixing the following: 20 g 3 [N-Morpholino] propanesulfonic acid (MOPS); 60 g tryptone; 40 g yeast extract; and 2 liters of water; adjust pH to 7.0 with 10M NaOH) containing 30 ug/ml chloramphenicol and 12.5 ug/ml tetracycline for the respective antibiotic selection of the phagemid and the F' episome. The antibiotic resistant transformed XL1-Blue cells are diluted to an optical density ($OD_{600nm}$) of 0.4 in super broth. The inducer, isopropyl thiogalactopyranoside (IPTG), is admixed to the bacterial suspension for a final concentration of 1 mM and the admixture is maintained at 37 C. for 1 hour to induce the expression of the fusion protein and kappa light chain from the LacZ promoter. Helper phage, either R408 or VCS M13 (Stratagene), is then admixed to the induced bacterial suspension at a ratio of 10–20 helper phage to 1 transformed bacterial cell to initiate the generation of copies of the sense strand of the phagemid DNA. The admixture containing the helper phage is then maintained for an additional 2 hours at 37 C. to allow for filamentous bacteriophage assembly wherein the expressed anti-NPN Fab antibodies fused to either bacteriophage membrane anchor domains of cpVIII or cpIII were incorporated into surface of the bacteriophage particles. The bacterial suspension is then centrifuged resulting in a bacterial cell pellet and a supernatant containing phage. The supernatant is removed, collected and assayed as described below for the presence of functional anti-NPN Fab molecules anchored to the phage particles by either cpVIII or cpIII.

4. Phage Elisa Assay for Verifying the Presence and Function of Anti-NPN Heterodimer on the Surface of Filamentous Phage Microtitration plates are coated with NPN-BSA conjugate (0.1 ml, 1 ug/ml in 0.1M Tris-HCl at pH 9.2), and blocked with 1% BSA in PBS. Serial two fold dilutions of pCBAK8-2b derived phage (0.1 ml), prepared in Example 3, are mixed to the pre-coated microtitration plate and maintained for 3 hours at ambient temperature or 16 hours at 4 C. The plates are washed with PBS and goat anti-kappa alkaline phosphatase conjugate (Fisher Biotech, Pittsburgh, Pa.) added (0.1 ml diluted 1/1000 in PBS containing 0.1% BSA) and incubated for 2 hours at room temperature. The plates are washed in PBS and substrate added (0.1 ml, 1 mg/ml para-nitrophenylphosphate in 0.1M Tris-HCl at pH 9.5, containing 50 mM $MgCl_2$). After incubation at 37 C. for signal development, the optical densities at 400 nm are determined. Competition assays are performed with the addition of increasing amounts of free NPN hapten ranging from zero up to 5 mg/well.

For a signal to be generated in this assay, the phage particle must (i) have functionally associated Fd and kappa chains and (ii) be multivalent. Specificity of the particle was assessed by inhibiting binding to the plate in the presence of increasing concentrations free hapten. The generated phage particles exhibit binding to solid phase of the ELISA and can be inhibited by addition of hapten. The assay is used to demonstrate the functional assembly of antibody heavy and light chain polypeptides to form an epitope-binding complex that is present on the surface of the phage particle and able to bind the preselected ligand chapter containing an epitope.

5. Preparation of Alkaline Phosphatase-Containing Phagemid Expression Vectors for Use in the PhoPhab System A system of this invention has now been created by incorporating alkaline phosphatase and antibody Fab's from combinatorial libraries on a filamentous phage framework. In order to further the production of combinatorial antibody libraries, and to expedite immunoassay procedures, a PhoPhab (phosphatase-filamentous phage-antibody Fab fragment) system was developed. PhoPhabs produced by the methods of this invention are antigen specific and can replace antibodies. Unlike more time consuming traditional methods, the PhoPhab system and method does not require expensive cell culture and it is possible to perform immunochemical techniques such as ELISA's without isolating soluble antibodies. Most importantly, when PhoPhabs are produced from a semi-synthetic filamentous phage library [Barbas et al., *Proc. Natl. Acad. Sci., USA,* 89:4457–4461 (1992), the disclosure of which is hereby incorporated by reference] no immunizations are required to produce an antigen-specific reagent.

Phage display systems have been used to expedite the screening of large libraries ($10^7$–$10^8$ members) of randomly combined heavy and light chain fragments for the ability to bind antigen. See, Barbas et al., *Proc. Natl. Acad. Sci., USA,* 88:7978–7982 (1991) and Clackson et al., *Nature,* 352:624–628 (1991). Libraries such as these and those described in Examples 1–3 were constructed by PCR cloning of separate variable heavy and light chains from tissue of immunized subjects or from previously constructed libraries with randomized sequences. These chains were randomly paired in the phagemid expression vector pComb3 or pComb8 as described herein, resulting in a respective fusion of the heavy chain to a fragment of the filamentous phage coat protein 3 or 8. *E. coli* were subsequently transformed with the phagemid expression vector and thus contained a single strand of the vector DNA encoding the nucleotide sequence of the displayed heavy and light chains comprising the Fab. Phage that were extruded from the transformed *E. coli* have the Fab fragment fused to a region on the phage particle, the location of which is dependent on the anchor protein. This phagemid expression system thus links both the processes of recognition and replication in a single phage particle.

In a process called panning as described by Parmley et al., *Gene,* 74:305–318 (1988), the phage expressing antigen binding pairs of heavy and light chains are enriched and isolated. Human Fab's to HIV, as described by Burton et al., *Proc. Natl. Acad. Sci., USA,* 88:10134–10137 (1991), as well as mouse Fab's to a variety of antigens have been isolated by these methods. For the latter see, Kang et al., *Proc. Natl. Acad. Sci., USA,* 88:4363–4366 (1991). In addition to antibodies, bacterial alkaline phosphatase (also referred to as BAP) (E.C. 3.1.3.1, the PhoA gene product) has been attached to the gene III protein and shown to be active as described by McCafferty et al., *Protein Eng.,* 4:955–961 (1991), the disclosure of which is hereby incorporated by reference. The resulting enzyme phage showed phosphatase activity and could be purified on an affinity column. These results are significant because BAP is usually required to be a dimer to show activity (McCracken et al., *J. Biol. Chem.,* 255:2396–2404 (1980). To explain the activity on phage, McCafferty et al., supra, (1991) suggested that two BAP-gene III fusions could associate on the phage to give enzymatically active dimers.

Figure 7:
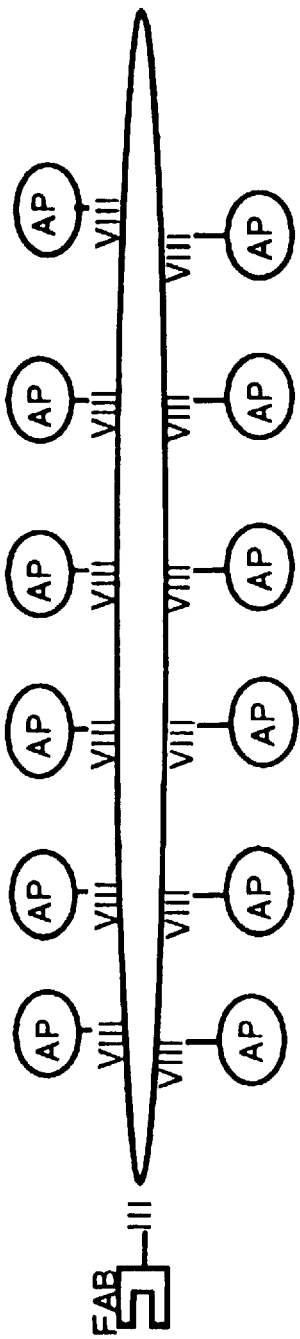
FIG. 7 is a schematic representation of a PhoPhab of this invention as described in Examples 6 and 7. The heterodimeric receptor Fab is anchored to coat protein III at the tail of the phage while the alkaline phosphatase indicator protein is anchored to the coat protein VIII along the length of the phage.

In addition to the 5 copies of the gene III protein located at the tip of filamentous phage particles, the gene VIII protein (cp8 or cpVIII), which comprises the shaft of the particle and has approximately 2700 copies of the cpVIII protein, can be used for anchoring proteins to the surface of filamentous phage as shown herein and as described by Kang et al., supra (1991) and Gram et al., *Proc. Natl. Acad. Sci., USA,* 89:3576–3580 (1992). It has now been discovered that the phage can be used as a framework to link a Fab-cpIII fusion to multiple copies of alkaline phosphatase-cpVIII fusion as illustrated in FIG. 7. The Fab-phage-alkaline phosphatase conjugates of this invention, designated PhoPhabs, are specific one-step reagents for ELISA's.

To produce the doubly conjugated phage of this invention, a second expression vector designated as pPho8cat was constructed so that antigen-binding clones from the pComb3 system could be directly converted into PhoPhabs. The construction of the pPho8cat expression vector for use in this invention is presented Example 5a below. A preferred vector also described in Example 5a is a modified pPho8cat which lacks a Bsp H1 and Hind III 1221 bp fragment containing the extraneous f1 origin of replication. This modified vector is designated as pPho8B as shown in FIG. 14A. In addition, also contemplated for use in the production of doubly conjugated phage is an expression vector designated pPhoL8. This vector is a modification of pPho8cat in that is has a linker region of 60 nucleotides positioned between the sequence encoding the alkaline phosphatase indicator protein and the sequence encoding the phage coat protein 8 anchor. The linker encodes the repeated amino acid residue sequence (Glu-Gly-Gly-Gly-Ser)$_4$ (SEQ ID NO:91). The presence of the linker provides for the preferred dimerization of the expressed alkaline phosphatase protein on the surface of the phage, which allows for the amplification of the detectable signal. The construction of the pPhoL8 expression vector for use in this invention is presented Example 5b below. A further modified vector, designated pPhoL8B, is the pPho8B vector containing the linker sequence described above. This vector is described in Example 5d and shown in FIG. 14B.

Another preferred vector for use in this invention is pPhoC that contains an amber stop positioned 3' to the end of the alkaline phosphatase gene that provides for the expression of soluble alkaline phosphatase indicator protein. The pPhoC expression vector is described in Example 8 and shown in FIG. 14C.

a. Construction of pPho8 CAT

To produce a pPho8CAT expression vector for use in this invention, the alkaline phosphatase gene phoA was first cloned from *E. coli* strain XL1-Blue (Stratagene) by PCR as described in Example 2c with the oligonucleotide 5' primer, PHO5 5'-CAGCTGCTCGAGCGGACACCAGAAATGCCTGTT-3' (SEQ ID NO:92) and a 3' primer, PHO3 5'-AGGCTTACTAGTTTTCAGCCCCAGAGCGGCTTT-3' (SEQ ID NO:93). The primers, synthesized by Operon Technologies, Alameda, Calif., were based upon the published sequence of the alkaline phosphatase gene hereinafter referred to as PhoA as described by Chang et al., *Gene*, 44:121–125 (1986), the disclosure of which is hereby incorporated by reference. In addition, the primers were designed to incorporate into the ends of the PhoA nucleotide sequence the restriction endonuclease cloning sites, Xho I and Spe I, which are underlined in the 5' and 3' primers, respectively. After digestion with Xho I and Spe I, the insert was directionally ligated into the pComb2-8 expression vector prepared in Example 1b(i) resulting in the positioning of the PhoA PCR amplified insert between the 5' pelB signal peptide and the 3' nucleotide sequence encoding cpVIII fused to the C-terminus. The resultant expression vector DNA was then transformed into XL1-Blue cells. The transformants in XL1-Blue cells were selected by plating on LB agar containing 100 mg/ml carbenicillin for ampicillin resistance, 0.1 mM phosphate, and 5-bromo-4-chloroindoyl phosphate (X-P), the substrate for alkaline phosphatase, at a concentration of 40 ug/ml.

A blue colony having the inserted vector was selected and plasmid DNA was isolated. The resultant plasmid DNA was then digested with Eag I resulting in the isolation of a 2458 bp fragment containing the transcription unit of pComb2-8 having the following elements listed in 5' to 3' direction: a ribosome binding site; a pelB leader sequence; a spacer sequence encoding 5 amino acids; an Xho I restriction site followed by the PhoA nucleotide sequence; a Spe I restriction site followed by the cpVIII nucleotide sequence; and a nucleotide stop signal followed by the restriction sites EcoR I and Xba I.

Figure 9:
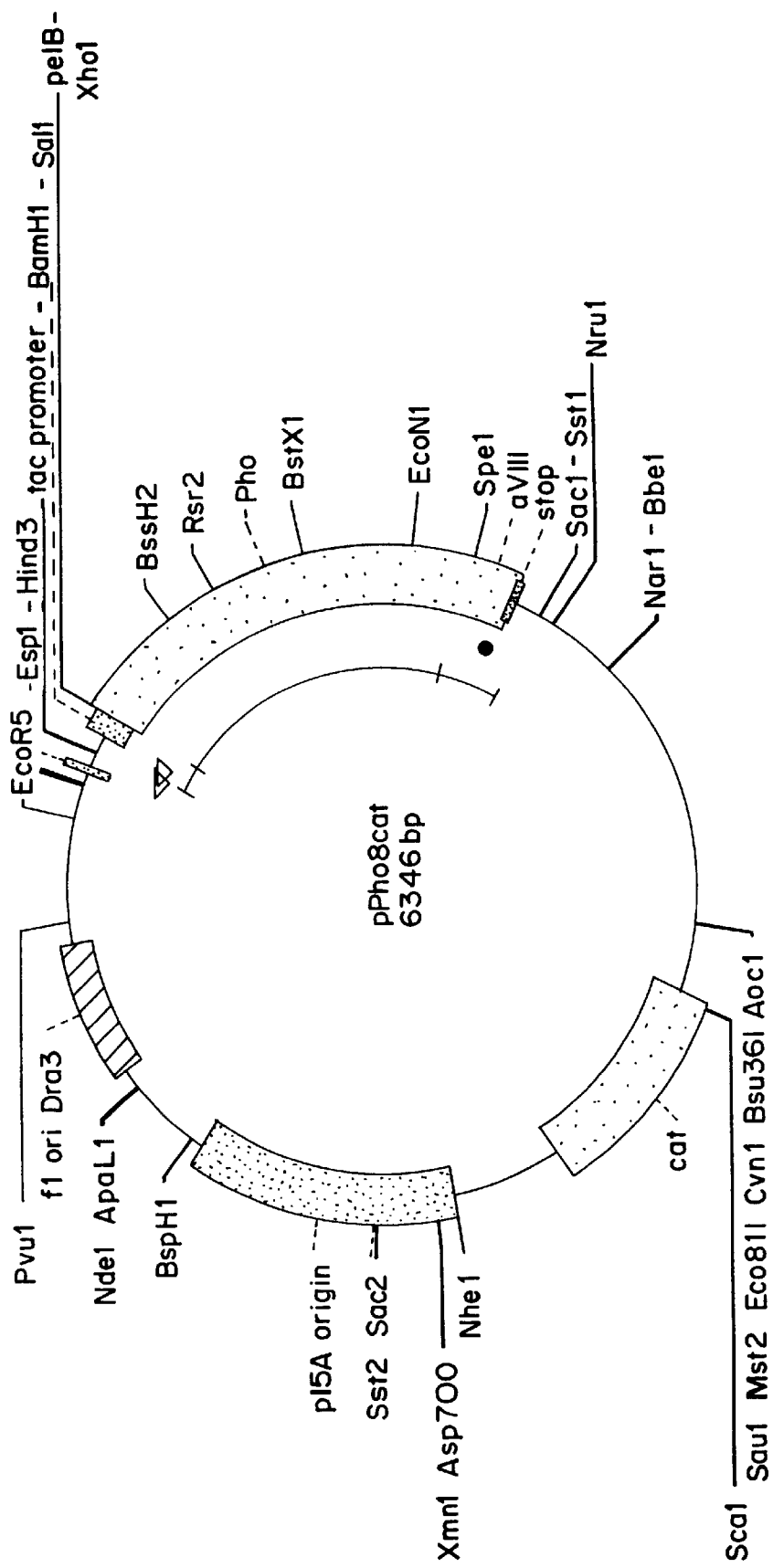
FIG. 9 is a schematic representation of the 6346 base pair pPho8cat expression vector prepared as described in Example 5a. Expression of the alkaline phosphatase-cPVIII fusion protein is driven by the tac promoter. The region of nucleotides encoding alkaline phosphatase is indicated as Pho. The nucleotide sequence encoding the coat protein VIII is located 3' to the Pho site and is indicated as gVIII. The construct contains the cat gene for conferring chloramphicol resistance. Both a p15A origin and a f1 ori are present in the vector. Various restriction endonuclease cloning sites are indicated.

This operative fragment was then ligated into the Eag I site in the expression vector pFL261. A schematic of the fragment inserted into pFL261 is shown in FIG. 8. The amino and carboxy terminus of the PhoA amino acid residue sequence is indicated between the Xho I and Spe I sites beginning with RTP (Arg-Thr-Pro) and ending with LK (Leu-Lys). The pFL261 expression vector used in this invention has been described by Larimer et al., *Protein Eng.*, 3:227–231 (1990), the disclosure of which is hereby incorporated by reference. The complete nucleotide sequence of pFL261 is in the EMBL, GenBank and DDBJ Nucleotide Sequence Databases under the accession number M29363. A clone with the correct orientation was identified by restriction digests with Xba I and the ability to hydrolyze X-P as described by McCafferty et al., *Protein Eng.*, 4:955–961 (1991). The resulting plasmid of 6346 bp having the PhoA gene operatively linked to the nucleotide sequence encoding the anchor protein cpVIII in the correct orientation was designated as pPho8cat. This plasmid contained the p15A origin of replication and the chloramphenicol acyl transferase (CAT) gene conferring chloramphenicol resistance, as well as the PhoA-cpVIII fusion under control of the tac promoter. A schematic of the pPho8cat construct is shown in FIG. 9. The p15A origin is compatible with the colE1 origin on pComb3 as well as pComb2-3, allowing stable double transformants, PhoPhabs, to be created. Other host vectors similar to pFL261 are contemplated for use in this invention to make PhoPhabs.

b. Construction of pPho8B

Figure 10:
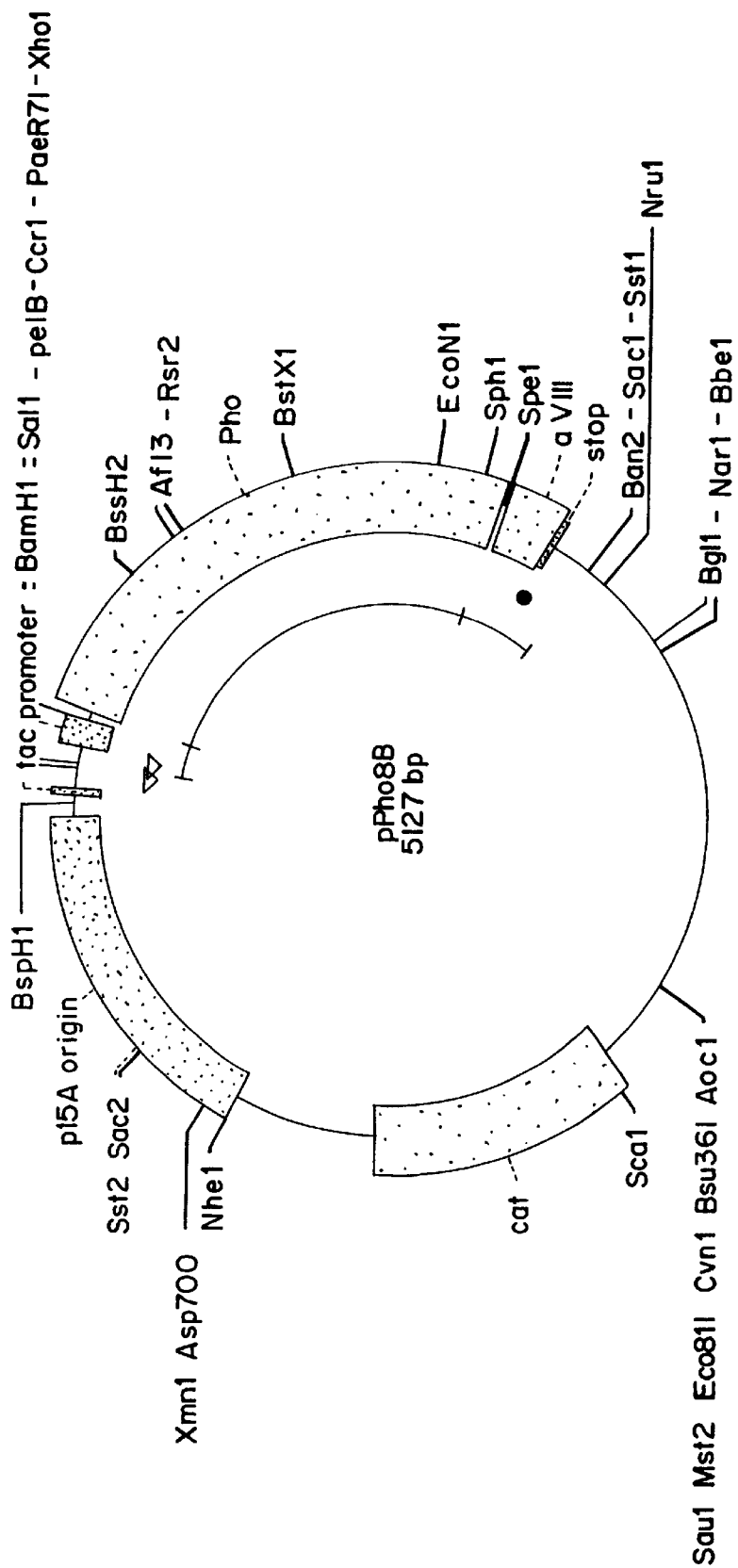
FIG. 10 is a schematic representation of the 5127 base pair pPho8B expression vector lacking a f1 origin of replication (f1 ori) as shown in the parent pPho8cat vector from which pPho8B was derived as described in Example 5a. The rest of the construct has the other elements as described in FIG. 9.

A preferred vector for use in this invention is a modified pPho8cat which lacks a Bsp H1 and Hind III 1221 bp fragment containing the extraneous f1 origin of replication. This modified vector of 5127 bp is designated as pPho8B. A schematic of the pPho8B construct is shown in FIG. 10 and also in FIG. 14A. Since the pPho8B vector lacks an f1 origin of replication, the single stranded DNA produced after rescue with helper phage will not be incorporated into the resultant phage, thereby improving the screening for phage having single stranded DNA from the pComb2-3 heterodimeric polypeptide expression vectors prepared in this invention and described below in Example 7. Selection and screening for pPho8B vectors was performed as described above for pPho8cat.

c. Construction of pPhoL8

Also contemplated for use in this invention in the production of doubly conjugated phage is an expression vector designated pPhoL8. This vector is a modification of pPho8cat in that it has a linker region of 60 nucleotides positioned between the sequence encoding the alkaline phosphatase indicator protein and the sequence encoding PhoA, the phage coat protein 8 anchor. The linker encodes the repeated amino acid residue sequence (Glu-Gly-Gly-Gly-Ser)$_4$ (SEQ ID NO:91). The presence of the linker provides for the preferred dimerization of the expressed alkaline phosphatase protein on the surface of the phage.

To construct pPhoL8, pComb2-8 was first digested with Spe I and the single-stranded nucleotide overhangs were digested with Mung Bean Nuclease to produce a linearized blunt-ended pComb2-8 expression vector. A synthetic 63 bp nucleotide insert having the nucleotide sequence 5'-CTAGTGAGGGTGGTGGCT[CTGAGGGTGGCGGTT]$_3$-3' (SEQ ID NO:94) and its corresponding complementary strand were prepared and annealed to form a double-stranded 63 bp nucleotide double-stranded DNA fragment. The resulting fragment was subsequently ligated into the linearized pComb2-8 expression vector forming a circularized vector, designated pComb2-8L. In order to combine the PhoA encoding sequence with the operative fragment of pComb2-8, pPho8cat was digested with Sac I and Spe I releasing a fragment containing the cpVIII coding sequence and forming a linearized pPho8cat vector. The pComb2-8 expression vector containing the linker sequence prepared above, pComb2-8L, was then digested with Sac I and Spe I to isolate a fragment containing the linker operatively linked to the sequence encoding cpVIII. The isolated fragment from pComb2-8 was then inserted into the linearized pPho8cat vector to produce the expression vector pPhoL8.

The resultant pPhoL8 expression vector was then transformed into XL1-Blue cells as described in Example 5a. The transformants in XL1-Blue cells were selected as previously described.

Figure 11:
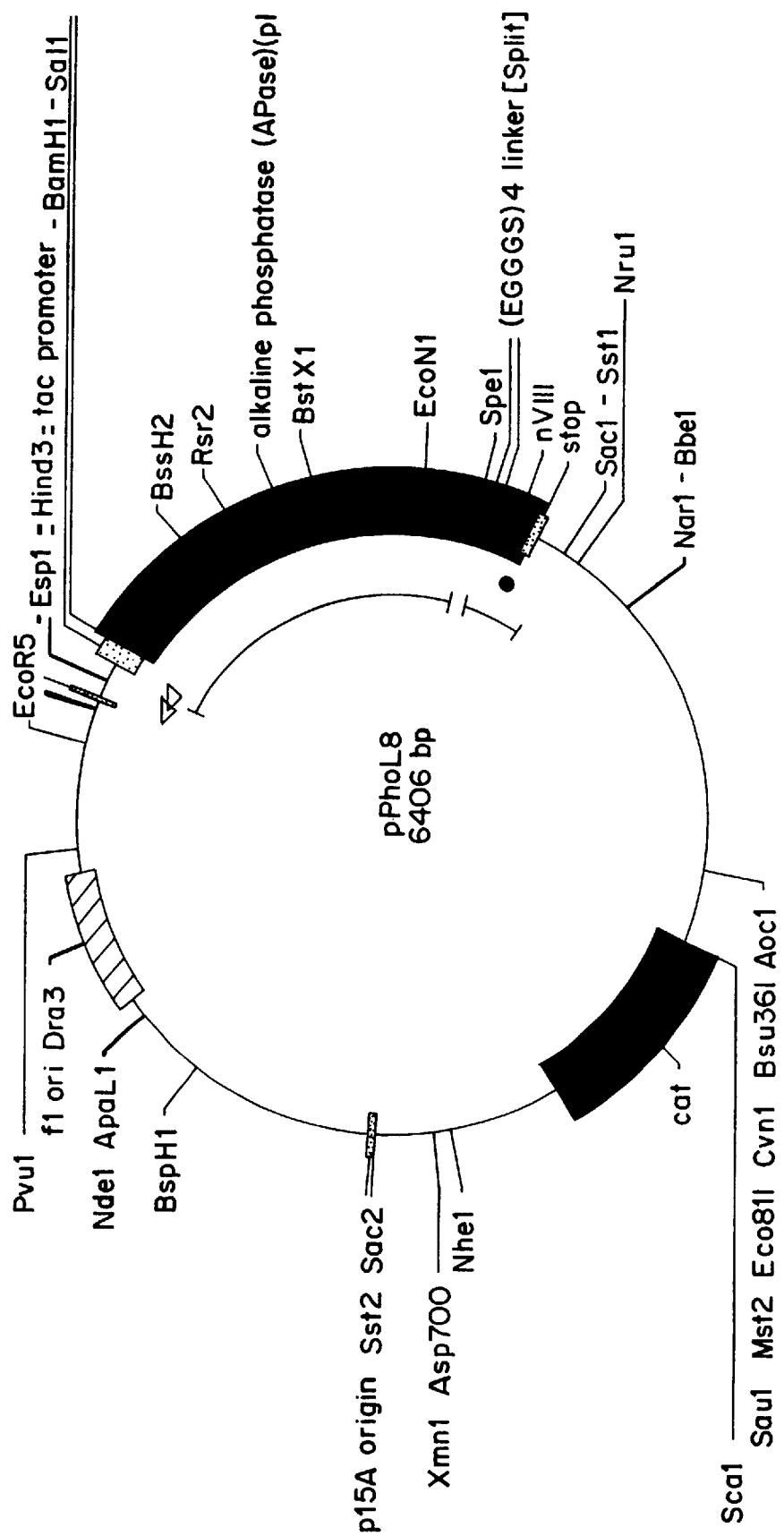
FIG. 11 is a schematic representation of the 6406 base pair pPhoL8 expression vector that contains a 60 nucleotide linker sequence prepared as described in Example 5b. The rest of the construct has the other elements as described in FIG. 9.

This plasmid of 6406 bp contained the p15A origin of replication and the chloramphenicol acyl transferase (CAT) gene conferring chloramphenicol resistance, as well as the PhoA-linker-cpVIII fusion under control of the tac promoter. A schematic of the pPhoL8 construct is shown in FIG. 11. The p15A origin is compatible with the colE1 origin on pComb3 as well as pComb2-3, allowing stable double transformants, PhoPhabs, to be created.

d. Construction of pPhoL8B

Another expression vector, designated pPhoL8B, was derived from pPhoL8, thereby having the linker sequence described in Example 5c. A schematic of the vector is shown in FIG. 14B. In addition, the pPhoL8B vector was constructed to lacked the f1 origin present in pPho8cat and pPhoL8 but absent in pPho8B. The f1 origin was removed by digestion of the pPhoL8 vector with BspH I and Hind III, followed by filling in with Klenow fragment and ligating the blunt ended vector. The pPhoL8B, with the PhoA-linker-cpVIII fusion under control of the tac promoter, had chloramphenicol resistance markers and p15A replicons derived from the parent expression vector pFL261 as described in Example 5a. The p15A origin is compatible with the colE1 origin on pComb3 as well as pComb2-3, allowing stable double transformants, PhoPhabs, to be created.

The resultant pPhoL8B expression vector was then transformed into XL1-Blue cells as described in Example 5a. The transformants in XL1-Blue cells were selected as previously described.

6. Preparation of Stable Double Transformants, PhoPhabs

To test the viability of PhoPhabs as analytical reagents, PhoPhabs specific for several different antigens were created from single clones or libraries enriched for the antigen by panning. See Parmley et al., *Gene*, 74:305–318 (1988) and Burton et al., *Proc. Natl. Acad. Sci., USA*, 88:10134–10137 (1991). The antigens used were fluorescein isothiocyanate conjugated to BSA (Barbas et al., *Proc. Natl. Acad. Sci., USA*. 89:4457–4461 (1992), phosphonamidate haptens PPC (Brinkworth et al., *Bioorg. Med. Chem. Lett.*, 1:653–658 (1991) and Pro1 (Brinkworth et al, ibid) and tetanus toxoid. The Pro1 and PPC libraries were constructed from immunized mice as described in Examples 1–4 for an NPN-specific library and by published procedures as described by Kang et al., *Methods: A Companion to Methods in Enzymology*, 2:111–118 (1991) and Barbas et al., *Methods: A Companion to Methods in Enzymology*, 2:119–124 (1991) and the tetanus toxoid clone P313 was isolated from a library as described by Persson et al., *Proc. Natl. Acad. Sci., USA*, 88:2432–2436 (1991) constructed from an immunized human. The disclosures of the construction of these libraries are hereby incorporated by reference for use in this invention. The fluorescein library was constructed without an immunization with hapten by a semi-synthetic approach in which the CDR3 region of tetanus binder 7E was randomized. Panning the randomized library against fluorescein-BSA gave fluorescein specific binders as described by Barbas et al., *Proc. Natl. Acad. Sci., USA*, 89:4457–4461 (1992), the disclosure of which is hereby incorporated by reference. These semi-synthetic libraries make it possible to obtain antigen specific Fab's without immunizations. Therefore, PhoPhabs constructed from this anti-fluorescein library are synthetic reagents.

PhoPhabs were produced by cotransforming pPho8cat with the respective pComb2-3 libraries and selecting double transformants on LB plates containing 30 ug/ml chloramphenicol and 50 ug/ml carbenicillin. One ml of a fresh overnight culture of the double transformants in strain XL1-Blue maintained in antibiotic medium was then grown as described in Example 3 in liquid cultures in 10 ml of super broth containing 5 mM $MgCl_2$, 0.25 uM $ZnCl_2$ and the antibiotics carbenicillin at a concentration of 12.5 ug/ml, chloramphenicol at a concentration of 3.8 ug/ml and tetracycline at a concentration of 2.5 ug/ml at 37 C.

After one hour, cultures of one double transformant (monoclonal) or approximately 20 (polyclonal) were then infected with $1.2 \times 10^{10}$ pfu of helper phage R408 (Stratagene) and induced with 1 mM IPTG to produce phage particles containing single stranded DNA and expressing both heterodimeric receptors anchored to cpIII and PhoA indicator polypeptide anchored to cpVIII on the phage surface. The admixture was then shaken for 20 minutes at 37 C. The infected admixture was then admixed to 100 ml of SB with 10 mM $MgCl_2$, 1 uM $ZnCl_2$ and the antibiotics carbenicillin at a concentration of 25 ug/ml and chloramphenicol at 5 ug/ml. The admixture was then shaken at 300 rpm in a 2 liter baffle flask with good aeration of 8.5 hours. Following the maintenance period, the suspension was centrifuged at 14,000×g (9 krpm in a JA-10 centrifuge for 15 minutes)

The resultant phage-containing (PhoPhab) supernatant from each culture was precipitated from the supernatants with final concentrations of 4% PEG-8000 and 500 mM NaCl for 1 hour at 4 C. The phage were then pelleted at 15,000 rpm as described above and resuspended in 400 ul of TBS, and used directly in an ELISA described in Example 7.

In addition, cotransformation is not limited to the one-step procedure described herein. Contemplated transformations include two-step single transformations including the incorporation of a derived helper phage in which sequences for conferring kanamycin resistance are present along with the sequences encoding PhoL8 vector.

Cotransformation was also performed using the PhoA-expressing vectors, pPho8B and pPhoLB, prepared in Examples 5a and 5b, respectively. The cotransformation and selection steps were performed in an identical manner to those procedures described above for pPho8cat.

7. Screening of Stable Double Transformants. PhoPhabs

The PhoPhabs produced in Example 6 were then used in ELISA to verify the antigen specificity and to determine specific binding characteristics of the Fab's expressed on the surface of the PhoPhabs.

An ELISA was performed with PhoPhabs against antigens fluorescein-BSA conjugate (FL-BSA), Pro1-BSA, PPC-BSA, tetanus toxoid protein (Tet-tox), phage displaying P313 Fab-gIII but no AP-gVIII conjugate (Tet no pho) and BSA. Antigens were separately coated onto Costar brand EIA plates #3690at a concentration of 0.2 ug in 25 ml of 0.1M $NaHCO_3$ at pH 8.6 or PBS at pH 7.4 at 4 C. overnight. The wells were then blocked with 1% BSA in PBS for 1 hour at 37 C., washed with water, and then 10 ml of 1% BSA and 25 ul of concentrated phage prepared in Example 6 were separately admixed for 30 minutes at 37 C. After washing for 10 cycles on a plate washer, 50 ml of developer (1 mg/ml p-nitrophenyl phosphate, 10% v/v diethanolamine, 1 mM $MgCl_2$, 3 mM $NaN_3$ at pH 9.8) were admixed and the plate was maintained at 37 C. overnight.

Figure 12:
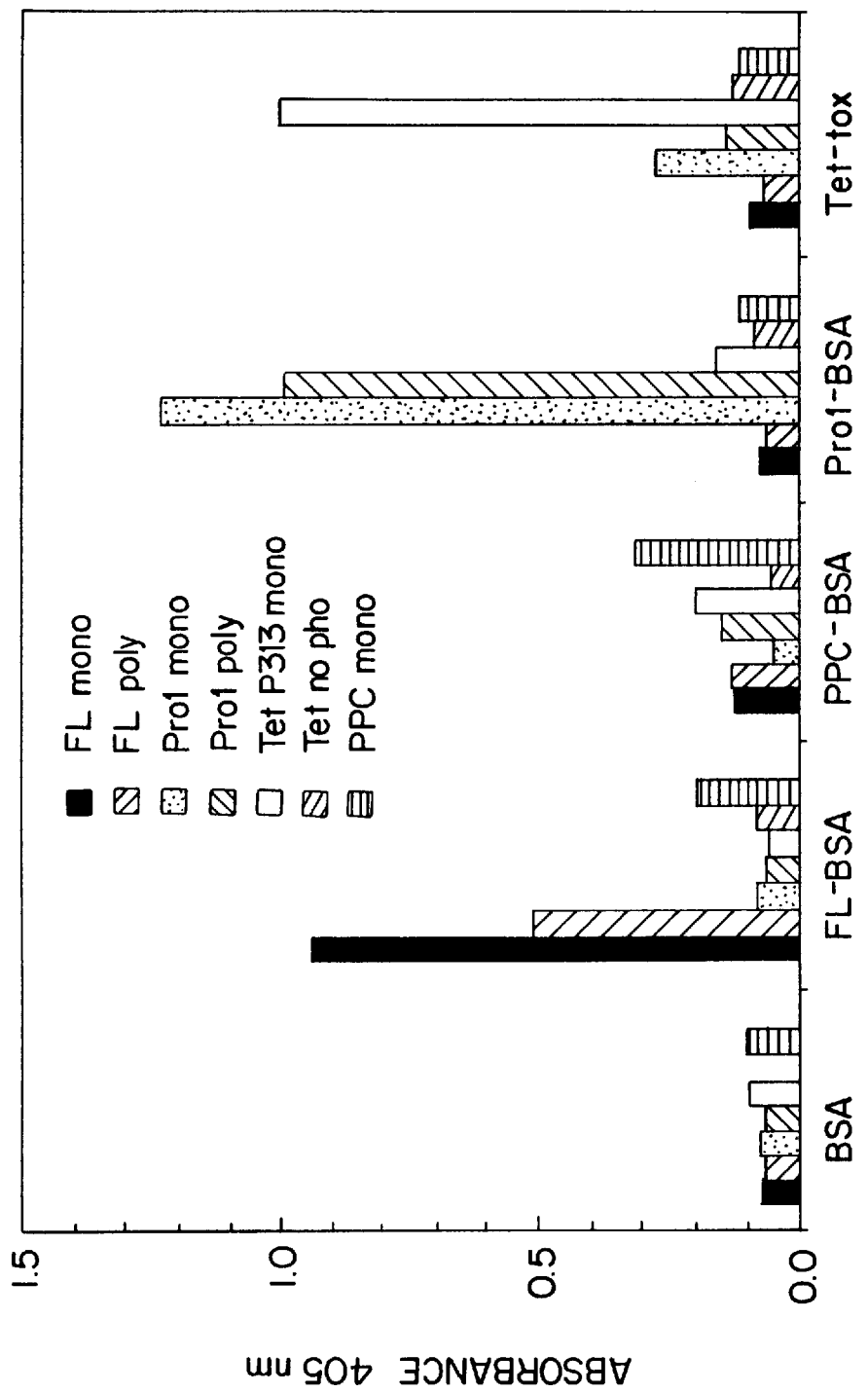
FIG. 12 is a bar graph depicting the results of ELISA assays performed as described in Example 7. The detectable ELISA signal is indicated on the Y-axis as absorbance at 405 nm plotted against the antigens on the X-axis used to coat the wells. The following antigen abbreviations are defined: BSA=bovine serum albumin; FL-BSA=fluorescein-BSA conjugate; PPC-BSA=phosphonamidate hapten conjugate; Pro1-BSA=a different phosphonamidate hapten conjugate; and Tet-tox=tetanus toxoid. The PhoPhabs used to immunoreact with the antigens are indicated in the inset box. The following abbreviations are identified: F1=fluorescein; Pro and PPC=phosphoamidate haptens; Tet=tetanus toxoid; Tet P313 mono=clone isolated from a tetanus toxoid library; Tet no pho=phage displaying P313 Fab-cpVIII without an alkaline phosphatase-cpVIII conjugate; mono=monoclonal and poly=polyclonal mixture of Fab-producing pComb3 clones.

The results of the ELISA with PhoPhabs of this invention prepared with pPho8cat vectors are shown in FIG. 12. The PhoPhabs, indicated in the inset box in the figure, were specific for the same antigen shown on the X-axis of the figure as the antigen against which the library was panned. All of the PhoPhabs used in the ELISA gave clear signals, except for the one directed against PPC-BSA, labeled PPC mono.

In additional ELISA assays with the phage produced from separate cotransformations of pPho8cat, pPho8B and pPhoL8 with the pComb2-3 tetanus toxoid clone P313 that was previously panned against tetanus toxoid, all three alkaline phosphatase-expressing phages of this invention exhibited specific immunoreactivity against the tetanus toxoid antigen. The ELISA was performed as described as above with the exception of binding 0.2 ug of tetanus toxoid per well in 0.1M NaHCO$_3$ at pH 8.6. The nonspecific sites were blocked with 3% BSA for 1 hour at 37 C. Five ul of the phage preparations were separately admixed to each well along with 25 ul of 3% BSA. The plates were maintained for 1 hour at 37 C. and washed and developed as described above.

The results showed that pPho8B had an 405 nm absorbance of 2.0 while pPho8cat and pPhoL8 had the respective absorbances of 1.0 and 0.5. Thus, while all three PhoPhabs of this invention gave detectable signals, the PhoPhab which was produced with the alkaline phosphatase vector, pPho8B, that lacked the extraneous f1 origin still present in pPho8cat, gave the highest detectable signal indicating specific binding to tetanus toxoid.

8. Preparation of Dimerized Alkaline Phosphatase with Enhanced Enzymatic Activity on the Surface of Filamentous Phage While the bacterial alkaline phosphatase expression vector systems prepared above resulted in detectable signals in conjunction with antibody expression vector systems, PhoPhabs, the level of activity of the PhoPhabs suggested that the incorporation of BAP on the phage was much lower than expected, considering that phage have in excess of 2700 copies of the g8p coat protein.

One explanation for the diminished activity is that BAP dimers were unable to assemble on phage as g8p fusions. Another explanation was that the molecular mechanisms for incorporation of fusions of large proteins such as BAP that is approximately 90 kD with coat protein 8 on phage simply do not exist. A more likely possibility was that unpaired BAP-coat protein 8 monomers could also associate with monomers on other phage, resulting in insoluble, useless aggregates. To examine these possibilities, various approaches for attaching BAP dimers to phage were designed.

An improved signal detection system of dimerized alkaline phosphatase has now been achieved. As described below, the greatest signal was the result of a soluble monomer of alkaline phosphatase forming a dimer with alkaline phosphatase anchored to bacteriophage coat protein 8 (also referred to as g8p) with the flexible linker.

A flexible linker/anchor strategy was pursued with the idea that BAP-g8p fusions might be constrained from dimerization, whereas a BAP-linker-g8p fusion might allow sufficient space and flexibility for dimerization on the phage surface. In the event that assembly of BAP-g8p or BAP-linker-g8p fusion homodimers on the phage surface were not possible, a second strategy was pursued. The second strategy was to provide free BAP monomers that might pair with BAP-g8p fusion monomers, giving heterodimers of BAP:BAP-g8p or BAP:BAP-linker-g8p on the phage surface. These two display strategies give four possible combinations, as illustrated in FIG. 13A–D.

To express the different monomers, three vectors were constructed, one for each of the three different monomers. Free BAP monomers are expressed by pPhoC as described below and shown in FIG. 14C, and in the absence of BAP-g8p fusions, the free monomers pair to form free BAP dimer. In addition, pPhoC had a b-lactamase resistance marker and replicon of the colE1 incompatibility group. BAP-g8p fusions are expressed from pPho8B, which utilizes a chloramphenicol resistance marker and p15A replicon. The different resistance markers and replicons allow stable double transformants of pPhoC and pPho8B to be created. Thus free monomeric BAP and BAP-g8p were expressed in the same cell from two plasmids.

The linker chosen to add flexibility between the BAP and g8p domains was prepared as described in Example 5. A synthetic oligonucleotide coding for the amino acid residue sequence repeat (EGGGS)$_4$ (SEQ ID NO:91) was inserted between the BAP and g8p coding regions of pPho8B, giving the BAP-linker-g8p expression vector pPhoL8B. Again, stable double transformants of pPhoC and pPhoL8B were be created, allowing BAP and BAP-linker-g8p to be expressed in the same cell during phage production.

These plasmids were used to examine the hypothetical possibilities for incorporation of BAP dimers on phage, as illustrated in FIG. 13A–D. For example, phage produced from cells containing only pPho8B, which produces BAP-g8p, incorporated BAP-g8p homodimers on the phage surface with each half of the dimer anchored to the phage coat g8p, illustrated by FIG. 13A. Similarly, phage produced in the presence of induced pPhoLB incorporated BAP-linker-g8p homodimers, as shown in FIG. 13B. For the possibilities where the enzyme was only attached to phage by fusion of one of its dimeric halves to g8p, the double plasmid system was used. For example, phage produced from cells containing pPhoC and pPho8B carried a BAP:BAP-g8p heterodimer, as shown in FIG. 13C.

In addition to the desired heterodimer, the double plasmid systems also produced unwanted homodimers. For example, the pPhoC plus pPho8B system potentially produces three different enzyme dimers: BAP:BAP, BAP:BAP-g8p, and BAP-g8p:BAP-g8p. In theory, phage produced in the presence of a double plasmid system could have such a mixture of heterodimers and homodimers on their surface. However, the incorporation of the unwanted homodimer pairs produced as byproducts of the double plasmid systems were not incorporated as well as the heterodimers were.

a. Preparation of pPhoC Expression Vector for Expressing Monomeric Bacterial Alkaline Phosphatase The expression vector pPhoC was derived from a pComb2-8-derived expression vector, pC8PhoAm. The vector pC8PhoAm resulted from the ligation of an amber mutation-containing sequence into an Xho I and Spe I-digested pComb2-8 expression vector prepared in Example 1b. The amber mutation-containing sequence containing amplified Xho I and Spe I restriction sites resulted from PCR on template genomic DNA obtained by boiling *E. coli* XL1-blue cells with the primers, 5'-GCCGCGTCTAGACCTAGGGGTGGCGGAGGTAC-ACCAGAAATGCCTGTTCTG -3'(SEQ ID NO:95) and 5'-AGGCTTACTAGTTTTCAGCCCCAGAGCGGCTTT-3' (SEQ ID NO:96). The PCR reaction, containing 5 units Taq polymerase in manufacturer's buffer, was subjected to denaturation at 94 C. for 30 seconds, followed by 25 cycles of 94 C. for 15 seconds, 52 C. for 15 seconds, 72 C. for 2 minutes, using a Perkin Elmer GeneAmp 9600 instrument. The resultant PCR fragment was then digested with Spe I, partially digesting with BspH I, and filled in with Klenow fragment. Following agarose gel electrophoresis, the large 3.6 kilobase vector fragment was isolated, self-ligated with T4 ligase, digested with Spe I and Xho I and inserted into the linearized pComb2-8 vector.

A catalytically active clone was obtained by picking a blue colony from the ligation transformation plated on LB X-P plates as described by Light et al., *Bioorg. Med. Chem. Lett.*, 3:1073–1078 (1992). The pPhoC vector contains b-lactamase resistance marker and high copy number replicon of the colE1 incompatibility group that is compatible with p15A.

b. Preparation of Phage with Bacterial Alkaline Phosphatase on the Coat Protein 8

Phage were grown in *E. coli* XL1-blue cells containing the plasmid(s) pPhoC, pPho8B, or pPhoL8B, or plasmids pPhoC and pPho8B, or pPhoC and pPhoL8B. The plasmids were prepared as described in Examples 5 and 8. A 10 ml overnight culture grown at 37 C. with the appropriate antibiotics (10 mg/ml tetracycline, 100 mg/ml carbenicillin and/or 30 mg/ml chloramphenicol) was infected with $6 \times 10^{10}$ plaque forming units of R408 helper phage, diluted 30-fold into fresh super broth with 10 mM $MgCl_2$, 1 mM $ZnCl_2$, half strength antibiotics but no tetracycline, and 1 mM isopropylthiogalactoside, and grown overnight. Cells and debris were removed by centrifugation at 8600×g for 20 minutes.

Since some of the vector combinations also produced free BAP dimers not anchored to phage, the resulting phage were purified from unattached enzyme and other contaminants by precipitation, CsCl buoyant density centrifugation, and two further rounds of centrifugation. In each step, insoluble aggregates and debris were discarded. The purified phage were then analyzed by electrophoresis and the amount of enzyme quantitated by a colorimetric assay.

For phage purification, to the phage containing supernatant was added one-fifth volume of a solution containing 20% w/v PEG-8000 and 2.5M NaCl. The mixture was incubated at 4 C. for 30 minutes and the precipitated phage pelleted by centrifugation at 14,000×g for 15 minutes. The supernatants were discarded and the phage resuspended by shaking at 37 C., 300 rpm, 20–60 minutes, in 30 ml of 10 mM Tris-HCl at pH 7.5, 10 mM $MgCl_2$, 1 mM $ZnCl_2$. Debris and aggregated phage were removed by centrifugation at 14,000×g for 15 minutes. The precipitation was repeated with one-sixth volume of 20% w/v PEG-8000, 2.5M NaCl, the phage pellet resuspended in 11 ml 10 mM Tris-HCl at pH 7.5, 10 mM $MgCl_2$, 1 mM $ZnCl_2$, and the debris removed as above. CsCl (4.94 g) was added and the density gradient established by centrifugation at 5 C. at 143,000×g for 48 hours. The phage bands were removed in a 2 ml volume, diluted to 13 ml with 150 mM NaCl, 10 mM Tris-HCl at pH 7.5, 10 mM $MgCl_2$, 1 mM $ZnCl_2$(TBSMZ), and the phage pelleted at 5 C. at 143,000×g for 24 hours. The phage were resuspended as above in 2 ml TBSMZ and repelleted at 4 C., 259,000×g for 2 hours. The final phage preparations were resuspended in 0.5 ml of TBSMZ and stored at 4 C.

C. Assay for Enzymatic Activity

To compare the amount of active alkaline phosphatase enzyme incorporated onto phage, 10 ml of purified phage were added to 1 ml of 1M Tris-HCl at pH 8.0 containing 1 mg/ml para-nitrophenylphosphate at 23 C. The appearance of yellow color was followed at 404 nm, and the change in absorbance fit to a line, with the slopes reported as the rate of hydrolysis. Under these conditions, the calculated rates of hydrolysis were directly proportional to the amounts of active enzyme.

When the rates are normalized for the amount of phage and compared to the background, two trends were apparent. First, coexpressing free BAP with BAP-g8p fusion increased the activity by a factor of six (relative ratio 6.4 to 39). Second, adding the flexible linker increased the incorporation another factor of 3.5 (39 to 140). Comparison to phage grown in the presence of BAP-linker-g8p only (pPhoL8B) demonstrated that the linker alone was not responsible for increased BAP on the surface of phage.

From the reaction rates, the number of BAP on the surface of phage were estimated. The total amount of enzyme were estimated to be 3 nM from the measured rate of 0.098 AU/min divided by the extinction coefficient of the product of $1.6 \times 10^4$ AU/cmM [Halford, *Biochem. J.*, 125:319–327 (1971)], divided by $k_{cat}$ of WT BAP of approximately 30 s$^{-1}$ [Matlin et al., *Biochem.*, 31:8196–8200 (1992)]. The total number of phage particles were estimated from the absorbance at 269 nm multiplied by $6 \times 10^{16}$ particles/ml divided by the number of nucleotides in the genome, 6391, to give a concentration of 3 nM phage particles. Dividing enzyme concentration by the phage concentration gave an average number of one BAP per phage. This estimation assumes that free BAP and BAP on phage have similar catalytic rate constants.

d. Gel Electrophoresis

Precast acrylamide tris-glycine gels were purchased from Novex (San Diego, Calif.). Samples were prepared as follows: cultures were sonicated, the debris pelleted, and the supernatant diluted 1:5; or the final phage preparation was used directly. The samples were boiled for 5 minutes with a final concentration of 1 mM b-mercaptoethanol, 10% sucrose, and 11% SDS. Thirty microliters of the samples were then electrophoresed on a 10% gel in 25 mM Tris-HCl at pH 8.3, 192 mM glycine, 0.1% SDS. The proteins were then transferred to "IMMOBILON-P" (Millipore Co., Bedford, Mass.), blocked, incubated with rabbit anti-BAP IgG, and visualized by chemiluminescent detection (Amersham Co., Arlington Heights, Ill.). Purified rabbit IgG directed against bacterial alkaline phosphate was produced by standard methods (Harlow et al., Antibodies: A Laboratory Manual, Cold Spring Harbor Laboratory Press, Cold Spring Harbor (1988) or purchased from 5 Prime 3 Prime, Inc. (Boulder, Colo.).

The results of the Western blots probed with anti-BAP rabbit IgG showed that the cultures produced fusion protein of the expected sizes: BAP monomer (expected 45 kD), BAP-g8p fusion (50.2 kD), and BAP-linker-g8p (51.7 kD), and double plasmid transformants. Approximately equal amounts of purified phage from the respective cultures were also electrophoresed. While not quantitative, the blots indicated that BAP heterodimers that were only anchored to g8p by one half of the dimer were best incorporated into soluble phage From analysis of the Western blot, the best system for incorporation of BAP protein onto phage was the BAP:BAP-linker-g8p strategy resulting from stable transformants containing both the pPhoC plus pPhoL8B expression vectors.

e. Electron Microscopy

For electron microscopic analysis, phage were absorbed onto a carbon-parlodion grid, the grids washed and then incubated with rabbit anti-BAP IgG, washed and then labeled with 10 nm gold-goat anti-rabbit conjugate. The samples were examined at a relative magnification of 30,000.

The resultant electron micrographs revealed that from zero to as many as three BAP were present on per single length phage. In addition, double and triple length phage bearing as many as four BAP were also seen. The number of BAP per phage determined by electron microscopy is similar to the number determined by activity measurements as described above.

f. Analysis of Enhanced Detection with Dimerized Bacterial Alkaline Phosphatase

The improvements for the display of BAP dimers on major coat protein g8p of filamentous phage showed that unlike coat protein 3 display (g3p), maximal incorporation occurred only when one half of the BAP dimer was attached to the coat protein 8 (g8p). An interesting similarity between both display sites was that both the BAP-g3p and BAP:BAP-linker-g8p display gave approximately one active BAP per phage, even though there were thousands of potential attachment sites for a g8p fusion protein.

With earlier studies of peptide epitope [Greenwood et al., *J. Mol. Biol.,* 220:821–827 (1991)], Fab [Kang et al., *Proc. Natl. Acad. Sci., USA,* 87:6378–6382 (1991)], and bovine pancreatic trypsin inhibitor BPTI [Markland et al., *Gene,* 109:13–19 (1991)[ g8p fusion display, a clear trend of size of fusion to number of fusions incorporated into phage can be seen. With a nine residue epitope, fusion phage can be constructed such that every copy of g8p coat contains the fusion. With a twelve residue epitope, hybrid phage with a coat consisting of a mixture of 10–30% epitope-g8p fusion (100–300 copies/phage) and remainder wild type g8p could be obtained [Greenwood et al., supra, (1991)]. In the case of BPTI, a 58 residue protein (7 kD) fused to g8p, typically 30–60 copies of BPTI per phage were incorporated [Markland et al., supra, (1991)]. When a larger heterodimeric Fab of approximately 440 residues was used that was approximately 45 kD, electron micrograph studies demonstrated 1–24 Fab's per phage [Kang et al., supra, (1991)]. In addition, one to three 928 residue BAP dimers (92 kD with linker) could be incorporated per phage. Although the length of the phages in these studies differ, a clear trend is seen-the larger the protein, the fewer copies incorporated on phage. An upper size limit, if it exists, is not known.

Closer examination of the Western blots indicated that degradation of the BAP-g8p fusions occurred. Thus, it seems likely that the observed activity of the fusion-only phage was due to removal of the g8p tail, leaving some free BAP, to pair with BAP-g8p on the phage surface. Secondly, the purification scheme only yielded soluble phage. Pairings of BAP-g8p on different phages gave insoluble aggregates, which would have been discarded. In either case, a free BAP monomer is needed to cap the BAP-linker-g8p fusion for maximal activity and incorporation onto phage.

The need for a free BAP monomer illustrates interesting aspects of coat protein 8 phage display. Apparently BAP-linker-g8p monomers are not able to assemble into dimers on phage. Whether this inability is due to steric limitations on the phage, or more likely, limitations imposed by the phage extrusion process from *E. coli* is still unresolved. One could imagine that BAP-linker-g8p would first assemble in the periplasm into dimers with the g8p tails associated with the cell membrane. The doubly anchored dimer might then be prohibited from incorporation into phage by steric or chelate type effects favoring it to remain anchored to the cell membrane.

It also remains to be seen whether incorporation of fusions is limited by kinetics of phage assembly or steric effects regarding extrusion of the phage through the cell wall. A kinetic limitation occurs from competition of wild type g8p and fusion-g8p for incorporation into phage. Such competition effects were observed in the display of BPTI on g8p, where lowering the expression of the wild type g8p with respect to BPTI-g8p fusion increased the total number of BPTI on the phage [Markland et al., supra, (1991)]. On the other hand, a steric limitation is best described as attaching hooks in the form of a g8p fusion protein to the phage needle, which must still pass through the outer cell wall to become free phage.

9. Preparation of Displayed Dimerized Alkaline Phosphatase and Heterodimeric Polypeptides The improvements in BAP display on coat protein shown in Example 8 provide improvements to the PhoPhab system prepared in Examples 1–4. Two methods described herein provide for the expression of a heterodimeric receptor on the surface of bacteriophage simultaneously with a dimerized heterologous polypeptide indicator system, in particular, dimerized alkaline phosphatase.

From the results of the incorporation of BAP onto the surface of bacteriophage as described in Examples 1–8, two features were identified that increased the incorporation of active bacteriophage alkaline phophastase (BAP) displayed on g8p of phage. Essentially, the improvement came by attaching the enzyme to the gene VIII coat protein (g8p) by a 20 amino acid linker to only one of the enzyme's otherwise identical subunits. This was accomplished by using two plasmids to express the two different subunits. The plasmid pPhoL8B provided the BAP-linker-g8 subunit and the plasmid pPhoC provided the free soluble BAP monomer. These two halves formed a dimer, which was incorporated into phage much better than before with the pPho8cat plasmid.

These results indicated a new design for improving the PhoPhab system, which at first glance would be to add the expression vectors, pPhoC, pPhoL8B and a heterodimeric Fab-producing pComb3, for producing PhoPhabs with a dimerized indicator detection system. However, this strategy would not work because pPhoC and pComb3 have origins of replication of the same incompatibility group thereby making such a transformation unstable. Therefore, another method of producing free BAP monomers to pair with the BAp-linker-g8p monomer were designed based on the previously described expression vector systems. Two such methods are described herein.

a. Construction of a Dual Alkaline Phosphatase Expression Vector

One method for preparing dimerized heterologous indicator polypeptides for expression on the surface of bacteriophage is the use of an expression vector designed specifically to allow expression of monomeric soluble forms of BAP simultaneously with monomeric insoluble alkaline phosphatase anchored to a bacteriophage coat protein membrane anchor. The preferred coat protein membrane anchors are coat protein 8 and 3, respectively cp8 and cp3 (also referred to as g8p and g3p).

For a single vector to provide for the dual expression of both a soluble as well as an anchored form of alkaline phosphatase, the use of a partially suppressed amber codon is required as described by Miller, *Methods Enz.,* 255:2396–2404 (1991), the disclosure of which is hereby incorporated by reference. In the presence of the appropriate suppressor tRNA, one gene would give both the free monomeric BAP and the fusion proteins of BAP anchored to a coat protein. The use of suppressor tRNA genes in the context of dual expression is well known to one of ordinary skill in the art. The preferred anchored alkaline phosphatase protein for use in the PhoPhab detection system is the anchorage of BAP to coat protein 8 through a linker polypeptide such as described in Example 5 resulting from the expression vector pPhoL8B. The other vectors for expressing anchored BAP, including pPho8B and pPhoL8, are also contemplated for use herein.

By inserting an amber stop (TAG) codon into the linker coding sequence of between the PhoA and g8p coding regions, one plasmid is used to produce BAP and BAP-linker-g8p, where two plasmids were used before. Induction of the amber codon bearing plasmid pPhoAL8, prepared as described below, in the presence of an amber suppressor tRNA results in the expression of free monomeric BAP and BAP-linker-g8p, with BAP-linker-g8p resulting from partial suppression of the amber stop codon. The use of suppressor tRNA and synthetic suppressor tRNAs to generate altered proteins is well known in the art. See, Miller, "Use of Nonsense Suppression to Generate Altered Proteins", in *Methods in Enzymology,* 208:543–563 (1991). Suppressors are known that insert various amino acids in place of an amber stop codon, with various efficiencies. Coding sequences for such suppressors are incorporated into pPhoAL8 to form the final expression vector, pPhoAL8S, which in the presence of a Fab-encoding pComb3 plasmid and helper phage provides for improved PhoPhabs that have increased signal due to better incorporation of BAP as described above. The system is then optimized for PhoPhab production by testing known suppressors that insert different amino acids at varying levels, and the position of the amber stop codon is then moved because suppression in known to be dependent on the context.

1) Construction of pPhoAL8S Expression Vector

Kunkel site-directed mutagenesis is performed according to standard protocols provided with the In Vitro Mutagenesis Kit commercially available from Bio-Rad, Richmond, Calif. For the mutagenesis, the oligonucleotide primer designated AMLNK having the nucleotide sequence 5'-TCCACTAGTTAGGGTGGTG-3' (SEQ ID NO:97) was used in PCR on the single stranded DNA template of the phagemid pComb2-8 into which the 63 bp linker-encoding sequence was inserted forming pComb2-8L as described in Example 5c for use in the preparation of pPhoL8. The resulting plasmid, designated pJ6L112s5, was identical to pComb2-8L, with the exception that the first codon of the linker immediately after the Spe I site is now the amber stop codon, TAG.

To form pPhoAL8, the Spe I/Sac I fragment of pJ6L112s5 is then exchanged with the Spe I/Sac I fragment of pPhoL8B, prepared in Example 5d.

For introducing the amber suppressor, a preexisting plasmid source, for example pGFIB-1-gly1 described by Kleina et al., *J. Mol. Biol.,* 213:705–717 (1990). pPhoAL8 is then prepared for insertion of the amber suppressor tRNA sequence by digesting with Sac I, and blunt ended with T4 DNA polymerase, followed by dephosphorylation with calf intestinal alkaline phosphatase. The suppressor tRNA gene is then digested from pGFIB-1-gly1 with Pvu II, and blunt ended with T4 DNA polymerase. The resulting small fragment is then isolated by gel electrophoresis. This fragment is then ligated into the digested and filled pPhoAL8 to form pPhoAL8S, with either orientation of the insert being functional. The resultant pPhoAL8S expression vector is then used with the PhoPhab system as described in Example 5 for the dual expression of heterodimeric ligand-binding Fabs with the alkaline phosphatase indicator system in the form of a dimer.

2) Use a *E. Coli* strain that Constitutively Expresses BAP

Mutants of *E. coli* are known that constitutively express monomeric soluble forms of BAP. For example, see *E. coli* strain phoR8, described by Kreuzer et al., *Genetics,* 81:459–468 (1975). Infecting such a strain with helper phage that also contained the plasmids PhoL8B and a Fab-bearing pComb3 vector as described in Example 6 would form PhoPhabs with improved incorporation of dimeric BAP, thereby providing an enhanced indicator polypeptide detection signal. In this case, the dimer is only attached to the phage by the BAP subunit encoded by pPhoL8B while the "free" half of the dimer is provided by the PhoR⁻ bacterium.

In addition, nearly any desired bacterial strain are mutatable by techniques well known to one of ordinary skill in the art to a PhoR- phenotype such that it then constitutively expressed BAP. Miller, in Experiments in Molecular Genetics, Cold Spring Harbor Laboratory Press, (1972), described the process for mutating bacterial strains to accomplish the constitutive expression of monomeric soluble BAP.

In addition to the above PhoPhab system having a dimerized indicator polypeptide detecting system, an alternate use of phage display for isolation of mutant-wild type pairs is also contemplated. BAP, which is normally a homodimer, is converted to a heterodimer through a free BAP and BAP-linker-g8p fusion. This heterodimer is purified by centrifugation of the attached phage. The net effect is purification of the free-fusion pair from the three possible pairings of free-free, free-fusion, and fusion-fusion proteins produced by dual expression of each half. A specific protease site is then added to the linker to allow release of the enzyme from the phage. Thus, by using phage display, it should be possible to separate mutant-wild type pairs of a normally homodimeric protein with a centrifuge.

In summary, the PhoPhab system of this invention which links an antigen-specific Fab to multiple copies of alkaline phosphatase has advantages of simplicity and time over conventional techniques. Traditional methods for immunochemical techniques such as ELISA's and Western blots require an antibody against the antigen of interest and a secondary antibody-enzyme conjugate for detection, which requires two immunizations, as well as the production of hybridomas if monoclonal specificity is desired. Instead, this new technique uses phage display to isolate the desired binding specificity and eliminates the need for a secondary reagent, while still achieving amplification of the antigen signal.

The specificity of the reagent is determined by the panning selection process, and either monoclonal or polyclonal mixtures can be used. The desired specificity can be selected by panning a small amount of a heterodimeric library, and then simply growing the desired reagent with bacterial culture techniques. The possibility exists to remove unwanted cross reactivity by subtractive panning. When coupled with a pre-made synthetic library, antigen specific reagents can be produced without immunization in only a few days, compared to months for the production of monoclonal antibodies. The phage reagents are also anticipated to be less expensive to produce.

Filamentous phage frameworks can be extended beyond the PhoPhab example illustrated here. The PhoPhab system of this invention can be extended to screening uncharacterized heterodimeric libraries to select reagents exhibiting specificity to a preselected ligand. Other enzymes and proteins could be linked on filamentous phage, using the different coat proteins to vary the number of attachments. For example, a binder-cpIII-phage-(cpVIII-enzyme)$_n$ system could be used to deliver multiple copies of an enzyme to a specific site in vitro, and perhaps in vivo, allowing for antigenic responses. The use of filamentous phage need not be limited to single phage, but networks of phage frameworks could be linked. One way would be to direct Fab#1-phage-enzyme against Fab#2-phage-antigen#1, thereby creating a large amplification in the number of enzyme molecules bound to antigen#2.

Moreover, dimerized alkaline phosphatase in the context of surface phage display results in an enhanced detection system for use in the PhoPhab system. Bacterial alkaline phosphatase has thus been incorporated into filamentous phage as a dimer attached through one monomer to the major phage coat protein. Unlike g3p display, to obtain an active enzyme dimer assembled on phage g8p, a free monomer is needed to complement the fusion monomer. BAP-g8p or BAP-linker-g8p fusions alone are not assembled as well on the phage. Furthermore, a 20 residue linker increased the number of BAP dimers on the phage. In the best case, an average of one BAP dimer per phage is incorporated, with three being the maximum number observed on a single length phage.

The foregoing is intended as illustrative of the present invention but not limiting. Numerous variations and modifications can be effected without departing for the true spirit and scope of the invention.

What is claimed is:

1. A filamentous phage comprising:
   a) a heterologous polypeptide fused to a first filamentous phage coat protein membrane anchor; and
   b) a heterodimeric receptor comprised of first and second receptor polypeptides wherein one of said receptor polypeptides is fused to a second filamentous phage coat protein membrane anchor,
      wherein said first and second coat protein membrane anchors are selected from the group consisting of cpIII and cpVIII.

2. The filamentous phage of claim 1 wherein said first and second membrane anchors are not the same.

3. The filamentous phage of claim 1 wherein said heterologous polypeptide is an indicator polypeptide.

4. The filamentous phage of claim 1 further comprising:
   c) a dimer having a first subunit of said dimer comprising a heterologous polypeptide fused to a first filamentous phage coat protein membrane anchor and a second subunit of said dimer that is soluble.

5. The filamentous phage of claim 2 wherein said first and second membrane anchors are cpVIII and cpIII, respectively.

6. The filamentous phage of claim 3 wherein said indicator polypeptide is alkaline phosphatase.

7. The filamentous phage of claim 4 wherein said first and second subunits are alkaline phosphatase.

8. The filamentous phage of claim 4 wherein said heterologous polypeptide of said first subunit is fused to said coat protein membrane anchor through a linker polypeptide.

9. The filamentous phage of claim 8 wherein said linker peptide has the amino acid residue sequence in SEQ ID NO:91.

10. A library of filamentous phage particles wherein each filamentous phage particle comprises:
    a) a heterologous polypeptide fused to a first filamentous phage coat protein membrane anchor; and
    b) a heterodimeric receptor comprised of first and second receptor polypeptides wherein one of said receptor polypeptides is fused to a second filamentous phage coat protein membrane anchor,
       wherein said first and second coat protein membrane anchors are selected from the group consisting of cpIII and cpVIII.

11. The library of claim 10 wherein said library contains at least $10^7$ different species of said heterodimeric receptor.

12. The library of claim 10 further comprising:
    c) a dimer having a first subunit of said dimer comprising a heterologous polypeptide fused to said first filamentous phage coat protein membrane anchor and a second subunit of said dimer that is soluble.

13. The filamentous phage of claim 12 wherein said first and second subunits are alkaline phosphatase.

14. The filamentous phage of claim 12 wherein said heterologous polypeptide of said first subunit is fused to said coat protein membrane anchor through a linker polypeptide.

15. The filamentous phage of claim 14 wherein said linker peptide has the amino acid residue sequence in SEQ ID NO:91.

16. A method for producing a filamentous phage particle having on the particle surface (i) a first fusion polypeptide and (ii) a heterodimeric receptor consisting of first and second receptor polypeptides, which method comprises the steps of:
    a) introducing into a prokaryotic host cell permissive for filamentous phage replication a first vector comprising a nucleotide sequence which expresses said first fusion polypeptide, said first fusion polypeptide comprising a heterologous polypeptide fused to a first filamentous phage coat protein membrane anchor;
    b) introducing into said prokaryotic host cell a second vector for expressing said heterodimeric receptor comprising a nucleotide sequence which expresses said first and second receptor polypeptides, wherein one of said receptor polypeptides is fused to a second filamentous phage coat protein membrane anchor; and
    c) maintaining said prokaryotic host cell containing said introduced first and second vectors under conditions sufficient for filamentous phage production and under conditions sufficient for expression of said first fusion polypeptide and expression of said heterodimeric receptor, thereby forming said phage particle,
       wherein said first and second coat protein membrane anchors are selected from the group consisting of cpIII and cpVIII.

17. The method of claim 16 wherein said first and second membrane anchors are not the same.

18. The method of claim 16 wherein said heterologous polypeptide is an indicator polypeptide.

19. The method of claim 16 wherein said procaryotic host cell produces soluble heterologous polypeptide.

20. The method of claim 16 wherein said first vector further comprises:
    i) a first nucleotide sequence comprising a nonsense chain termination codon operatively linked downstream to said nucleotide sequence encoding said heterologous polypeptide, wherein said termination codon results in the expression of a soluble heterologous polypeptide, and;
    ii) a second nucleotide sequence comprising a tRNA suppressor gene, wherein expression of said suppressor gene allows sufficient translation through said termination codon to result in the expression of a heterologous polypeptide fused to a first filamentous phage coat protein membrane anchor.

21. The method of claim 17 wherein said first and second membrane anchors are cpVIII and cpIII, respectively.

22. The method of claim 18 wherein said indicator polypeptide is alkaline phosphatase.

23. The method of claim 19 wherein said procaryotic host is a PhoR mutant which produces soluble alkaline phosphatase.

24. The method of claim 20 wherein said heterologous polypeptide is fused to said coat protein membrane anchor through a linker polypeptide.

25. The method of claim 24 wherein said linker polypeptide has the amino acid residue sequence in SEQ ID NO:91.

26. A method for producing a filamentous phage particle containing a surface-exposed heterodimeric receptor having a preselected binding specificity, which method comprises the steps of:
 a) providing a library of filamentous phage particles wherein each filamentous phage particle comprises:
  i) an indicator polypeptide fused to a first filamentous phage coat protein membrane anchor; and
  ii) a heterodimeric receptor comprised of first and second receptor polypeptides wherein one of said receptor polypeptides is fused to a second filamentous phage coat protein membrane anchor, said heterodimeric receptor able to bind to a preselected ligand;
 b) adsorbing members of said provided library onto a plurality of preselected ligand molecules in the solid phase to form a plurality of solid-phase adsorbed phage particles;
 c) assaying said solid phase for the presence of said indicator polypeptide, and thereby the presence of a solid-phase adsorbed phage particle containing said surface-exposed heterodimeric receptor having a preselected binding specificity; and
 d) recovering said solid-phase adsorbed phage particle that contains said heterodimeric receptor,
 wherein said first and second coat protein membrane anchors are selected from the group consisting of cpIII and cpVIII.

27. The method of claim 26 wherein said first and second membrane anchors are not the same.

28. The method of claim 26 wherein said heterologous polypeptide is an indicator polypeptide.

29. The method of claim 26 further comprising:
 iii) a dimer having a first subunit of said dimer comprising an indicator polypeptide fused to a first filamentous phage coat protein membrane anchor and a second subunit of said dimer that is soluble.

30. The method of claim 27 wherein said first and second membrane anchors are cpVIII and cpIII, respectively.

31. The method of claim 28 wherein said indicator polypeptide is alkaline phosphatase.

32. The method of claim 29 wherein said first and second subunits are alkaline phosphatase.

33. The method of claim 29 wherein said first subunit is fused to said coat protein membrane anchor through a linker polypeptide.

34. The method of claim 33 wherein said linker peptide has the amino acid residue sequence in SEQ ID NO:91.

35. A method for detecting the presence of a preselected ligand in a sample comprising the steps of:
 a) contacting said sample with a filamentous phage particle comprising:
  i) an indicator polypeptide fused to a first filamentous phage coat protein membrane anchor, and
  ii) a heterodimeric receptor comprised of first and second receptor polypeptides wherein one of said receptor polypeptides is fused to a second filamentous phage coat protein membrane anchor, said heterodimeric receptor able to bind to said preselected ligand; to form a ligand binding reaction admixture;
 b) maintaining said admixture under conditions sufficient for said heterodimeric receptor to bind to said ligand and form a ligand-filamentous phage particle complex; and
 c) detecting the presence of said indicator polypeptide on said complex, thereby detecting said preselected ligand,
 wherein said first and second coat protein membrane anchors are selected from the group consisting of cpIII and cpVIII.

36. The method of claim 35 wherein said first and second membrane anchors are not the same.

37. The method of claim 35 wherein said indicator polypeptide is alkaline phosphatase.

38. The method of claim 35 further comprising:
 iii) a dimer having a first subunit of said dimer comprising an indicator polypeptide fused to a first filamentous phage coat protein membrane anchor and a second subunit of said dimer that is soluble.

39. The method of claim 36 wherein said first and second membrane anchors are cpVIII and cpIII, respectively.

40. The method of claim 38 wherein said first and second subunits are alkaline phosphatase.

41. The method of claim 38 wherein said first subunit is fused to said coat protein membrane anchor through a linker polypeptide.

42. The method of claim 41 wherein said linker peptide has the amino acid residue sequence in SEQ ID NO:91.

43. A vector for expressing first and second polypeptide subunits of an alkaline phosphatase dimer which dimer upon expression assembles on the surface of a filamentous phage particle, said vector comprising a nucleotide sequence that encodes:
 a) a suppressor tRNA gene which expresses a suppressor tRNA molecule; and
 b) an expression cassette for expressing said first and second polypeptide subunits, said expression cassette comprising:
  i) a transcriptional promoter and transcriptional terminator for producing a messenger RNA transcript that encodes said first and second polypeptide subunits;
  ii) a first open reading frame that encodes soluble alkaline phosphatase beginning with a translational initiator and ending with a nonsense chain termination codon selected from the group consisting of amber, ochre and opal; and
  iii) a second open reading frame operatively linked downstream to said first open reading frame, said second open reading frame encoding a filamentous phage coat protein membrane anchor such that upon suppression of the nonsense chain termination codon by said suppressor tRNA molecule, said first and second open reading frames are translated as one polypeptide, the translated polypeptide being a fusion protein having alkaline phosphatase operatively linked in frame with the filamentous phage coat protein membrane anchor, wherein said coat protein membrane anchor is selected from the group consisting of cpIII and cpVIII.

44. The vector of claim 43 wherein said first and second open reading frames are operatively linked by a nucleotide sequence that encodes a linker polypeptide that operatively links alkaline phosphatase to said filamentous phage coat protein membrane anchor.

45. The vector of claim 44 wherein said linker polypeptide has the amino acid residue sequence in SEQ ID NO:91.

* * * * *

UNITED STATES PATENT AND TRADEMARK OFFICE
CERTIFICATE OF CORRECTION

PATENT NO. : 5,770,356  
DATED : June 23, 1998  
INVENTOR(S) : Light et al.

Page 1 of 1

It is certified that error appears in the above-identified patent and that said Letters Patent is hereby corrected as shown below:

Column 1,  
Line 8, replace the paragraph with the following:  
-- This invention was made with government support under Contract Nos. CA56483 and GM15392-02 by the National Institutes of Health. The government has certain rights in the invention. --

Signed and Sealed this

Twenty-sixth Day of March, 2002

Attest:

*Attesting Officer*

JAMES E. ROGAN  
*Director of the United States Patent and Trademark Office*